US005856326A

United States Patent [19]
Anthony et al.

[11] Patent Number: 5,856,326
[45] Date of Patent: Jan. 5, 1999

[54] INHIBITORS OF FARNESYL-PROTEIN TRANSFERASE

[75] Inventors: Neville J. Anthony, Hatfield; Terrence M. Ciccarone, Telford; Christopher J. Dinsmore, North Wales; Robert P. Gomez, Perkasie; Theresa M. Williams, Harleysville; George D. Hartman, Lansdale, all of Pa.

[73] Assignee: Merck & Co., Inc., Rahway, N.J.

[21] Appl. No.: 600,728

[22] Filed: Mar. 1, 1996

Related U.S. Application Data

[63] Continuation-in-part of Ser. No. 470,690, Jun. 6, 1995, abandoned, which is a continuation-in-part of Ser. No. 412,829, Mar. 29, 1995, abandoned.

[51] Int. Cl.$^6$ ...................... A61K 31/495; C07D 403/06; C07D 401/06; C07D 241/04
[52] U.S. Cl. .................. 514/252; 544/370; 544/360; 544/357; 544/364; 544/231; 544/384; 544/391; 540/492; 540/575; 514/218; 514/255
[58] Field of Search .............................. 544/370; 514/252

[56] References Cited

U.S. PATENT DOCUMENTS

| | | | |
|---|---|---|---|
| 3,491,098 | 1/1970 | Archer | 514/252 |
| 4,940,793 | 7/1990 | Botre' et al. | 544/349 |
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,326,773 | 7/1994 | De Solms et al. | 514/336 |
| 5,340,828 | 8/1994 | Graham et al. | 514/357 |
| 5,352,705 | 10/1994 | Deana et al. | 514/630 |
| 5,428,164 | 6/1995 | Thurkauf et al. | 544/295 |
| 5,439,918 | 8/1995 | Desolms et al. | 514/307 |
| 5,478,934 | 12/1995 | Yuan et al. | 540/546 |
| 5,480,893 | 1/1996 | Graham et al. | 514/336 |
| 5,491,164 | 2/1996 | De Solms et al. | 514/423 |
| 5,504,212 | 4/1996 | De Solms et al. | 546/336 |
| 5,646,281 | 7/1997 | Thurkauf et al. | 544/295 |

FOREIGN PATENT DOCUMENTS

| | | |
|---|---|---|
| A 820242 | 1/1975 | Belgium . |
| 0 064 705 A1 | 11/1982 | European Pat. Off. . |
| 0 456 180 A1 | 11/1991 | European Pat. Off. . |
| 49-110680 | 10/1974 | Japan . |
| WO 95/08542 | 9/1994 | Japan . |
| H7-112930 | 5/1995 | Japan . |
| WO 91/16340 | 10/1991 | WIPO . |
| WO 92/12134 | 7/1992 | WIPO . |
| WO 95/11917 | 5/1994 | WIPO . |
| WO 95/00497 | 1/1995 | WIPO . |
| WO 95/10514 | 4/1995 | WIPO . |
| WO 95/10515 | 4/1995 | WIPO . |
| WO 95/10516 | 4/1995 | WIPO . |
| WO 95/34311 | 12/1995 | WIPO . |

OTHER PUBLICATIONS

Nagasu et al, *Cancer Research* 55, pp. 5310–5314, (1995).
Kmonicek et al, *Collect. Czech. Commun.* 55, pp. 1817–1827, (1990).
J. of Med. Chem., vol. 35, No. 22, pp. 4118–4134 (1992), by E. Carceller, et al.
J. of Med. Chem., vol. 7, No. 2, pp. 154–158 (1964), by O. E. Fancher, et al.
J. of Med. Chem., vol. 38, No. 12, pp. 2251–2255 (1995), by A. Thurkauf, et al.
Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).
Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).
James, G.L. et al., Benzodiazepine Peptidomimetic BZ–5B Interrupts the MAP Kinase Activation Pathway in H–Ras––transformed Rat–1 Cells, but Not in Untransformed Cells, The Journal of Biological Chemistry, vol. 369, No. 44, pp. 27705–27714 (1994).
James, G.L. et al., "Benzodiazepine Peptidomimetics: Potent Inhibitors of Ras Farnesylation in Animal Cells", Science, vol. 260, pp. 1937–1942 (1993).
James, G. et al., "Polylysine and CVIM Sequences of K–RasB Dictate Specificity of Prenylation and Confer Resistance to Benzodiazepine Peptidomimetic in Vitro," The Jour. of Biol. Chem., vol. 270, No. 11, pp. 6221–6226 (1995).
Kohl, N.E., et al., "Selective Inhibition of ras–Dependent Transformation by a Farnesyltransferase Inhibitor," Science, vol. 260, pp. 1934–1937 (1993).
Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).
Kohl, N.E., et al., "Inhibition of farnesyltransferase induces regression of mammary and salivary carcinomas in ras transgenic mice," Nature Medicine, vol. 1, No. 8 (1995), pp. 792–797.
Pompliano, D.L., "Steady–State Kinetic Mechanism of Ras Farnesyl:Protein Transferase," Biochemistry, vol. 31, pp. 3800–3807 (1992).
Sepp–Lorenzino, L. et al., "A Peptidomimetic Inhibitor of Farnesyl:Protein Transferase Blocks the Anchorage–dependent and–independent Growth of Human Tumor Cell Lines," Cancer Research, vol. 55, pp. 5302–5309 (1995).
Graham, S.L., "Inhibitors of protein farnesylation: a new approach to cancer chemotherapy," Exp. Opin. Ther. Patents, 5(12) pp. 1269–1285 (1995).
Komoto et al, *Chemical Abstracts*, vol. 109, No. 231076 (Abstract for JP 63, 183565, Jul. 28, 1988) (1988).
Khosravi–Far et al, *Cell Growth & Differentiation 3*, pp. 461–469 (1992).

*Primary Examiner*—Emily Bernhardt
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

13 Claims, No Drawings

INHIBITORS OF FARNESYL-PROTEIN TRANSFERASE

RELATED APPLICATION

The present patent application is a continuation-in-part application of copending application Ser. No. 08/470,690, filed Jun. 6, 1995 now abandoned, which is a continuation-in-part application of copending application Ser. No. 08/412,929, filed Mar. 29, 1995 now abandoned.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif selves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises peptidomimetic piperazine-containing compounds which inhibit the farnesyl-protein transferase. The instant compounds lack a thiol moiety and thus offer unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formulae A, B and C:

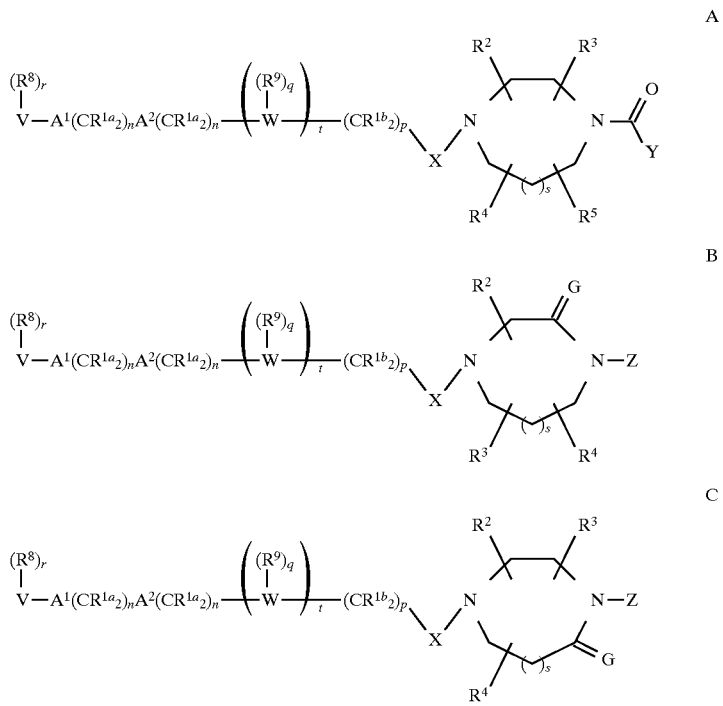

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

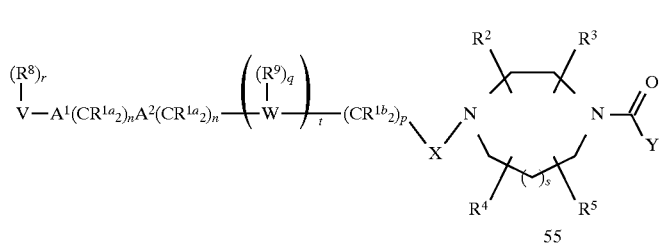

wherein:
$R^{1a}$ and $R^{1b}$ are independently selected from:
  a) hydrogen,
  b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$-, $R^{10}C(O)NR^{10}$-, $(R^{10})_2N$-C(O)—, CN, $NO_2$, $(R^{10})_2N$-C($NR^{10}$)—, $R^{10}C(O)$—, $R^{10}OC(O)$—, $N_3$, —$N(R^{10})_2$, or $R^{11}OC(O)NR^{10}$-,
  c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$-, $R^{10}C(O)NR^{10}$-, $(R^{10})_2N$-C(O)—, CN, $(R^{10})_2N$-C($NR^{10}$)—, $R^{10}C(O)$—, $R^{10}OC(O)$—, $N_3$, —$N(R^{10})_2$, and $R^{11}OC(O)$—$NR^{10}$-;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

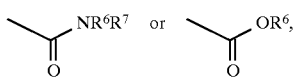

wherein the substituted group is substituted with one or more of:
  1) aryl or heterocycl, unsubstituted or substituted with:
    a) $C_{1-4}$ alkyl,
    b) $(CH_2)_pOR^6$,
    c) $(CH_2)_pNR^6R^7$,
    d) halogen,
    e) CN,
  2) $C_{3-6}$ cycloalkyl,
  3) $OR^6$, 4) $SR^{6a}$, $S(O)R^{6a}$, $SO_2R^{6a}$,

5) —$NR^6R^7$,

6) 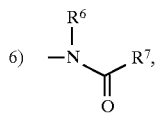

7) 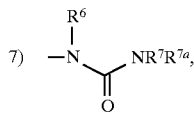

8) 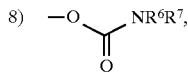

9) 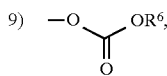

10) 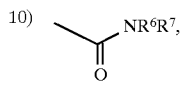

11) —$SO_2$—$NR^6R^7$,

12) 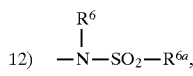

13) 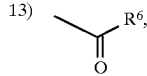

14) 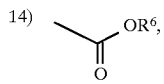

15) $N_3$, or
16) F; or $R^2$ and $R^3$ are attached to the same C atom and are combined to form —$(CH_2)_u$- wherein one of the carbon atoms is optionally replaced by a moiety selected from: O, $S(O)_m$, —NC(O)—, and —$N(COR^{10})$-;

$R^4$ and $R^5$ are independently selected from H and $CH_3$; and any two of $R^2$, $R^3$, $R^4$ and $R^5$ are optionally attached to the same carbon atom;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO,
e) 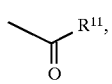

f) —$SO_2R^{11}$, or
g) $N(R^{10})_2$; or $R^6$ and $R^7$ may be joined in a ring;
$R^7$ and $R^{7a}$ may be joined in a ring;
$R^{6a}$ is selected from: $C_{1-4}$ alkyl, $C_{3-6}$ cycloalkyl, heterocycle, aryl, unsubstituted or substituted with:
a) $C_{1-4}$ alkoxy,
b) aryl or heterocycle,
c) halogen,
d) HO,
e) 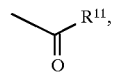

f) —$SO_2R^{11}$, or
g) $N(R^{10})_2$;

$R^8$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$-, $R^{10}C(O)NR^{10}$-, $(R^{10})_2NC(O)$—, $R^{10}_2$N-C$(NR^{10})$—, CN, $NO_2$, $R^{10}C(O)$—, $R^{10}OC(O)$—, $N_3$, —$N(R^{10})_2$, or $R^{11}OC(O)NR^{10}$-, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$-, $R^{10}C(O)NH$—, $(R^{10})_2NC(O)$—, $R^{10}_2$N-C$(NR^{10})$—, CN, $R^{10}C(O)$—, $R^{10}OC(O)$—, $N_3$, —$N(R^{10})_2$, or $R^{10}C(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$-, $R^{10}C(O)NR^{10}$-, $(R^{10})_2NC(O)$—, $R^{10}_2$N-C$(NR^{10})$—, CN, $NO_2$, $R^{10}C(O)$—, $R^{10}OC(O)$—, $N_3$, —$N(R^{10})_2$, or $R^{11}OC(O)NR^{10}$-, and
c) $C_1$–$C_6$ alkyl unsubstituted or substituted by perfluoroalkyl, F, Cl, Br, $R^{10}O$—, $R^{11}S(O)_m$-, $R^{10}C(O)NR^{10}$-, $(R^{10})_2NC(O)$—, $R^{10}_2$N-C$(NR^{10})$—, CN, $R^{10}C(O)$—, $R^{10}OC(O)$—, $N_3$, —$N(R^{10})_2$, or $R^{11}OC(O)NR^{10}$-;

$R^{10}$ is independently selected from hydrogen, $C_1$–$C_6$ alkyl, benzyl and aryl;
$R^{11}$ is independently selected from $C_1$–$C_6$ alkyl and aryl;
$A^1$ and $A^2$ are independently selected from: a bond, —CH=CH—, —C≡C—, —C(O)—, —C(O)$NR^{10}$-, —$NR^{10}C(O)$—, O, —$N(R^{10})$—, —$S(O)_2N(R^{10})$—, —$N(R^{10})S(O)_2$-, or $S(O)_m$;

V is selected from:
a) hydrogen,
b) heterocycle,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;
X is —$CH_2$-, —C(=O)—, or —S(=O)$_m$-;
Y is unsubstituted or substituted aryl or unsubstituted or substituted heterocycle, wherein the substituted aryl or substituted heterocycle is substituted with one or more of:
1) $C_{1-4}$ alkyl, unsubstituted or substituted with:
a) $C_{1-4}$ alkoxy,
b) $NR^6R^7$,
c) $C_{3-6}$ cycloalkyl,
d) aryl or heterocycle,
e) HO, f) —S(O)$_m$R$^{6a}$, or
g) —C(O)NR$^6$R$^7$,
2) aryl or heterocycle,
3) halogen,
4) OR$^6$,
5) NR$^6$R$^7$,
6) CN,
7) NO$_2$,
8) CF$_3$;
9) —S(O)$_m$R$^{6a}$,
10) —C(O)NR$^6$R$^7$, or
11) C$_3$–C$_6$ cycloalkyl m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;
t is 0 or 1; and
u is 4 or 5;
or the pharmaceutically acceptable salts thereof.

In a second embodiment of this invention, the inhibitors of farnesyl-protein transferase are illustrated by the formula B:

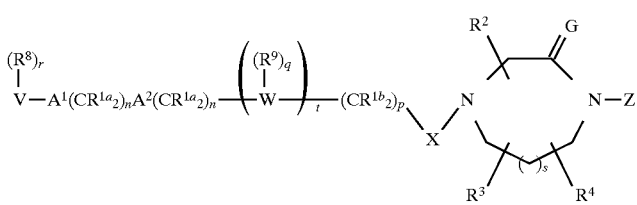

B wherein:
R$^{1a}$ and R$^{1b}$ are independently selected from:
  a) hydrogen,
  b) aryl, heterocycle, C$_3$–C$_{10}$ cycloalkyl, C$_2$–C$_6$ alkenyl, C$_2$–C$_6$ alkynyl, R$^{10}$O—, R$^{11}$S(O)$_m$-, R$^{10}$C(O)NR$^{10}$-, CN(R$^{10}$)$_2$NC(O)—, R$^{10}$$_2$N-C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$-,
  c) unsubstituted or substituted C$_1$–C$_6$ alkyl wherein the substitutent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, R$^{10}$O—, R$^{11}$S(O)$_m$-, R$^{10}$C(O)NR$^{10}$-, (R$^{10}$)$_2$NC(O)—, R$^{10}$$_2$N-C(NR$^{10}$)—, CN, R$^{10}$C(O)—, R$^{10}$OC(O)—, N$_3$, —N(R$^{10}$)$_2$, and R$^{11}$OC(O)—NR$^{10}$-;
R$^2$ and R$^3$ are independently selected from: H; unsubstituted or substituted C$_{1\text{-}8}$ alkyl, unsubstituted or substituted C$_{2\text{-}8}$ alkenyl, unsubstituted or substituted C$_{2\text{-}8}$ alkynyl, unsubstituted or substituted aryl, unsubstituted or substituted heterocycle,

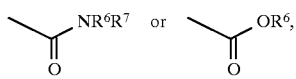

wherein the substituted group is substituted with one or more of:
  1) aryl or heterocycle, unsubstituted or substituted with:
    a) C$_{1\text{-}4}$ alkyl,
    b) (CH$_2$)$_p$OR$^6$,
    c) (CH$_2$)$_p$NR$^6$R$^7$,
    d) halogen,
    e) CN,
  2) C$_{3\text{-}6}$ cycloalkyl,
  3) OR$^6$,
  4) SR$^{6a}$, S(O)R$^{6a}$, SO$_2$R$^{6a}$,
  5) —NR$^6$R$^7$, 6) 
  $$-\underset{\underset{O}{\|}}{\overset{R^6}{\underset{|}{N}}}\diagdown R^7,$$

7) 
  $$-\underset{\underset{O}{\|}}{\overset{R^6}{\underset{|}{N}}}\diagdown NR^7R^{7a},$$

8) 
  $$-O\diagdown\underset{O}{\overset{\|}{C}}\diagdown NR^6R^7,$$

-continued
  9) 
  $$-O\diagdown\underset{O}{\overset{\|}{C}}\diagdown OR^6,$$

10) 
  $$\diagdown\underset{O}{\overset{\|}{C}}\diagdown NR^6R^7,$$

11) —SO$_2$—NR$^6$R$^7$,

12) —$\underset{|}{\overset{R^6}{N}}$—SO$_2$—R$^{6a}$,

13) 
  $$\diagdown\underset{O}{\overset{\|}{C}}\diagdown R^6,$$

14) 
  $$\diagdown\underset{O}{\overset{\|}{C}}\diagdown OR^6,$$

15) N$_3$, or
  16) F; or

R$^2$ and R$^3$ are attached to the same C atom and are combined to form —(CH$_2$)$_u$- wherein one of the carbon atoms is optionally replaced by a moiety selected from: O, S(O)$_m$, —NC(O)—, and —N(COR$^{10}$)-;
R$^4$ is selected from H and CH$_3$;
and any two of R$^2$, R$^3$ and R$^4$ are optionally attached to the same carbon atom;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO,
e)

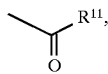

f) $-SO_2R^{11}$, or
g) $N(R^{10})_2$; or $R^6$ and $R^7$ may be joined in a ring;
$R^7$ and $R^{7a}$ may be joined in a ring;
$R^{6a}$ is selected from: $C_{1-4}$ alkyl, $C_{3-6}$ cycloalkyl, heterocycle, aryl, unsubstituted or substituted with:
a) $C_{1-4}$ alkoxy,
b) aryl or heterocycle,
c) halogen,
d) HO,
e)

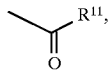

f) $-SO_2R^{11}$, or
g) $N(R^{10})_2$;

$R^8$ is independently selected from:
a) hydrogen,
b) aryl, heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NR^{10}-$, $(R^{10})_2NC(O)-$, $R^{10}_2N-C(NR^{10})-$, CN, $NO_2$, $R^{10}C(O)-$, $R^{10}OC(O)-$, $N_3$, $-N(R^{10})_2$, or $R^{11}OC(O)NR^{10}-$, and
c) $C_1-C_6$ alkyl unsubstituted or substituted by aryl, cyanophenyl, heterocycle, $C_3-C_{10}$ cycloalkyl, $C_2-C_6$ alkenyl, $C_2-C_6$ alkynyl, perfluoroalkyl, F, Cl, Br, $R^{10}O-$, $R^{11}S(O)_m-$, $R^{10}C(O)NH-$, $(R^{10})_2NC(O)-$, $R^{10}_2N-C(NR^{10})-$, CN, $R^{10}C(O)-$, $R^{10}OC(O)-$, $N_3$, $-N(R^{10})_2$, or $R^{10}C(O)NH-$;

$R^9$ is selected from:
a) hydrogen,
b) alkenyl, alkynyl, perfluoroalkyl, F, Cl, Br, $R^{10}O-$, $R^{11}S(O)_m-$, $R^{10}C(O)NR^{10}-$, $(R^{10})_2NC(O)-$, $R^{10}_2N-C(NR^{10})-$, CN, $NO_2$, $R^{10}C(O)-$, $R^{10}OC(O)-$, $N_3$, $-N(R^{10})_2$, or $R^{11}OC(O)NR^{10}-$, and
c) $C_1-C_6$ alkyl unsubstituted or substituted by perfluoroalkyl, F, Cl, Br, $R^{10}O-$, $R^{11}S(O)_m-$, $R^{10}C(O)NR^{10}-$, $(R^{10})_2NC(O)-$, $R^{10}_2N-C(NR^{10})-$, CN, $R^{10}C(O)-$, $R^{10}OC(O)-$, $N_3$, $-N(R^{10})_2$, or $R^{11}OC(O)NR^{10}-$;

$R^{10}$ is independently selected from hydrogen, $C_1-C_6$ alkyl, benzyl and aryl;
$R^{11}$ is independently selected from $C_1-C_6$ alkyl and aryl;
$A^1$ and $A^2$ are independently selected from: a bond, $-CH=CH-$, $-C\equiv C-$, $-C(O)-$, $-C(O)NR^{10}-$, $-NR^{10}C(O)-$, O, $-N(R^{10})-$, $-S(O)_2N(R^{10})-$, $-N(R^{10})S(O)_2-$, or $S(O)_m$;
G is $H_2$ or O;
V is selected from:
a) hydrogen,
b) heterocycle,
c) aryl,
d) $C_1-C_{20}$ alkyl wherein from 0 to 4 carbon atoms are replaced with a a heteroatom selected from O, S, and N, and
e) $C_2-C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;
X is $-CH_2-$, $-C(=O)-$, or $-S(=O)_m-$;
Z is a unsubstituted or substituted group selected from aryl, heteroaryl, arylmethyl, heteroarylmethyl, arylsulfonyl, heteroarylsulfonyl, wherein the substituted group is substituted with one or more of the following:
1) $C_{1-4}$ alkyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) $-S(O)_mR^{6a}$, or
g) $-C(O)NR^6R^7$,
2) aryl or heterocycle,
3) halogen,
4) $OR^6$,
5) $NR^6R^7$,
6) CN,
7) $NO_2$,
8) $CF_3$;
9) $-S(O)_mR^{6a}$,
10) $-C(O)NR^6R^7$, or
11) $C_3-C_6$ cycloalkyl;
m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;
t is 0 or 1; and
u is 4 or 5;

or the pharmaceutically acceptable salts thereof.

In a third embodiment of this invention, the inhibitors of farnesyl-protein transferase are illustrated by the formula C:

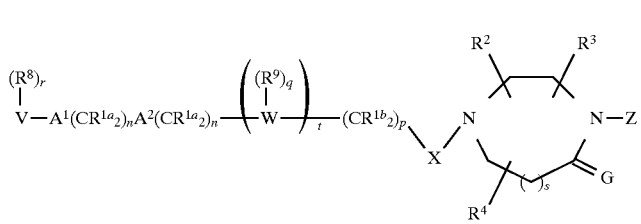

wherein:

$R^{1a}$ and $R^{1b}$ are independently selected from:
  a) hydrogen,
  b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$-, $R^{10}C(O)NR^{10}$-, $(R^{10})_2NC(O)$—, $R^{10}{}_2N$-$C(NR^{10})$—, CN, $NO_2$, $R^{10}C(O)$—, $R^{10}OC(O)$—, $N_3$, —$N(R^{10})_2$ or $R^{11}OC(O)NR^{10}$-,
  c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$-, $R^{10}C(O)NR^{10}$-, $(R^{10})_2NC(O)$—, $R^{10}{}_2N$-$C(NR^{10})$—, CN, $R^{10}C(O)$—, $R^{10}OC(O)$—, $N_3$, —$N(R^{10})_2$, and $R^{11}OC(O)$—$NR^{10}$-;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

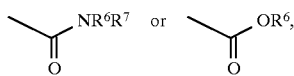

wherein the substituted group is substituted with one or more of:
  1) aryl or heterocycle, unsubstituted or substituted with:
    a) $C_{1-4}$ alkyl,
    b) $(CH_2)_pOR^6$,
    c) $(CH_2)_pNR^6R^7$,
    d) halogen,
    e) CN,
  2) $C_{3-6}$ cycloalkyl,
  3) $OR^6$,
  4) $SR^{6a}$, $S(O)R^{6a}$, $SO_2R^{6a}$,
  5) —$NR^6R^7$,
  6) 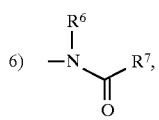
  7) 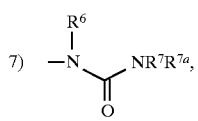
  8) 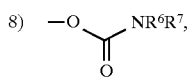
  9) 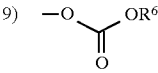
  10) 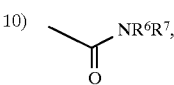
  11) —$SO_2$—$NR^6R^7$,
  12) 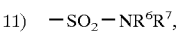
  13) 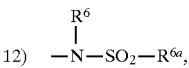
  14) 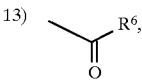
  15) $N_3$, or
  16) F; or $R^2$ and $R^3$ are attached to the same C atom and are combined to form —$(CH_2)_u$- wherein one of the carbon atoms is optionally replaced by a moiety selected from: O, $S(O)_m$, —NC(O)—, and —$N(COR^{10})$-;

$R^4$ is selected from H and $CH_3$;

and any two of $R^2$, $R^3$ and $R^4$ are optionally attached to the same carbon atom;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO,
  e) 
  f) —$SO_2R^{11}$, or
  g) $N(R^{10})_2$; or $R^6$ and $R^7$ may be joined in a ring;
$R^7$ and $R^{7a}$ may be joined in a ring;

$R^{6a}$ is selected from: $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO, e)

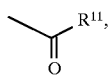

f) —$SO_2R^{11}$, or g) $N(R^{10})_2$;

$R^8$ is independently selected from:
a) hydrogen,
b) aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$-, $R^{10}C(O)NR^{10}$-, $(R^{10})_2NC(O)$—, $R^{10}{}_2N$-C$(NR^{10})$—, CN, $NO_2$, $R^{10}C(O)$—, $R^{10}OC(O)$—, $N_3$, —$N(R^{10})_2$, or $R^{11}OC(O)NR^{10}$-, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$-, $R^{10}C(O)NH$—, $(R^{10})_2NC(O)$—, $R^{10}{}_2N$-C$(NR^{10})$—, CN, $R^{10}C(O)$—, $R^{10}OC(O)$—, $N_3$, —$N(R^{10})_2$, or $R^{10}OC(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$-, $R^{10}C(O)NR^{10}$-, $(R^{10})_2NC(O)$—, $R^{10}{}_2N$-C$(NR^{10})$—, CN, $NO_2$, $R^{10}C(O)$—, $R^{10}OC(O)$—, $N_3$, —$N(R^{10})_2$, or $R^{11}OC(O)NR^{10}$-, and
c) $C_1$–$C_6$ alkyl unsubstituted or substituted by perfluoroalkyl, F, Cl, Br, $R^{10}O$—, $R^{11}S(O)_m$-, $R^{10}C(O)NR^{10}$-, $(R^{10})_2NC(O)$—, $R^{10}{}_2N$-C$(NR^{10})$—, CN, $R^{10}C(O)$—, $R^{10}OC(O)$—, $N_3$, —$N(R^{10})_2$, or $R^{11}OC(O)NR^{10}$-;

$R^{10}$ is independently selected from hydrogen, $C_1$–$C_6$ alkyl, benzyl and aryl;

$R^{11}$ is independently selected from $C_1$–$C_6$ alkyl and aryl;

$A^1$ and $A^2$ are independently selected from: a bond, —CH=CH—, —C≡C—, —C(O)—, —C(O)$NR^{10}$-, —$NR^{10}C(O)$—, O, —$N(R^{10})$—, —$S(O)_2N(R^{10})$—, —$N(R^{10})S(O)_2$-, or $S(O)_m$;

G is O;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is —$CH_2$-, —C(=O)—, or —$S(=O)_m$-;

Z is a unsubstituted or substituted group selected from aryl, heteroaryl, arylmethyl, heteroarylmethyl, arylsulfonyl, heteroarylsulfonyl, wherein the substituted group is substituted with one or more of the following:

1) $C_{1-4}$ alkyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) —$S(O)_mR^{6a}$, or
g) —$C(O)NR^6R^7$,
2) aryl or heterocycle,
3) halogen,
4) $OR^6$,
5) $NR^6R^7$,
6) CN,
7) $NO_2$,
8) $CF_3$;
9) —$S(O)_mR^{6a}$,
10) —$C(O)NR^6R^7$, or
11) $C_3$–$C_6$ cycloalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 1;
t is 0 or 1; and
u is 4 or 5;

or the pharmnaceutically acceptable salts thereof.

A preferred embodiment of the compounds of this invention is illustrated by the following formula:

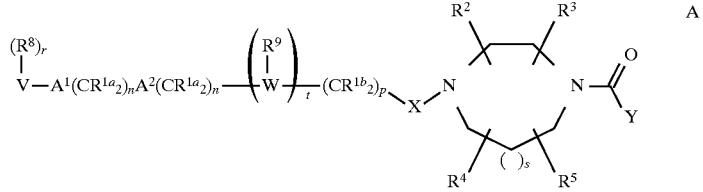

wherein:
$R^{1a}$ is independently selected from: hydrogen or $C_1$–$C_6$ alkyl;
$R^{1b}$ is independently selected from:
a) hydrogen,
b) aryl, heterocycle, cycloalkyl, $R^{10}O$—, —$N(R^{10})_2$ or $C_2$–$C_6$ alkenyl,
c) unsubstituted or substituted $C_1$–$C_6$ alkyl wherein the substitutent on the substituted $C_1$–$C_6$ alkyl is selected from unsubstituted or substituted aryl, heterocycle, cycloalkyl, alkenyl, $R^{10}O$— and —$N(R^{10})_2$;
$R^3$, $R^4$ and $R^5$ are independently selected from H and $CH_3$;
$R^2$ is H;

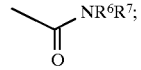

or $C_{1-5}$ alkyl, unbranched or branched, unsubstituted or substituted with one or more of:
1) aryl,
2) heterocycle, 3) OR$^6$,
4) SR$^{6a}$, SO$_2$R$^{6a}$, or
5)

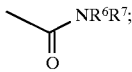

and any two of R$^2$, R$^3$, R$^4$, and R$^5$ are optionally attached to the same carbon atom;

R$^6$, R$^7$ and R$^{7a}$ are independently selected from:
H; C$_{1-4}$ alkyl, C$_{3-6}$ cycloalkyl, aryl, heterocycle, unsubstituted or substituted with:
  a) C$_{1-4}$ alkoxy,
  b) halogen, or
  c) aryl or heterocycle;

R$^{6a}$ is selected from:
C$_{1-4}$ alkyl or C$_{3-6}$ cycloalkyl, unsubstituted or substituted with:
  a) C$_{1-4}$ alkoxy,
  b) halogen, or
  c) aryl or heterocycle;

R$^8$ is independently selected from:
  a) hydrogen,
  b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$-, CN, NO$_2$, (R$^{10}$)$_2$N-C(NR$^{10}$)—, R$^{10}$C(O)—, R$^{10}$OC(O)—, —N(R$^{10}$)$_2$, or R$^{11}$OC(O)NR$^{10}$-, and
  c) C$_1$–C$_6$ alkyl substituted by C$_1$–C$_6$ perfluoroalkyl, R$^{10}$O—, R$^{10}$C(O)NR$^{10}$-, (R$^{10}$)$_2$N-C(NR$^{10}$)—, R$^{10}$C(O)—, R$^{10}$OC(O)—, —N(R$^{10}$)$_2$, or R$^{11}$OC(O)NR$^{10}$-;

R$^9$ is selected from:
  a) hydrogen,
  b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$-, R$^{10}$C(O)NR$^{10}$-, CN, NO$_2$, (R$^{10}$)$_2$N-C(NR$^{10}$)—, R$^{10}$C(O)—, R$^{10}$OC(O)—, —N(R$^{10}$)$_2$, or R$^{11}$OC(O)NR$^{10}$-, and
  c) C$_1$–C$_6$ alkyl unsubstituted or substituted by C$_1$–C$_6$ perfluoroalkyl, F, Cl, R$^{10}$O—, R$^{11}$S(O)$_m$-, R$^{10}$C(O)NR$^{10}$-, CN, (R$^{10}$)$_2$N-C(NR$^{10}$)—, R$^{10}$C(O)—, R$^{10}$OC (O)—, —N(R$^{10}$)$_2$, or R$^{11}$OC(O)NR$^{10}$-;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$-, O, —N(R$^{10}$)—, or S(O)$_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) C$_1$–C$_{20}$ alkyl wherein from 0 to 4 carbon atoms are replaced with a a heteroatom selected from O, S, and N, and
  e) C$_2$–C$_{20}$ alkenyl, and provided that V is not hydrogen if A$^1$ is S(O)$_m$ and V is not hydrogen if A$^1$ is a bond, n is 0 and A$^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

X is —CH$_2$- or —C(=O)—;

Y is mono- or bicyclic aryl, or mono- or bicyclic heterocycle, unsubstituted or substituted with one or more of:
  a) C$_{1-4}$ alkyl,
  b) C$_{1-4}$ alkoxy,
  c) halogen, or
  d) NR$^6$R$^7$;

m is 0, 1 or 2;
n is 0, 1, 2, 3 or 4;
p is 0, 1, 2, 3 or 4;
r is 0 to 5, provided that r is 0 when V is hydrogen;
s is 0 or 1; and
t is 0 or 1;

or the pharmaceutically acceptable salts thereof.

In a second preferred embodiment of this invention, the inhibitors of farnesyl-protein transferase are illustrated by the formula B:

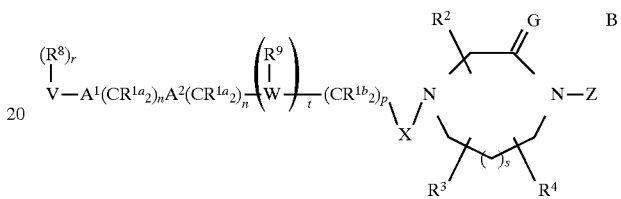

wherein:

R$^{1a}$ is independently selected from: hydrogen or C$_1$–C$_6$ alkyl;

R$^{1b}$ is independently selected from:
  a) hydrogen,
  b) aryl, heterocycle, cycloalkyl, R$^{10}$O—, —N(R$^{10}$)$_2$ or C$_2$–C$_6$ alkenyl,
  c) unsubstituted or substituted C$_1$–C$_6$ alkyl wherein the substitutent on the substituted C$_1$–C$_6$ alkyl is selected from unsubstituted or substituted aryl, heterocycle, cycloalkyl, alkenyl, R$^{10}$O— and —N(R$^{10}$)$_2$;

R$^3$ and R$^4$ are independently selected from H and CH$_3$;

R$^2$ is H;

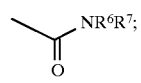

or C$_{1-5}$ alkyl, unbranched or branched, unsubstituted or substituted with one or more of:
1) aryl,
2) heterocycle,
3) OR$^6$,
4) SR$^{6a}$, SO$_2$R$^{6a}$, or
5)

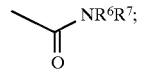

and any two of R$^2$, R$^3$, R$^4$, and R$^5$ are optionally attached to the same carbon atom;

R$^6$, R$^7$ and R$^{7a}$ are independently selected from:
H; C$_{1-4}$ alkyl, C$_{3-6}$ cycloalkyl, aryl, heterocycle, unsubstituted or substituted with:
  a) C$_{1-4}$ alkoxy,
  b) halogen, or
  c) aryl or heterocycle;

R$^{6a}$ is selected from:
C$_{1-4}$ alkyl or C$_{3-6}$ cycloalkyl, unsubstituted or substituted with:
  a) C$_{1-4}$ alkoxy, b) halogen, or
c) aryl or heterocycle;

R$^8$ is independently selected from:
a) hydrogen,
b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$-, CN, NO$_2$, (R$^{10}$)$_2$N-C(NR$^{10}$)—, R$^{10}$C(O)—, R$^{10}$OC(O)—, —N(R$^{10}$)$_2$, or R$^{11}$OC(O)NR$^{10}$-, and
c) C$_1$–C$_6$ alkyl substituted by C$_1$–C$_6$ perfluoroalkyl, R$^{10}$O—, R$^{10}$C(O)NR$^{10}$-, (R$^{10}$)$_2$N-C(NR$^{10}$)—, R$^{10}$C(O)—, R$^{10}$OC(O)—, —N(R$^{10}$)$_2$, or R$^{11}$OC(O)NR$^{10}$-;

R$^9$ is selected from:
a) hydrogen,
b) C$_2$–C$_6$ alkenyl, C$_2$–C$_6$ alkynyl, C$_1$–C$_6$ perfluoroalkyl, F, Cl, R$^{10}$O—, R$^{11}$S(O)$_m$-, R$^{10}$C(O)NR$^{10}$-, CN, NO$_2$, (R$^{10}$)$_2$N-C(NR$^{10}$)—, R$^{10}$C(O)—, R$^{10}$OC(O)—, —N(R$^{10}$)$_2$, or R$^{11}$OC(O)NR$^{10}$-, and
c) C$_1$–C$_6$ alkyl unsubstituted or substituted by C$_1$–C$_6$ perfluoroalkyl, F, Cl, R$^{10}$O—, R$^{11}$S(O)$_m$-, R$^{10}$C(O)NR$^{10}$-, CN, (R$^{10}$)$_2$N-C(NR$^{10}$)—, R$^{10}$C(O)—, R$^{10}$OC(O)—, —N(R$^{10}$)$_2$, or R$^{11}$OC(O)NR$^{10}$-;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$-, O, —N(R$^{10}$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) C$_1$–C$_{20}$ alkyl wherein from 0 to 4 carbon atoms are replaced with a a heteroatom selected from O, S, and N, and
e) C$_2$–C$_{20}$ alkenyl, and provided that V is not hydrogen if A$^1$ is S(O)$_m$ and V is not hydrogen if A$^1$ is a bond, n is 0 and A$^2$ is S(O)$_m$;

G is H$_2$ or O;

W is a heterocycle selected from pyrrolidinyl, imidazolyl, pyridinyl, thiazolyl, pyridonyl, 2-oxopiperidinyl, indolyl, quinolinyl, or isoquinolinyl;

X is —CH$_2$- or —C(=O)—;

Z is mono- or bicyclic aryl, mono- or bicyclic heteroaryl, mono- or bicyclic arylmethyl, mono- or bicyclic heteroarylmethyl, mono- or bicyclic arylsulfonyl, mono- or bicyclic heteroarylsulfonyl, unsubstituted or substituted with one or two of the following:
1) C$_{1-4}$ alkyl, unsubstituted or substituted with:
   a) C$_{1-4}$ alkoxy,
   b) NR$^6$R$^7$,
   c) C$_{3-6}$ cycloalkyl,
   d) aryl or heterocycle.
   e) HO,
   f) —S(O)$_m$R$^6$, or
   g) —C(O)NR$^6$R$^7$,
2) aryl or heterocycle,
3) halogen,
4) OR$^6$,
5) NR$^6$R$^7$,
6) CN,
7) NO$_2$,
8) CF$_3$;
9) —S(O)$_m$R$^6$,
10) —C(O)NR$^6$R$^7$, or
11) C$_3$–C$_6$ cycloalkyl;

m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 0 or 1; and
u is 4 or 5;

provided that when G is H$_2$ and W is imidazolyl, then the substitutent (R$^8$)$_r$- V—A$^1$(CR$^{1a}$$_2$)$_n$A$^2$(CR$^{1a}$$_2$)$_n$- is not H and provided that when X is —C(=O)—, or —S(=O)$_m$-, then t is 1 and the substitutent (R$^8$)$_r$- V—A$^1$(CR$^{1a}$$_2$)$_n$A$^2$(CR$^{1a}$$_2$)$_n$- is not H;

or the pharmaceutically acceptable salts thereof.

The preferred compounds of this invention are as follows:

2(S)-Butyl-1-(2,3-diaminoprop-1-yl)-4-(1-naphthoyl)piperazine 1-(3-Amino-2-(2-naphthylmethylamino)prop-1-yl)-2(S)-butyl-4-(1-naphthoyl)piperazine 2(S)-Butyl-1-{5-[1-(2-naphthylmethyl)]-4,5-dihydroimidazol}methyl-4-(1-naphthoyl)piperazine 1-[5-(1-Benzylimidazol)methyl]-2(S)-butyl-4-(1-naphthoyl)piperazine 1-{5-[1-(4-Nitrobenzyl)imidazolyl]methyl}-2(S)-butyl-4-(1-naphthoyl)piperazine 1-(3-Acetamidomethylthio-2(R)-aminoprop-1-yl)-2(S)-butyl-4-(1-naphthoyl)piperazine 2(S)-Butyl-1-[2-(1-imidazolyl)ethyl]sulfonyl-4-(1-naphthoyl)piperazine 2(R)-Butyl-1-imidazolyl-4-methyl-4-(1-naphthoyl)piperazine 2(S)-Butyl-4-(1-naphthoyl)-1-(3-pyridylmethyl)piperazine 1-2(S)-butyl-(2(R)-(4-nitrobenzyl)amino-3-hydroxypropyl)-4-(1-naphthoyl)piperazine 1-(2(R)-Amino-3-hydroxyheptadecyl)-2(S)-butyl-4-(1-naphthoyl)piperazine 2(S)-Benzyl-1-imidazolyl-4-methyl-4-(1-naphthoyl)piperazine 1-(2(R)-Amino-3-(3-benzylthio)propyl)-2(S)-butyl-4-(1-naphthoyl)piperazine 1-(2(R)-Amino-3-[3-(4-nitrobenzylthio)propyl]))-2(S)-butyl-4-(1-naphthoyl)piperazine 2(S)-Butyl-1-[(4-imidazolyl)ethyl]-4-(1-naphthoyl)piperazine 2(S)-Butyl-1-[(4-imidazolyl)methyl]-4-(1-naphthoyl)piperazine 2(S)-Butyl-1-[(1-naphth-2-ylmethyl)-1H-imidazol-5-yl)acetyl]-4-(1-naphthoyl)piperazine 2(S)-Butyl-1-[(1-naphth-2-ylmethyl)-1H-imidazol-5-yl)ethyl]-4-(1-naphthoyl)piperazine 1-(2(R)-Amino-3-hydroypropyl)-2(S)-butyl-4-(1-naphthoyl)piperazine 1-(2(R)-Amino-4-hydroxybutyl)-2(S)-butyl-4-(1-naphthoyl)piperazine 1-(2-Amino-3-(2-benzyloxyphenyl)propyl)-2(S)-butyl-4-(1-naphthoyl)piperazine 1-(2-Amino-3-(2-hydroxyphenyl)propyl)-2(S)-butyl-4-(1-naphthoyl)piperazine 1-[3-(4-imidazolyl)propyl]-2(S)-butyl-4-(1-naphthoyl)piperazine 2(S)-n-Butyl-4-(1-naphthoyl)-1-[1-(1-naphthylmethyl)imidazol-5-ylmethyl]-piperazine 2(S)-n-Butyl-4-(1-naphthoyl)-1-[1-(2-naphthylmethyl)imidazol-5-ylmethyl]-piperazine 2(S)-n-Butyl-1-[1-(4-cyanobenzyl)imidazol-5-ylmethyl]-4-(1-naphthoyl)piperazine
2(S)-n-Butyl-1-[1-(4-methoxybenzyl)imidazol-5-ylmethyl]-4-(1-naphthoyl)piperazine
2(S)-n-Butyl-1-[1-(3-methyl-2-butenyl)imidazol-5-ylmethyl]-4-(1-naphthoyl)piperazine
2(S)-n-Butyl-1-[1-(4-fluorobenzyl)imidazol-5-ylmethyl]-4-(1-naphthoyl)piperazine
2(S)-n-Butyl-1-[1-(4-chlorobenzyl)imidazol-5-ylmethyl]-4-(1-naphthoyl)piperazine
1-[1-(4-Bromobenzyl)imidazol-5-ylmethyl]-2(S)-n-butyl-4-(1-naphthoyl)piperazine
1-[1-(4-Bromobenzyl)imidazol-5-ylmethyl]-2(S)-n-butyl-4-(1-naphthoyl)piperazine
2(S)-n-Butyl-4-(1-naphthoyl)-1-[1-(4-trinfluoromethylbenzyl)imidazol-5-ylmethyl]-piperazine
2(S)-n-Butyl-1-[1-(4-methylbenzyl)imidazol-5-ylmethyl]-4-(1-naphthoyl)-piperazine
2(S)-n-Butyl-1-[1-(3-methylbenzyl)imidazol-5-ylmethyl]-4-(1-naphthoyl)-piperazine
1-[1-(4-Phenylbenzyl)imidazol-5-ylmethyl]-2(S)-n-butyl-4-(1-naphthoyl)-piperazine
2(S)-n-Butyl-4-(1-naphthoyl)-1-[1-(2-phenylethyl)imidazol-5-ylmethyl]-piperazine
2(S)-n-Butyl-4-(1-naphthoyl)-1-[1-(4-trifluoromethoxy)-imidazol-5-ylmethyl]piperazine
1-{[1-(4-cyanobenzyl)-1H-imidazol-5-yl]acetyl}-2(S)-n-butyl-4-(1-naphthoyl)piperazine
5(S)-n-Butyl-1-(2,3-dimethylphenyl)-4-(4-imidazolylmethyl)-piperazin-2-one
5(S)-n-Butyl-4-[1-(4-cyanobenzyl)imidazol-5-ylmethyl]-1-(2,3-dimethylphenyl)piperazin-2-one
4-[1-(4-Cyanobenzyl)imidazol-5-ylmethyl]-1-(2,3-dimethylphenyl)-5(S)-(2-methoxyethyl)piperazin-2-one
(S)-1-(3-Chlorophenyl)-4-[1-(4-cyanobenzyl)-5-imidazolylmethyl]-5-[2-(methanesulfonyl)ethyl]-2-piperazinone
(S)-1-(3-Chlorophenyl)-4-[1-(4-cyanobenzyl)-5-imidazolylmethyl]-5-[2-(ethanesulfonyl)ethyl]-2-piperazinone
(R)-1-(3-Chlorophenyl)-4-[1-(4-cyanobenzyl)-5-imidazolylmethyl]-5-[2-(ethanesulfonyl)methyl]-2-piperazinone
(S)-1-(3-Chlorophenyl)-4-[1-(4-cyanobenzyl)-5-imidazolylmethyl]-5-[N-ethyl-2-acetamido]-2-piperazinone
(±)-5-(2-Butynyl)-1-(3-chlorophenyl)-4-[1-(4-cyanobenzyl)-5-imidazolylmethyl]-2-piperazinone
1-(3-Chlorophenyl)-4-[1-(4-cyanobenzyl)-5-imidazolylmethyl]-2-piperazinone
5(S)-Butyl-4-[1-(4-cyanobenzyl-2-methyl)-5-imidazolylmethyl]-1-(2,3-dimethylphenyl)-piperazin-2-one
4-[1-(2-(4-Cyanophenyl)-2-propyl)-5-imidazolylmethyl]-1-(3-chlorophenyl)-5(S)-(2-methylsulfonylethyl)piperazin-2-one
5(S)-n-Butyl-4-[1-(4-cyanobenzyl)-5-imidazolylmethyl]-1-(2-methylphenyl)piperazin-2-one
4-[1-(4-Cyanobenzyl)-5-imidazolylmethyl]-5(S)-(2-fluoroethyl)-1-(3-chlorophenyl)piperazin-2-one
4-[3-(4-Cyanobenzyl)pyridin-4-yl]-1-(3-chlorophenyl)-5(S)-(2-methylsulfonylethyl)-piperazin-2-one
4-[5-(4-Cyanobenzyl)-1-imidazolylethyl]-1-(3-chlorophenyl)piperazin-2-one.
or the pharmaceutically acceptable salts thereof.
Specific examples of the compounds of the invention are:
1-{5-[1-(4-Nitrobenzyl)imidazolyl]methyl}-2(S)-n-butyl-4-(1-naphthoyl)piperazine

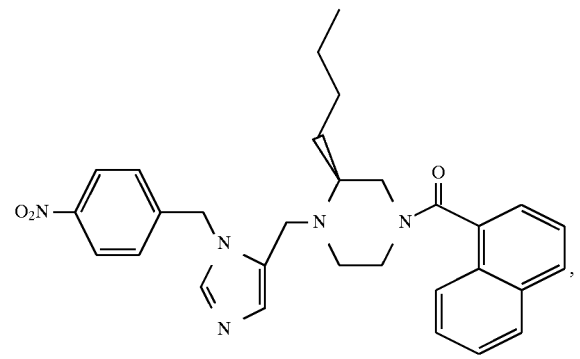

1-[5-(1-Benzylimidazol)methyl]-2(S)-butyl-4-(1-naphthoyl)piperazine

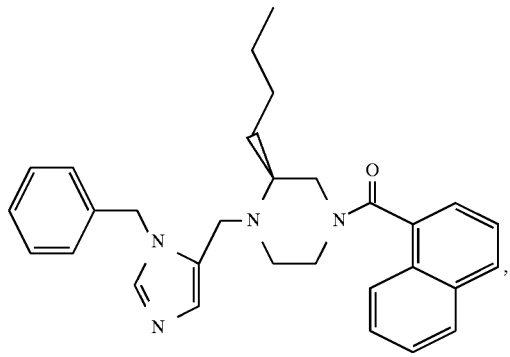

1-(2(R)-Amino-3-(3-benzylthio)propyl)-2(S)-butyl-4-(1-naphthoyl)piperazine

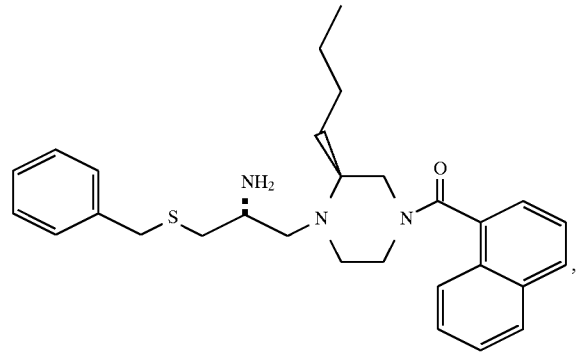

1-(2(R)-Amino-3-[3-(4-nitrobenzylthio)propyl])-2(S)-butyl-4-(1-naphthoyl)piperazine

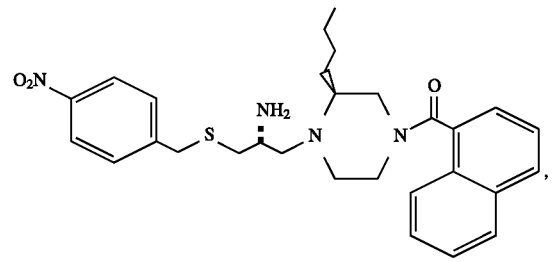

2(S)-n-Butyl-1-[1-(4-cyanobenzyl)imidazol-5-ylmethyl]-4-(1-naphthoyl)piperazine

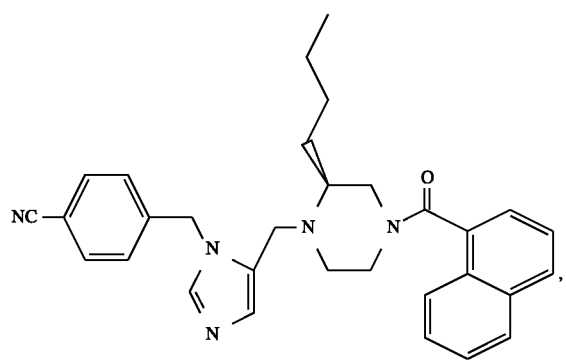

2(S)-n-Butyl-1-[1-(4-cyanobenzyl)imidazol-5-ylmethyl]-4-(2,3-dimethylphenyl)piperazin-5-one

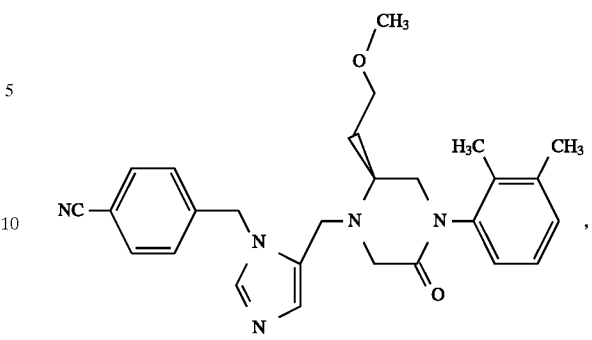

5(S)-n-Butyl-4-[1-(4-cyanobenzyl)-5-imidazolylmethyl]-1-(2-methylphenyl)piperazin-2-one

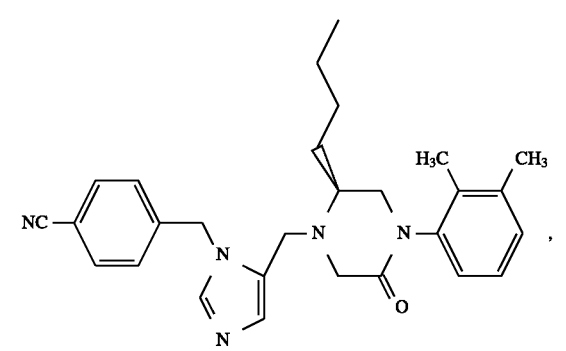

2(S)-n-Butyl-1-[1-(4-chlorobenzyl)imidazol-5-ylmethyl]-4-(1-naphthoyl)piperazine

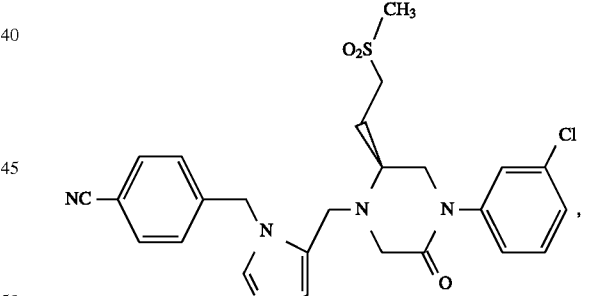

(S)-1-(3-Chlorophenyl)-4-[1-(4-cyanobenzyl)-5-imidazolylmethyl]-5-[2-(methanesulfonyl)ethyl]-2-piperazinone

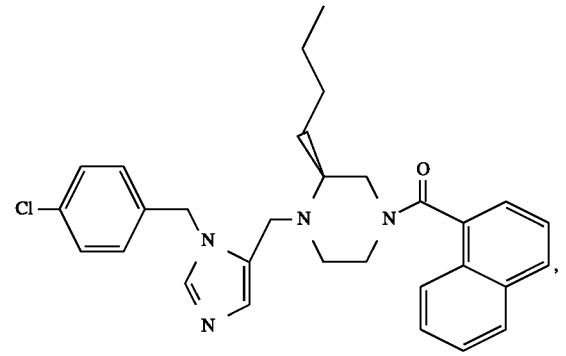

1-{[1-(4-Cyanobenzyl)-1H-imidazol-5-yl]acetyl}-2(S)-n-butyl-4-(1-naphthoyl)piperazine

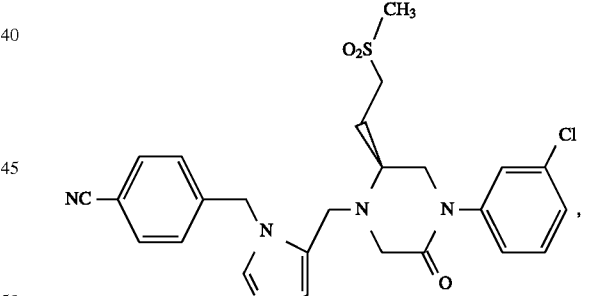

(S)-1-(3-Chlorophenyl)-4-[1-(4-cyanobetizyl)-5-imidazolylmethyl]-5-[2-(ethanesulfonyl)ethyl]-2-piperazinone

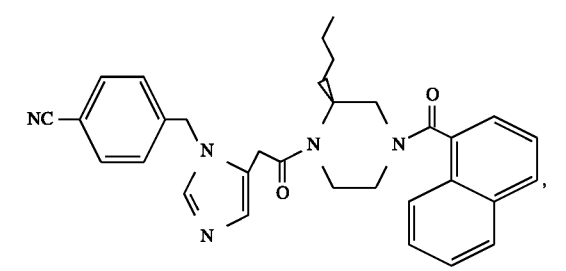

1-[1-(4-Cyanobenzyl)imidazol-5-ylmethyl]-4-(2,3-dimethylphenyl)-2(S)-(2-methoxyethyl)piperazin-5-one

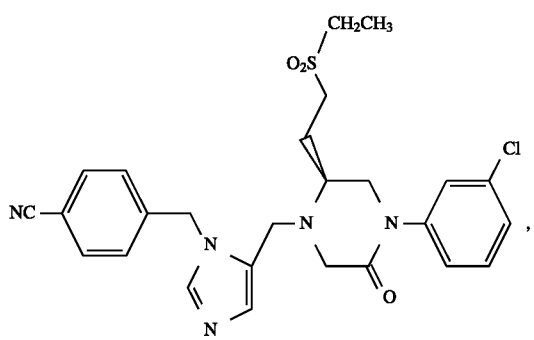

(R)-1-(3-Chlorophenyl)-4-[1-(4-cyanobenzyl)-5-imidazolylmethyl]-5-[2-(ethanesulfonyl)methyl]-2-piperazinone

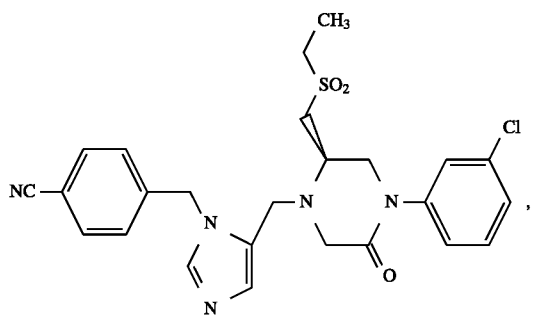

1-(3-Chlorophenyl)-4-[1-(4-cyanobenzyl)-5-imidazolylmethyl]-2-piperazinone

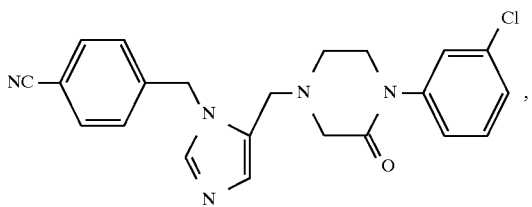

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphtliyl, indanyl, or biphenyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^2$ and $R^3$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substitutent(s) $R^2$ and $R^3$ are selected.

As used herein in the definition of $R^6$, $R^7$ and $R^{7a}$, the substituted $C_{1-8}$ alkyl, substituted $C_{3-6}$ alkenyl, substituted aroyl, substituted aryl, substituted heteroaroyl, substituted arylsulfonyl, substituted heteroarylsulfonyl and substituted heterocycle include moieties containing from 1 to 3 substitutents in addition to the point of attachment to the rest of the compound.

When $R^2$ and $R^3$ are combined to form $—(CH_2)_u-$, cyclic moieties are formed. Examples of such cyclic moieties include, but are not limited to:

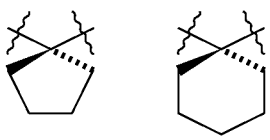

In addition, such cyclic moieties may optionally include a heteroatom(s). Examples of such heteroatom-containing cyclic moieties include, but are not limited to:

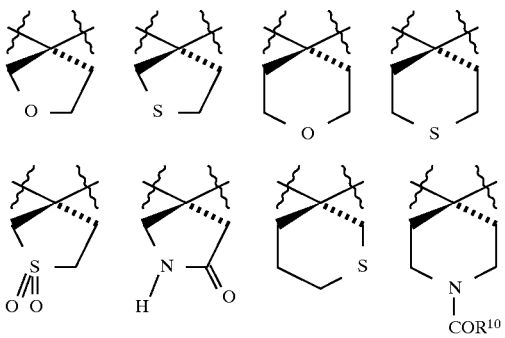

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, $-N(R^{10})_2$, $R^{10}C(O)NR^{10}$- or unsubstituted or substituted $C_1$–$C_6$ alkyl wherein the substituent on the substituted $C_1$–$C_6$ alkyl is selected from unsubstituted or substituted phenyl, $-N(R^{10})_2$, $R^{10}O$— and $R^{10}C(O)NR^{10}$-.

Preferably, $R^2$ is selected from: H,

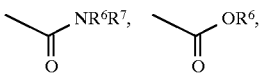

and an unsubstituted or substituted group, the group selected from $C_{1-8}$ alkyl, $C_{2-8}$ alkenyl and $C_{2-8}$ alkynyl;

wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
2) $C_{3-6}$ cycloalkyl,
3) $OR^6$,
4) $SR^{6a}$, $S(O)R^{6a}$, $SO_2R^{6a}$,

5) $-NR^6R^7$,

6) 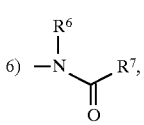

7) 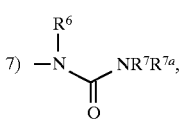

8) 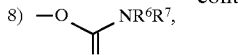

9) 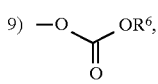

10) 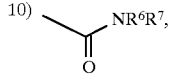

11) $-SO_2-NR^6R^7$,

12) 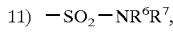

13) 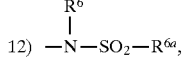

14) 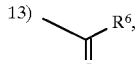

15) $N_3$, or
16) F.

Preferably, $R^3$ is selected from: hydrogen and $C_1$–$C_6$ alkyl.

Preferably, $R^4$ and $R^5$ are hydrogen.

Preferably, $R^6$, $R^7$ and $R^{7a}$ is selected from: hydrogen, unsubstituted or substituted $C_1$–$C_6$ alkyl, unsubstituted or substituted aryl and unsubstituted or substituted cycloalkyl.

Preferably, $R^{6a}$ is unsubstituted or substituted $C_1$–$C_6$ alkyl, unsubstituted or substituted aryl and unsubstituted or substituted cycloalkyl.

Preferably, $R^9$ is hydrogen or methyl. Most preferably, $R^a$ is hydrogen.

Preferably, $R^{10}$ is selected from H, $C_1$–$C_6$ alkyl and benzyl.

Preferably, $A^1$ and $A^2$ are independently selected from: a bond, $-C(O)NR^{10}$-, $-NR^{10}C(O)$—, O, $-N(R^{10})$—, $-S(O)_2N(R^{10})$- and $-N(R^{10})S(O)_2$-.

Preferably, V is selected from hydrogen, heterocycle and aryl. More preferably, V is phenyl.

Preferably, Y is selected from unsubstituted or substituted phenyl, unsubstituted or substituted naphthyl, unsubstituted or substituted pyridyl, unsubstituted or substituted furanyl and unsubstituted or substituted thienyl. More preferably, Y is unsubstituted or substituted phenyl.

Preferably, Z is selected from unsubstituted or substituted phenyl, unsubstituted or substituted naphthyl, unsubstituted or substituted pyridyl, unsubstituted or substituted furanyl and unsubstituted or substituted thienyl. More preferably, Y is unsubstituted or substituted phenyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, n and r are independently 0, 1, or 2.
Preferably p is 1, 2 or 3.
Preferably s is 0.
Preferably t is 1.

Preferably, in compounds of the formula B, when G is $H_2$ and W is imidazolyl, then the substitutent $(R^8)_r$- V—$A^1$ $(CR^{1a}_2)_nA^2(CR^{1a}_2)_n$- is not H.

Preferably, in compounds of the formula B, when X is $-C(=O)$—, or $-S(=O)_m$-, then t is 1 and the substitutent $(R^8)_r$- V—$A^1(CR^{1a}_2)_nA^2(CR^{1a}_2)_n$- is not H;

It is intended that the definition of any substituent or variable (e.g., $R^{1a}$, $R^9$, n, etc.) at a particular location in a molecule be independent of its definitions elsewhere in that molecule. Thus, —N($R^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–22, in addition to other standard manipulations such as ester hydrolysis, cleavage of protecting groups, etc., as may be known in the literature or exemplified in the experimental procedures. Substituents R, $R^a$ and $R^b$, as shown in the Schemes, represent the substituents $R^2$, $R^3$, $R^4$, and $R^5$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Schemes.

Synoplsis of Schemes 1–16:

The requisite intermediates are in some cases commercially available, or can be prepared according to literature procedures, for the most part. In Scheme 1, for example, the synthesis of 2-alkyl substituted piperazines is outlined, and is essentially that described by J. S. Kiely and S. R. Priebe in *Organic Preparations and Proceedings Int.*, 1990, 22, 761–768. Boc-protected amino acids I, available commercially or by procedures known to those skilled in the art, can be coupled to N-benzyl amino acid esters using a variety of dehydrating agents such as DCC (dicyclohexycarbodiimide) or EDC.HCl (1-ethyl-3-(3-dimethylaminopropyl) carbodiimide hydrochloride) in a solvent such as methylene chloride, chloroform, dichloroethane, or in dimethylformamide. The product II is then deprotected with acid, for example hydrogen chloride in chloroform or ethyl acetate, or trifluoroacetic acid in methylene chloride, and cyclized under weakly basic conditions to give the diketopiperazine III. Reduction of III with lithium aluminum hydride in refluxing ether gives the piperazine IV, which is protected as the Boc derivative V. The N-benzyl group can be cleaved under standard conditions of hydrogenation, e.g., 10% palladium on carbon at 60 psi hydrogen on a Parr apparatus for 24–48 h. The product VI can be treated with an acid chloride, or a carboxylic acid under standard dehydrating conditions to furnish the carboxamides VII; a final acid deprotection as previously described gives the intermediate VIII (Scheme 2). The intermediate VIII can be reductively alkylated with a variety of aldehydes, such as IX. The aldehydes can be prepared by standard procedures, such as that described by O. P. Goel, U. Krolls, M. Stier and S. Kesten in *Organic Syntheses*, 1988, 67, 69–75, from the appropriate amino acid (Scheme 3). The reductive alkylation can be accomplished at pH 5–7 with a variety of reducing agents, such as sodium triacetoxyborohydride or sodium cyanoborohydride in a solvent such as dichloroethane, methanol or dimethylformamide. The product X can be deprotected to give the final compounds XI with trifluoroacetic acid in methylene chloride. The final product XI is isolated in the salt form, for example, as a trifluoroacetate, hydrochloride or acetate salt, among others. The product diamine XI can further be selectively protected to obtain XII, which can subsequently be reductively alkylated with a second aldehyde to obtain XIII. Removal of the protecting group, and conversion to cyclized products such as the dihydroimidazole XV can be accomplished by literature procedures.

Alternatively, the protected piperazine intermediate VII can be reductively alkylated with other aldehydes such as 1-trityl-4-imidazolyl-carboxaldehyde or 1-trityl-4-imidazolylacetaldehyde, to give products such as XVI (Scheme IV). The trityl protecting group can be removed from XVI to give XVII, or alternatively, XVI can first be treated with an alkyl halide then subsequently deprotected to give the alkylated imidazole XVIII. Alternatively, the intermediate VIII can be acylated or sulfonylated by standard techniques. The imidazole acetic acid XIX can be converted to the acetate XXI by standard procedures, and XXI can be first reacted with an alkyl halide, then treated with refluxing methanol to provide the regiospecifically alkylated imidazole acetic acid ester XXII. Hydrolysis and reaction with piperazine VIII in the presence of condensing reagents such as 1-(3-dimethylaminopropyl)-3-ethylcarbodiimide (EDC) leads to acylated products such as XXIV.

If the piperazine VIII is reductively alkylated with an aldehyde which also has a protected hydroxyl group, such as XXV in Scheme 6, the protecting groups can be subsequently removed to unmask the hydroxyl group (Schemes 6, 7). The alcohol can be oxidized under standard conditions to e.g. an aldehyde, which can then be reacted with a variety of organometallic reagents such as Grignard reagents, to obtain secondary alcohols such as XXIX. In addition, the fully deprotected amino alcohol XXX can be reductively alkylated (under conditions described previously) with a variety of aldehydes to obtain secondary amines, such as XXXI (Scheme 7), or tertiary amines.

The Boc protected amino alcohol XXVII can also be utilized to synthesize 2-aziridinylmethylpiperazines such as XXXII (Scheme 8). Treating XXVII with 1,1'-sulfonyldiimidazole and sodium hydride in a solvent such as dimethylformamide led to the formation of aziridine XXXII. The aziridine reacted in the presence of a nucleophile, such as a thiol, in the presence of base to yield the ring-opened product XXXIII.

In addition, the piperazine VIII can be reacted with aldehydes derived from amino acids such as O-alkylated tyrosines, according to standard procedures, to obtain compounds such as XXXIX. When R' is an aryl group, XXXIX can first be hydrogenated to unmask the phenol, and the amine group deprotected with acid to produce XL. Alternatively, the amine protecting group in XXXIX can be removed, and O-alkylated phenolic amines such as XLI produced.

Depending on the identity of the amino acid I, various side chains can be incorporated into the piperazine. For example when I is the Boc-protected β-benzyl ester of aspartic acid, the intermediate diketopiperazine XLII where n=1 and R=benzyl is obtained, as shown in Scheme 10. Subsequent lithium aluminum hydride reduction reduces the ester to the alcohol XLIII, which can then be reacted with a variety of alkylating agents such as an alkyl iodide, under basic conditions, for example, sodium hydride in dimethylformamide or tetrahydrofuran. The resulting ether XLIV can then be carried on to final products as described in Schemes 3–9.

N-Aryl piperazines can be prepared as described in Scheme 11. An aryl amine XLV is reacted with bis-chloroethyl amine hydrochloride (XLVI) in refluxing n-butanol to furnish compounds XLVII. The resulting piperazines XLVII can then be carried on to final products as described in Schemes 3–9.

Piperazin-5-ones can be prepared as shown in Scheme 12. Reductive amination of Boc-protected amino aldehydes XLIX (prepared from I as described previously) gives rise to compound L. This is then reacted with bromoacetyl bromide under Schotten-Baumann conditions; ring closure is effected with a base such as sodium hydride in a polar aprotic solvent such as dimethylformamide to give LI. The carbamate protecting group is removed under acidic conditions such as trifluoroacetic acid in methylene chloride, or hydrogen chloride gas in methanol or ethyl acetate, and the resulting piperazine can then be carried on to final products as described in Schemes 3–9.

The isomeric piperazin-3-ones can be prepared as described in Scheme 13. The imine formed from arylcarboxamides LII and 2-aminoglycinal diethyl acetal (LIII) can be reduced under a variety of conditions, including sodium triacetoxyborohydride in dichloroethane, to give the amine LIV. Amino acids I can be coupled to amines LIV under standard conditions, and the resulting amide LV when treated with aqueous acid in tetrahydrofuran can cyclize to the unsaturated LVI. Catalytic hydrogenation under standard conditions gives the requisite intermediate LVII, which is elaborated to final products as described in Schemes 3–9.

Access to alternatively substituted piperazines is described in Scheme 14. Following deprotection with trifluoroacetic acid, the N-benzyl piperazine V can be acylated with an aryl carboxylic acid. The resulting N-benzyl aryl carboxamide LIX can be hydrogenated in the presence of a catalyst to give the piperazine carboxamide LX which can then be carried on to final products as described in Schemes 3–9.

Reaction Scheme 15 provides an illustrative example the synthesis of compounds of the instant invention wherein the substituents $R^2$ and $R^3$ are combined to form —$(CH_2)_u$-. For example, 1-aminocyclohexane-1-carboxylic acid LXI can be converted to the spiropiperazine LXVI essentially according to the procedures outlined in Schemes 1 and 2. The piperazine intermediate LXIX can be deprotected as before, and carried on to final products as described in Schemes 3–9. It is understood that reagents utilized to provide the substituent Y which is 2-(naphthyl) and the imidazolylalkyl substituent may be readily replaced by other reagents well known in the art and readily available to provide other N-substituents on the piperazine.

The aldehyde XLIX from Scheme 12 can also be reductively alkylated with an aniline as shown in Scheme 16. The product LXXI can be converted to a piperazinone by acylation with chloroacetyl chloride to give LXXII, followed by base-induced cyclization to LXXIII. Deprotection, followed by reductive alkylation with a protected imidazole carboxaldehyde leads to LXXV, which can be alkylation with an arylmethylhalide to give the imidazolium salt LXXVI. Final removal of protecting groups by either solvolysis with a lower alkyl alcohol, such as methanol, or treatment with triethylsilane in methylene chloride in the presence of trifluoroacetic acid gives the final product LXXVII.

Scheme 17 illustrates the use of an optionally substituted homoserine lactone LXXIX to prepare a Boc-protected piperazinone LXXXII. Intermediate LXXXII may be deprotected and reductively alkylated or acylated as illustrated in the previous Schemes. Alternatively, the hydroxyl moiety of intermediate LXXXII may be mesylated and displaced by a suitable nucleophile, such as the sodium salt of ethane thiol, to provide an intermediate LXXXIII. Intermediate LXXXII may also be oxidized to provide the carboxylic acid on intermediate LXXXIV, which can be utilized form an ester or amide moiety.

Amino acids of the general formula LXXXVI which have a sidechain not found in natural amino acids may be prepared by the reactions illustrated in Scheme 18 starting with the readily prepared imine LXXXV.

Schemes 19–22 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

SCHEME 1

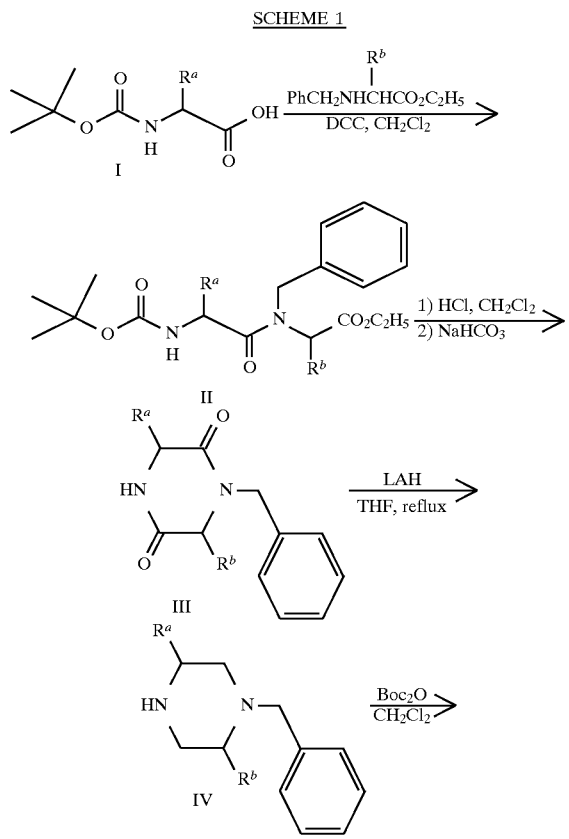

31
-continued
SCHEME 1
32
-continued
SCHEME 2
SCHEME 2
SCHEME 3
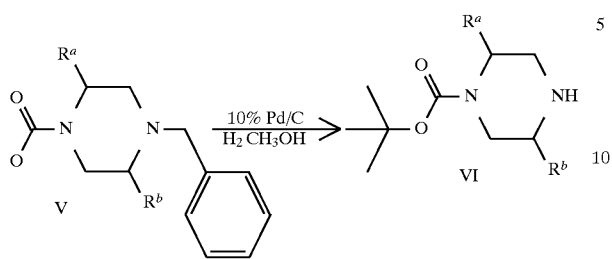

-continued
SCHEME 3
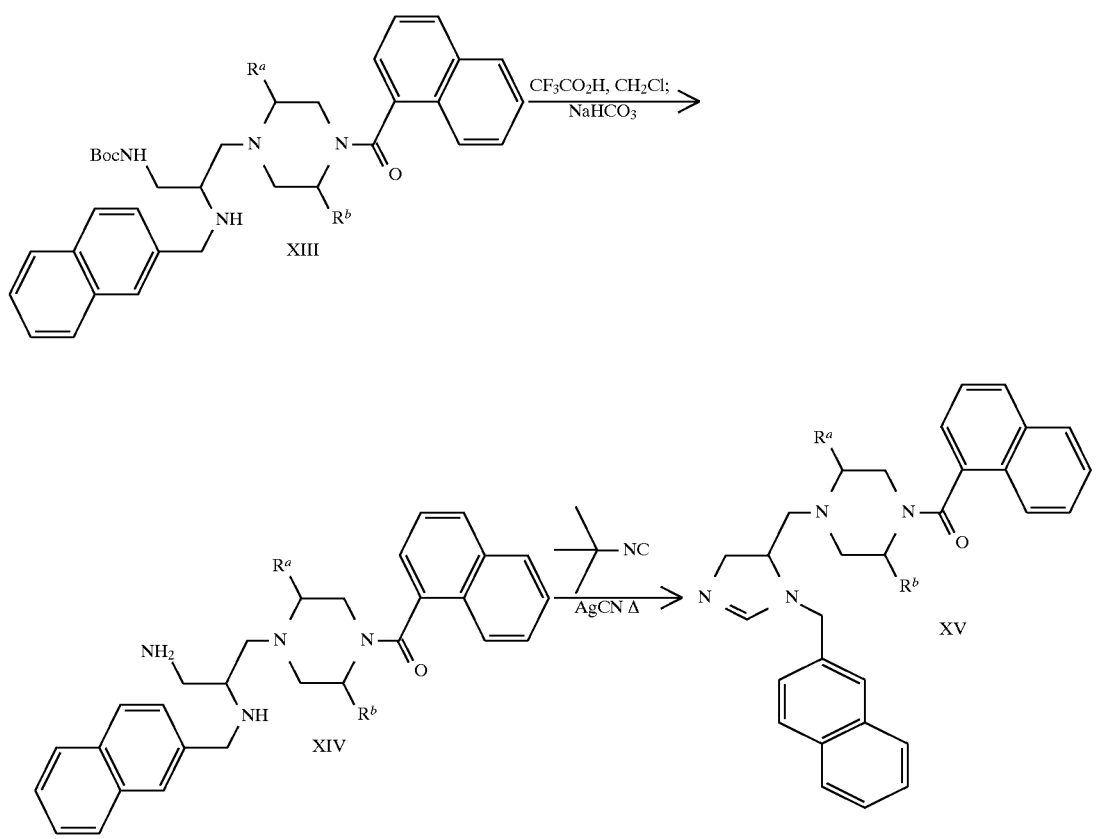
SCHEME 4
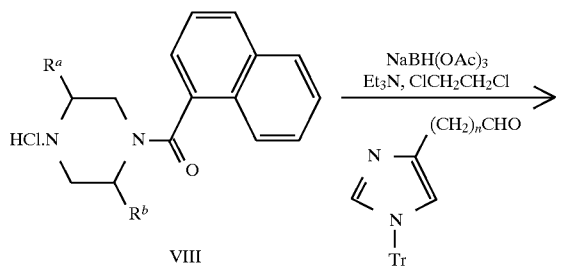

-continued
SCHEME 4
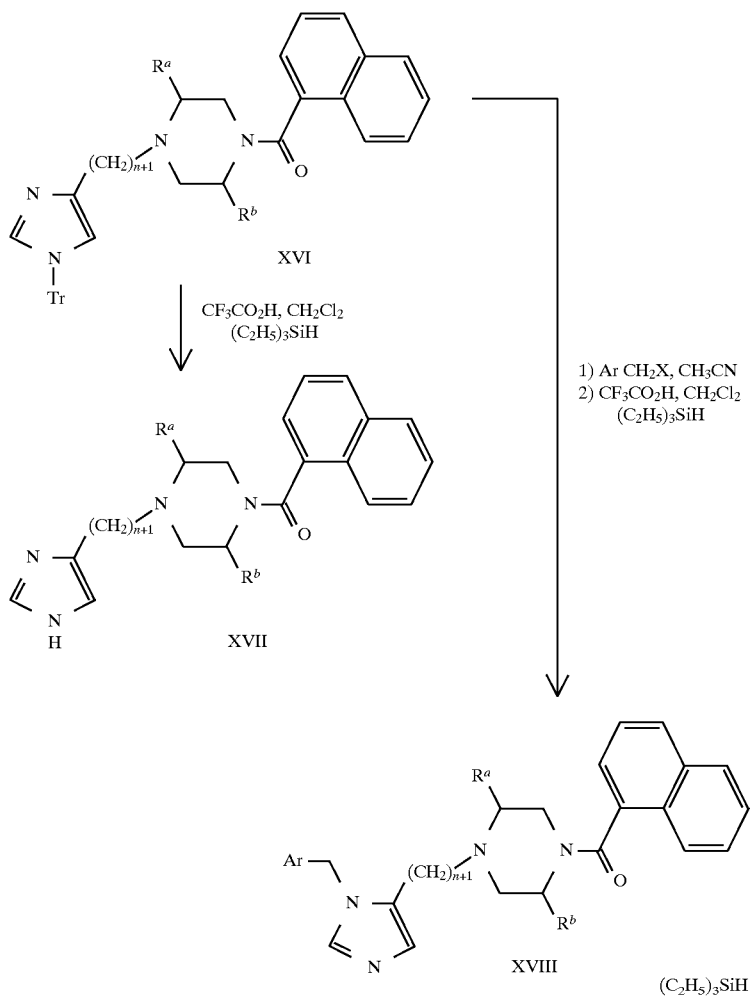
SCHEME 5
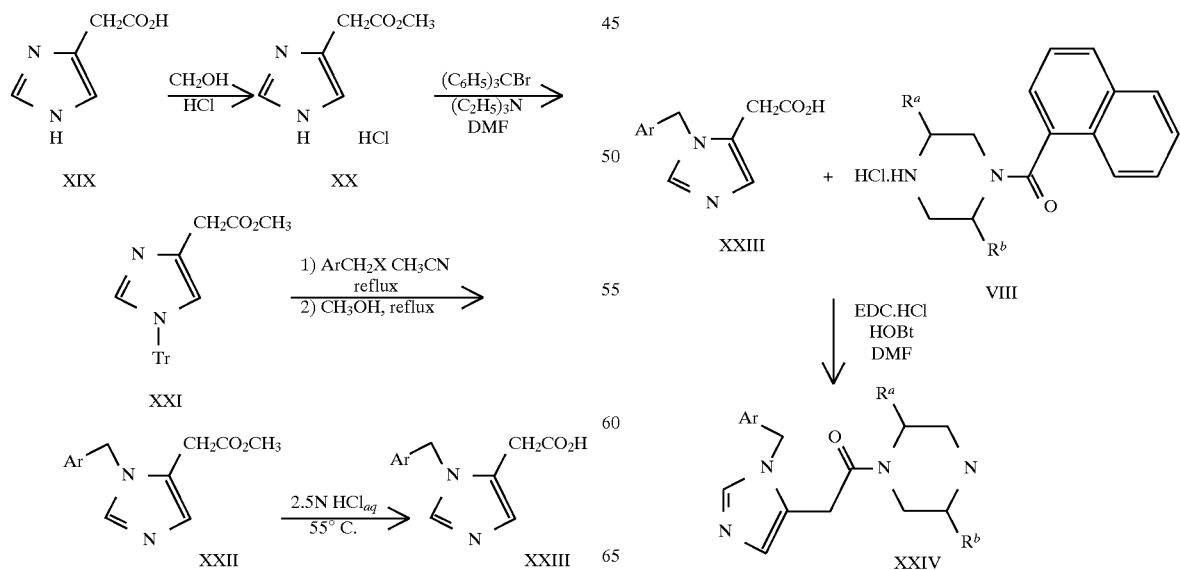

SCHEME 6
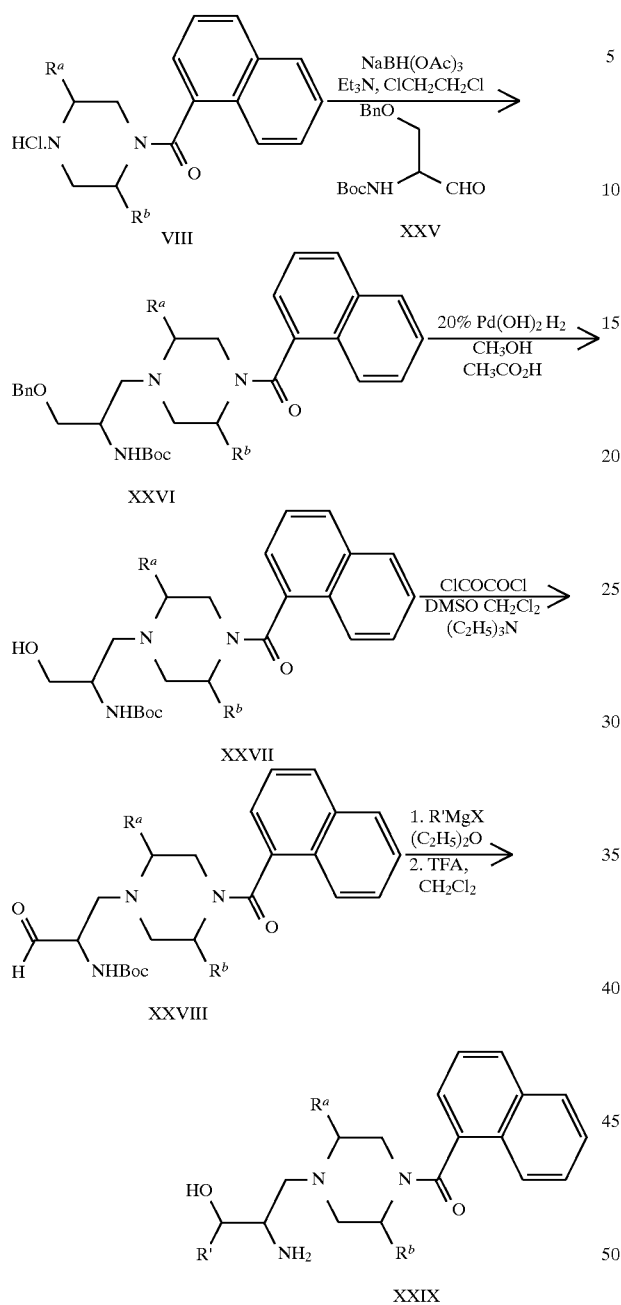
SCHEME 7
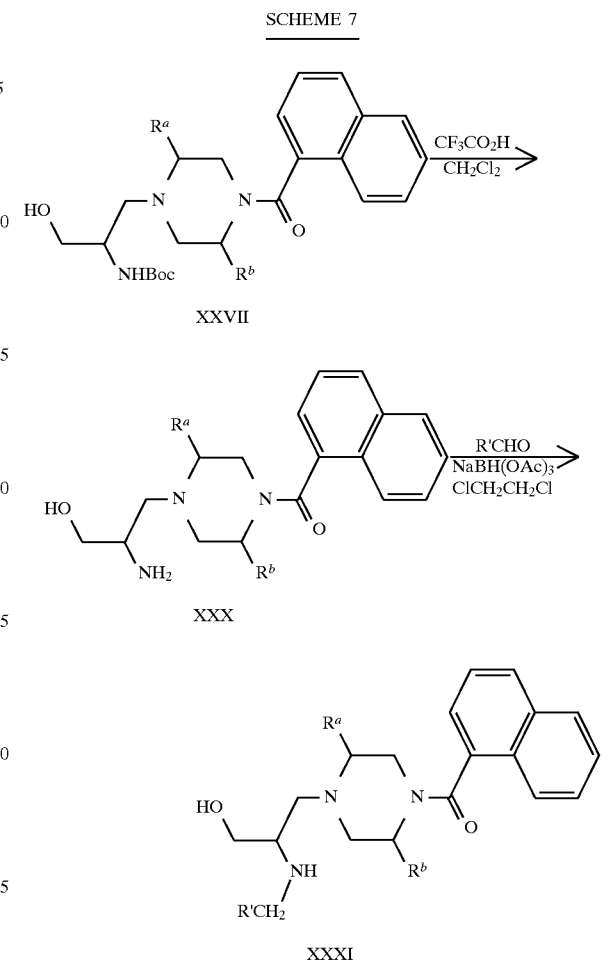

SCHEME 8
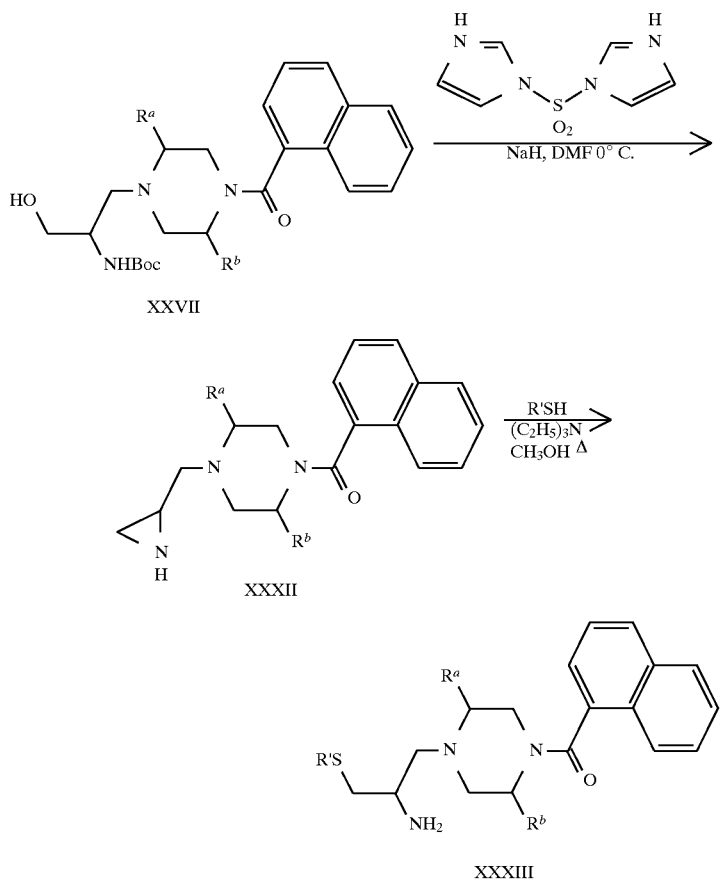
SCHEME 9
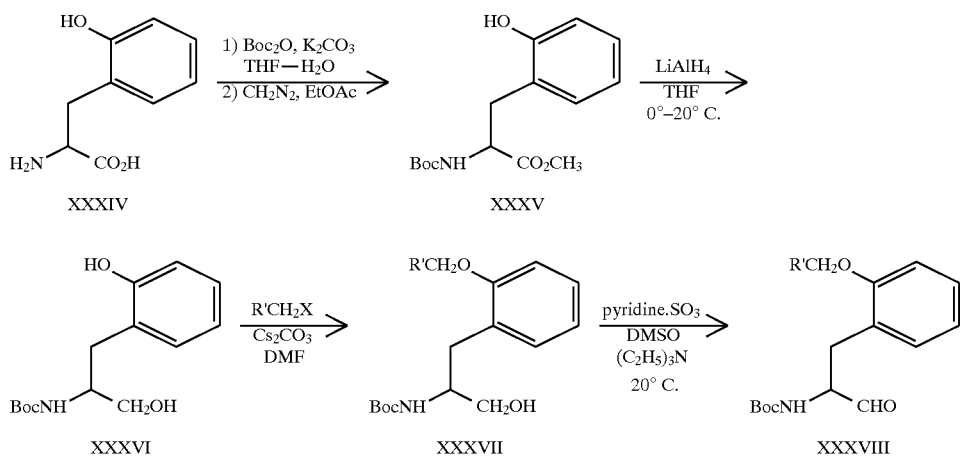

-continued
SCHEME 9
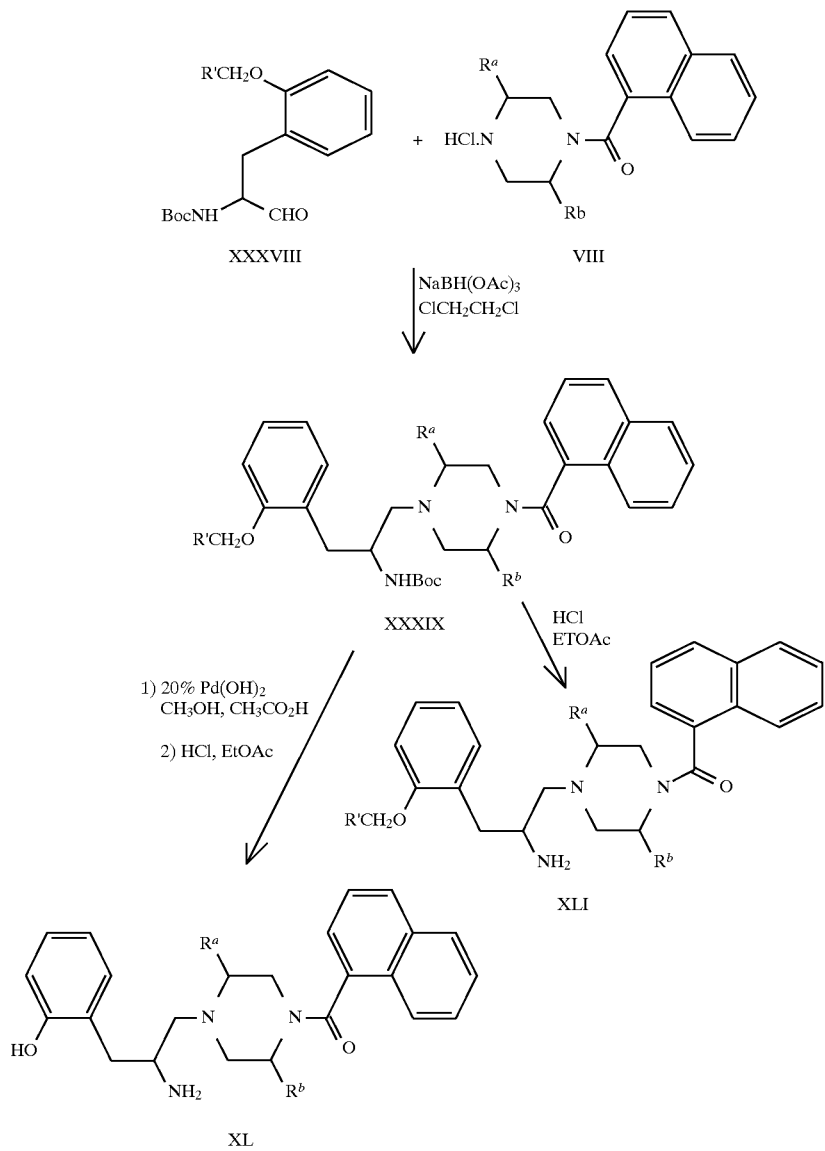
SCHEME 10
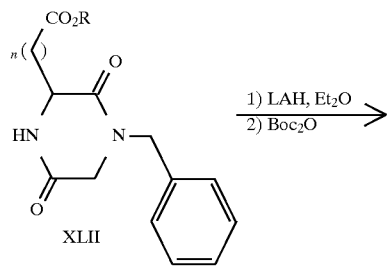
-continued
SCHEME 10
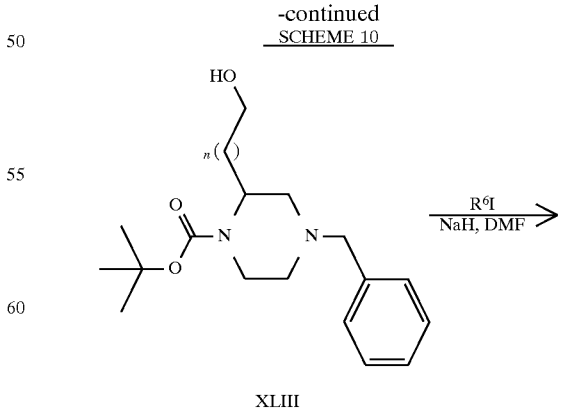

-continued
SCHEME 10
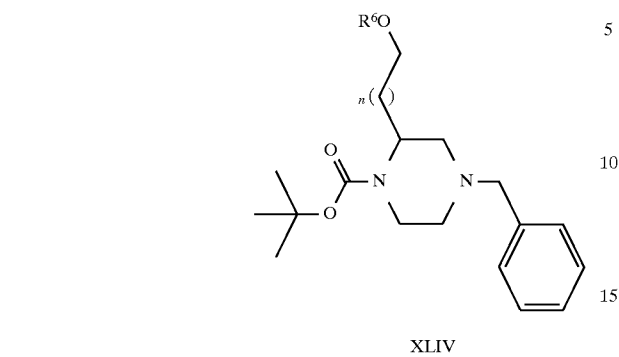
XLIV
SCHEME 11
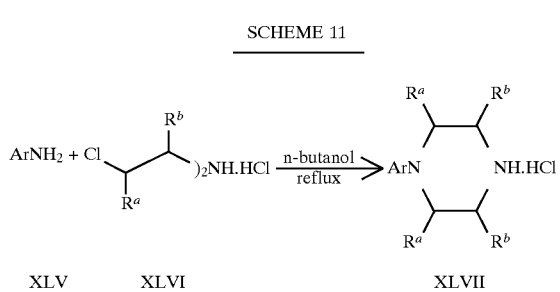
XLV    XLVI                XLVII
SCHEME 12
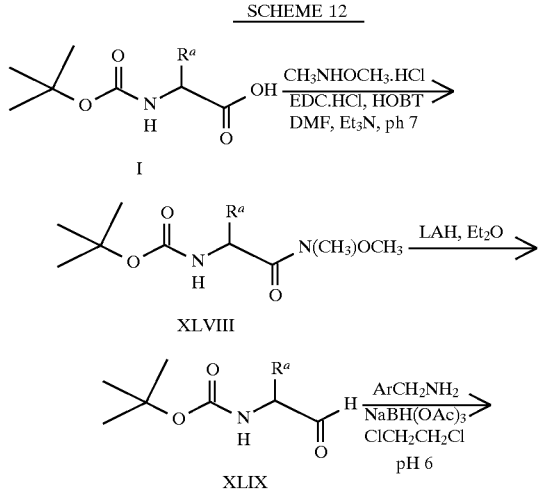
I
XLVIII
XLIX
L
LI
SCHEME 12
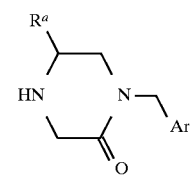
SCHEME 13
ArCHO + NH$_2$CH$_2$CH(OC$_2$H$_5$)$_2$ $\xrightarrow{\text{NaBH(OAc)}_3}$
LII           LIII
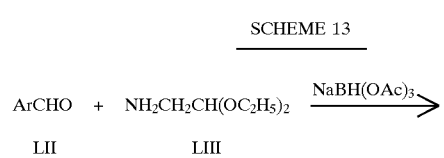
LIV
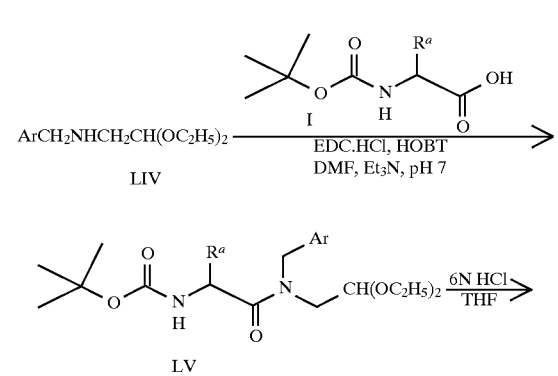
LV
LVI
LVII
SCHEME 14
V $\xrightarrow[\text{2) NaHCO}_3]{\text{1) CF}_3\text{CO}_2\text{H, CH}_2\text{Cl}_2}$
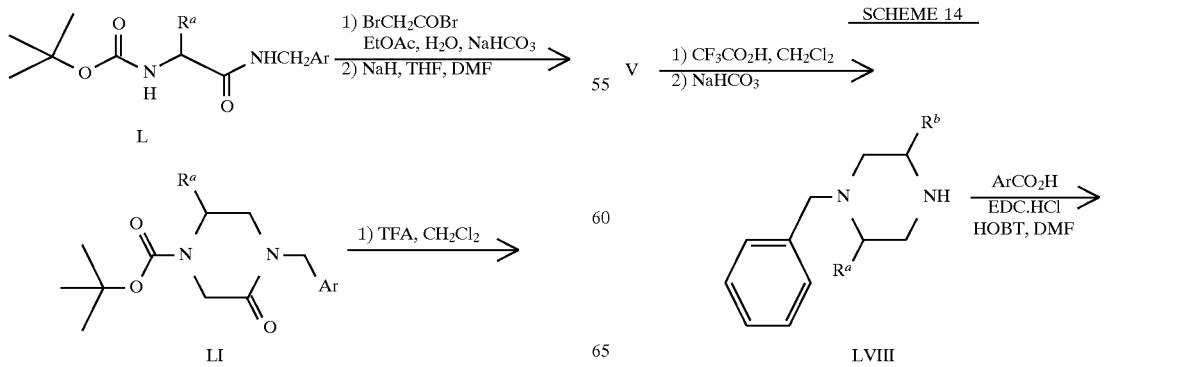
LVIII -continued
SCHEME 14
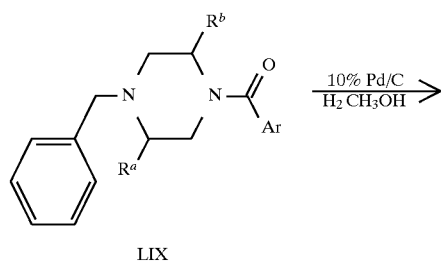
LIX
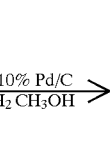
LX
SCHEME 15
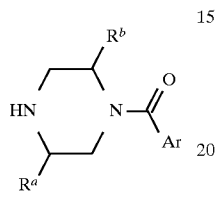
LXI
LXII
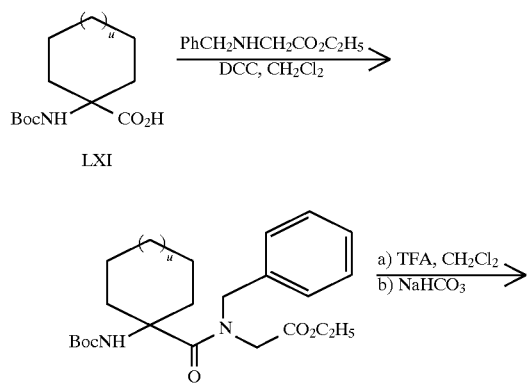
LXIII
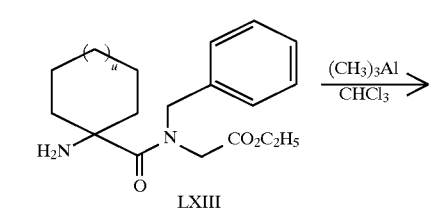
LXIV
-continued
SCHEME 15
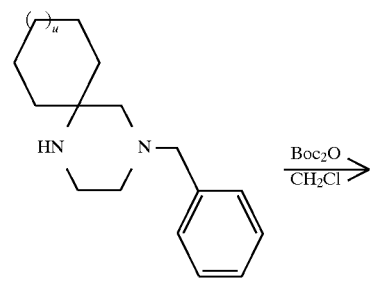
LXV
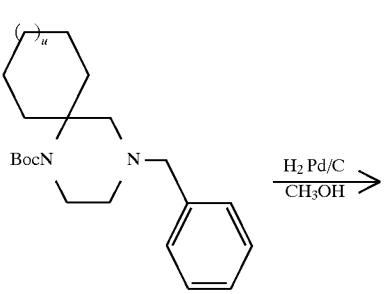
LXVI
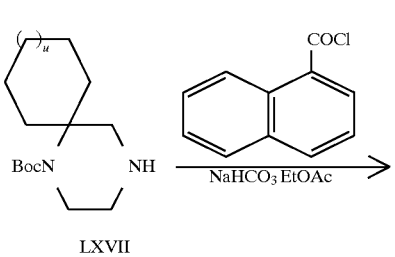
LXVII
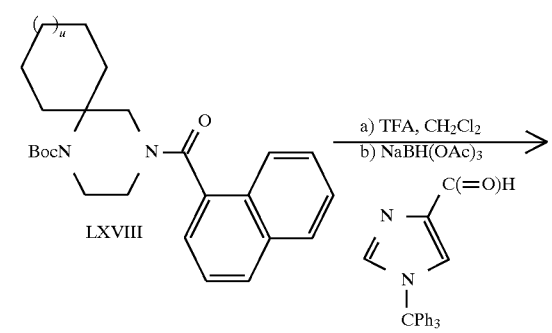
LXVIII
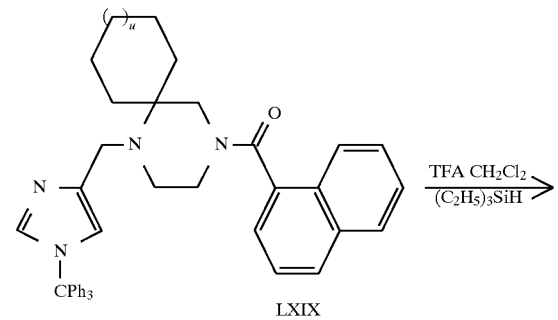
LXIX -continued
SCHEME 15
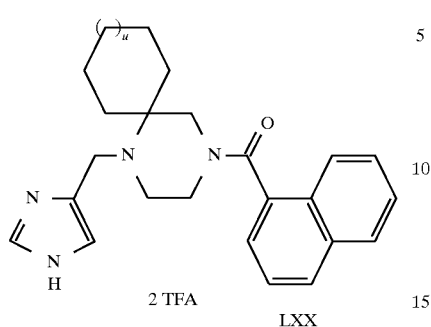
SCHEME 16
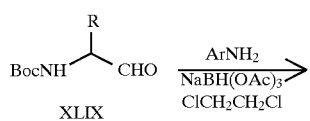
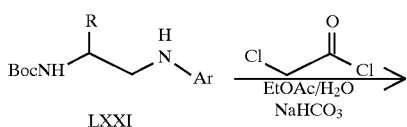
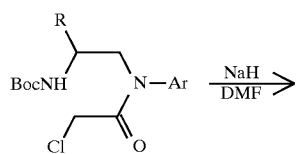
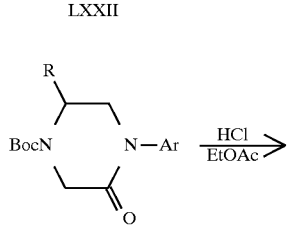
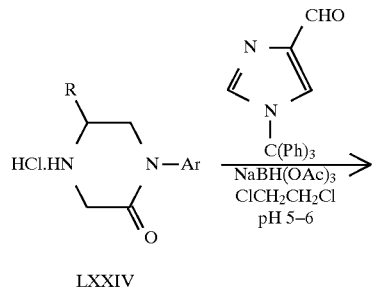
-continued
SCHEME 16
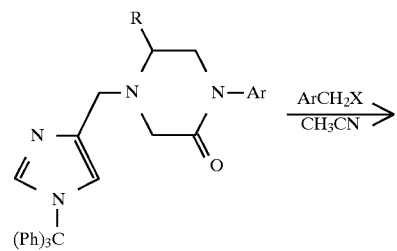
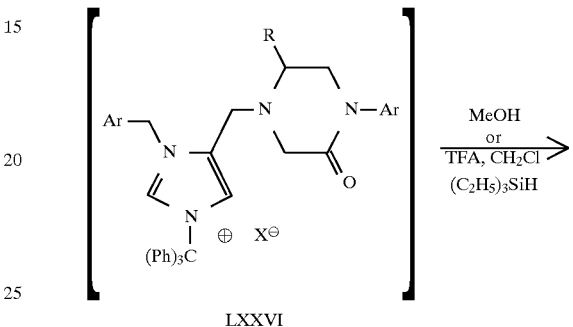
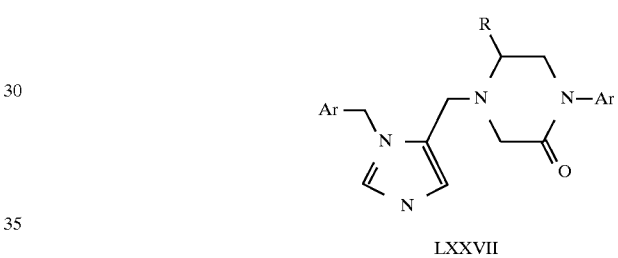
SCHEME 17
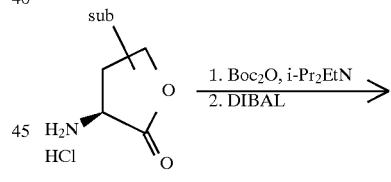
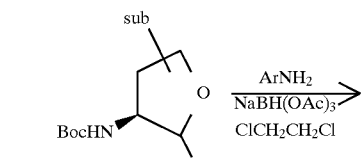
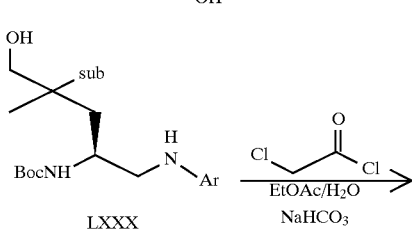

49
-continued
SCHEME 17
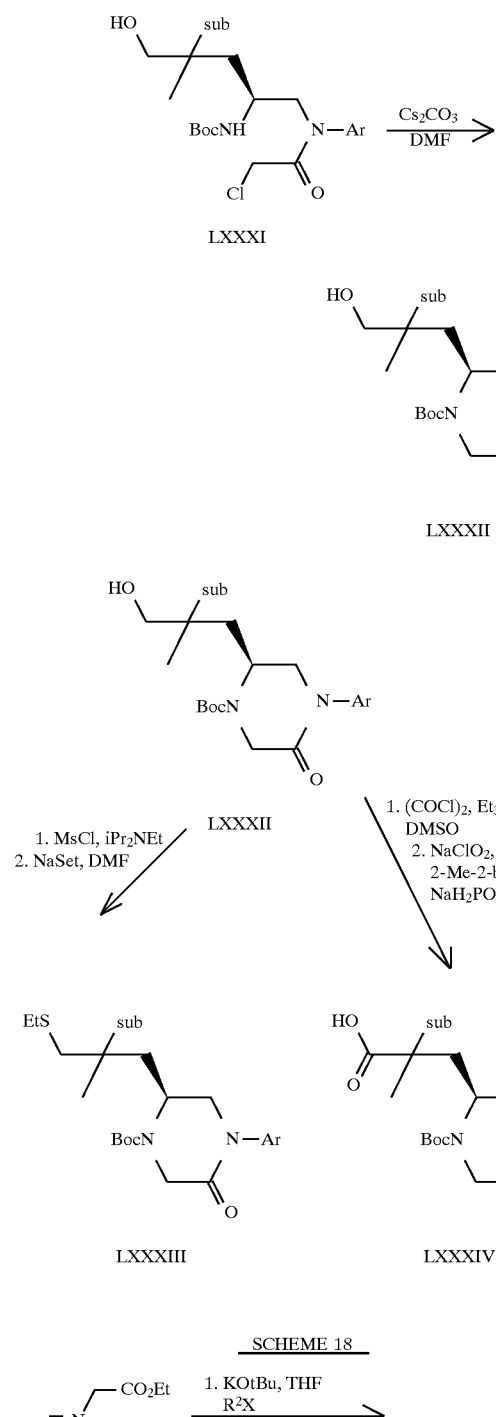
SCHEME 18
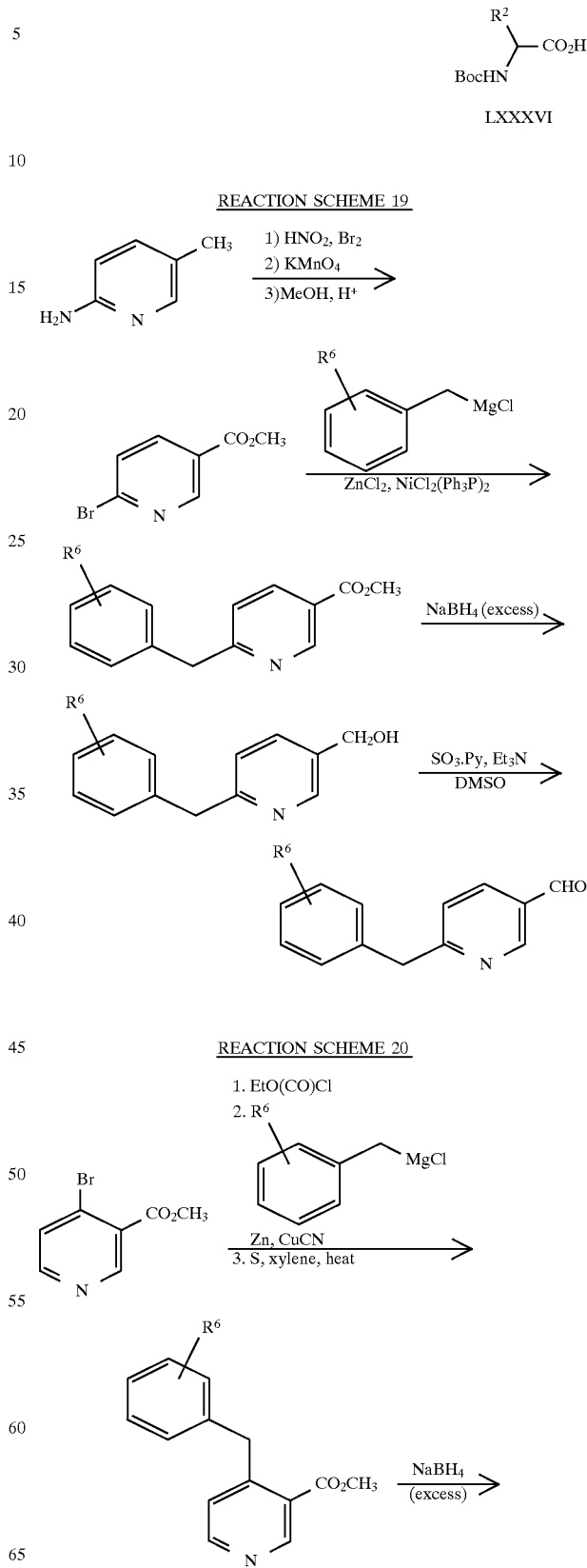
50
-continued
SCHEME 18
REACTION SCHEME 19
REACTION SCHEME 20

51
-continued
REACTION SCHEME 20
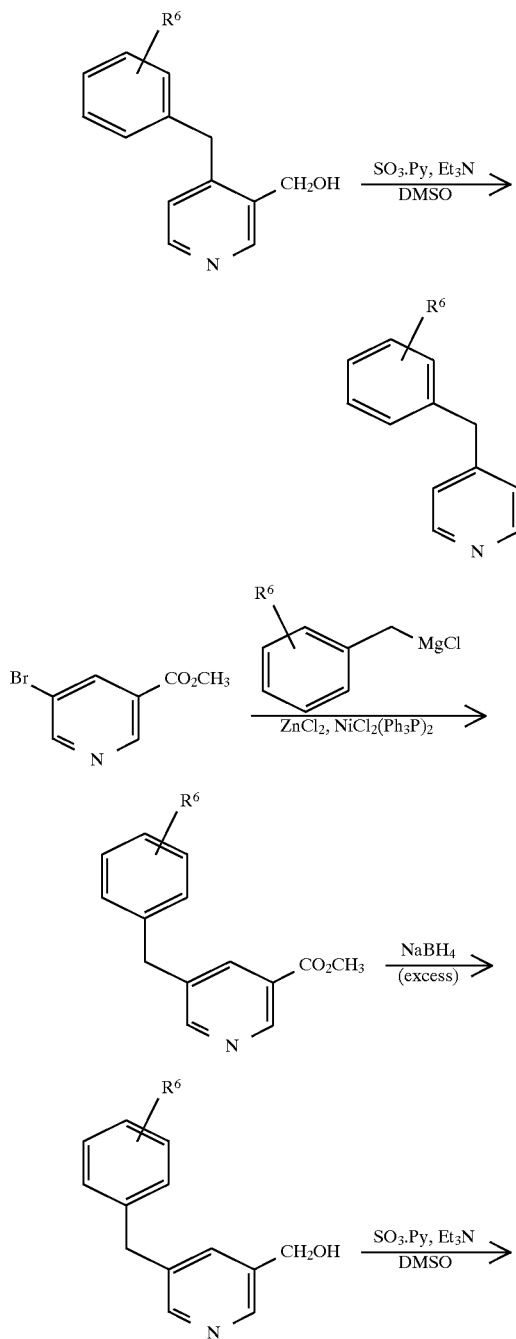
52
REACTION SCHEME 21
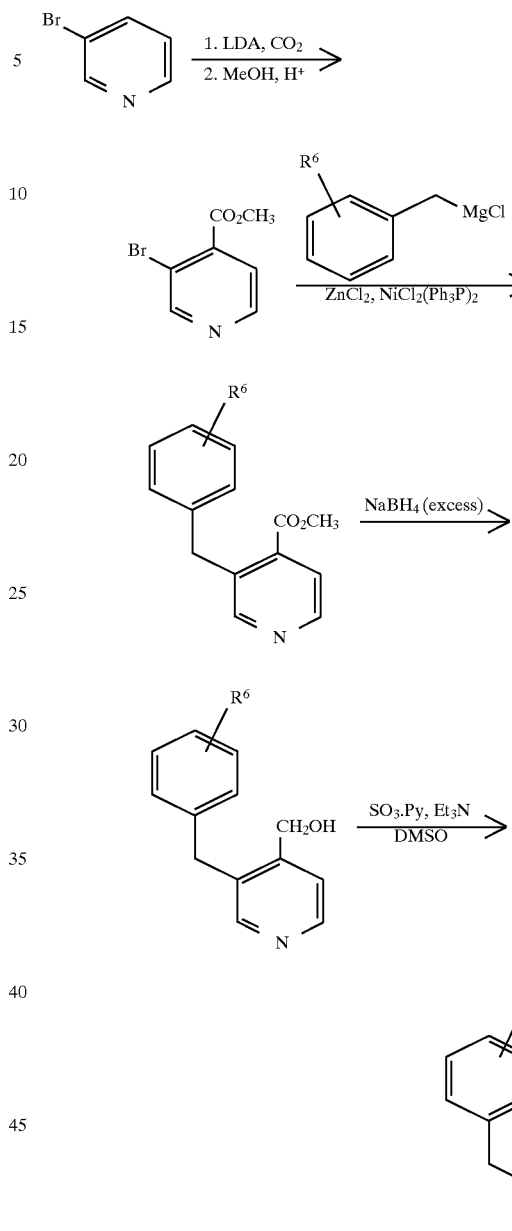
REACTION SCHEME 22
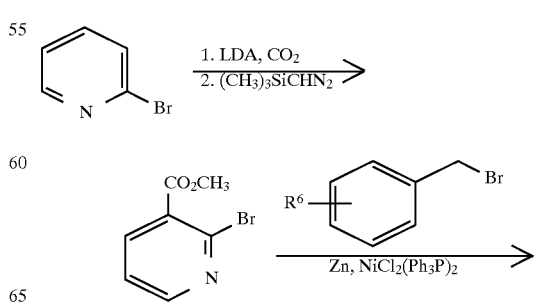

-continued
REACTION SCHEME 22

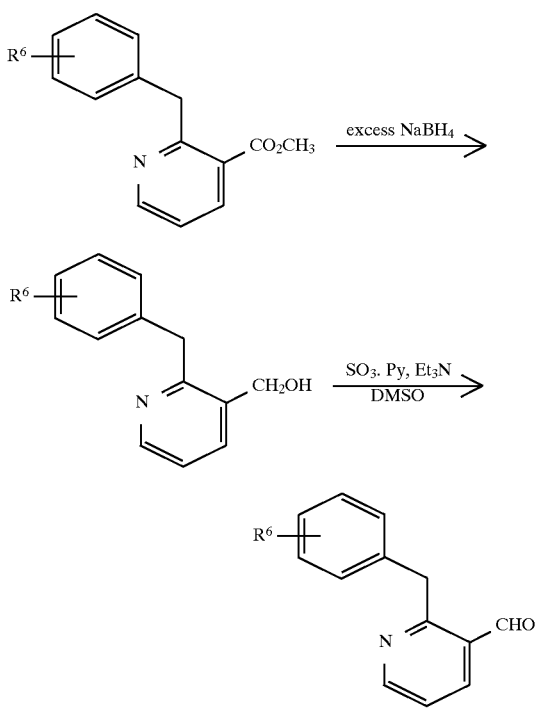

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof. Purification by HPLC was accomplished with a 40×100 mm Waters PrepPak® reverse phase HPLC column (Delta-Pak™ $C_{18}$ 15 μm, 100 Å). Gradient elution employed 0.1% trifluoroacetic acid in water (Solvent A) and 0.1% trifluoroacetic acid in acetonitrile (Solvent B). Chloride salts were obtained by passing an aqueous solution of the trifluoroacetic acid salt through a Biorad AG® 3×4 ion exchange resin column (100–200 mesh, Cl-form). Purification by HPLC was utilized for each of the Examples 1–23, 27, 48 and 49 as set forth below.

Example 1

2(S)-Butyl-1-(2,3-diaminoprop-1-yl)-4-(1-naphthoyl)piperazine trihydrochloride

Step A: 1-Benzyl-3(S)-n-butylpiperazine-2,5-dione

The title compound was prepared according to the procedure described by John S. Kiely and Stephen R. Priebe in *Organic Preparations and Procedures Int.*, 22 (6), 761–768 (1990). Thus dicyclohexylcarbodiimide (9.33 g, 45.2 mmol) in methylene chloride (0.5M) was added to methylene chloride (250 mL). This solution was cooled to 0° C. under nitrogen and Boc-L-norleucine (10.5 g, 45.2 mmol) was added. The resulting slurry was stirred for 5 min, and then ethyl N-benzylglycinate (8.72 g, 45.2 mmol) was added. The reaction was stirred for 2 h at 0° C., then at 20° C. overnight. The precipitate was removed by filtration, and hydrogen chloride gas bubbled through the methylene chloride solution for 2–4 h, until the reaction was shown to be complete by tlc. The solvent was removed in vacuo, and the residue partitioned between ethyl acetate (150 mL) and saturated sodium bicarbonate solution (42 mL). The organic phase was washed with saturated sodium chloride, dryed over magnesium sulfate, filtered and evaporated. The crude diketopiperazine was triturated with hexane to give the title compound as a white powder. $^1$HNMR (300 MHz, $CDCl_3$) δ 7.24–7.40 (5H, m), 6.22 (1H, br s), 4.07 (1H, dt, J=3, 6 Hz), 3.87 (1H, d, J=17 Hz), 3.80 (1H, d, J=17 Hz), 1.88 (2H, m), 1.35 (4H, m), 0.91 (3H, t, J=7 Hz).

Step B: 4-Benzyl-1-tert-butoxycarbonyl-2(S)-n-butylpiperazine

The product from Step A (4.95 g, 0.019 mol) was dissolved in THF (200 mL) and cooled under nitrogen to 0° C. with mechanical stirring. Lithium aluminum hydride (2.60 g, 0.0685 mol) was added slowly. The reaction was refluxed for 18 h, cooled to 0° C., and quenched by the sequential slow addition of 5 mL $H_2O$, 5 mL 10% sodium hydroxide solution and 5 mL $H_2O$. The reaction was stirred for 30 min and filtered. The solvent was removed in vacuo, the crude product taken up in methylene chloride and dried over magnesium sulfate. The drying agent was removed by filtration, and the filtrate treated with di-tert-butyl dicarbonate ((4.35 g, 0.020 mol). After 2 h at 20° C., saturated sodium bicarbonate was added. The layers were separated, and the organic phase washed with saturated sodium chloride solution, then dried over magnesium sulfate. Filtration and evaporation gave the crude product which was purified by column chromatography on silica gel, eluting with 5% ethyl acetate in hexane. The title compound was obtained as a foam. $^1$HNMR (300 MHz, DMSO-$d_6$) δ 7.25 (5H, m), 3.90 (1H, br s,), 3.73 (1H, d, J=13 Hz), 3.51 (1H, d, J=13 Hz), 3.34 (1H, d, J=13 Hz), 2.93 (1H, m), 2.75 (1H, d, J=11 Hz), 2.62 (1H, d, J=11 Hz), 1.90 (2H, m), 1.60 (2H, m), 1.38 (9H,s), 1.26 (2H, m), 1.04 (2H, m), 0.84 (3H, t, J=7 Hz).

Step C: 1-tert-Butoxycarbonyl-2(S)-n-butylpiperazine

The product from Step B (3.75 g, 11.3 mmol) was dissolved in methanol (75 mL) in a Parr bottle, and the vessel purged with argon. To this was added 10% palladium on carbon (0.80 g) and the reaction hydrogenated under 60 psi hydrogen for 24 h. The catalyst as removed by filtration through Celite, and the filtrate evaporated in acuo to give the title compound as an oil. $^1$HNMR (300 MHz, $CDCl_3$) δ 4.08 (1H, br s), 3.90 (1H, d, J=12 Hz), 2.5–3.8 (6H, m), 1.80 (1H, m), 1.60 (1H, m), 1.46 (9H, s), 1.30 (4H, m),0.90 (3H, t, J=7 Hz).

Step D: 1-tert-Butoxycarbonyl-2(S)-n-butyl-4-(1-naphthoyl)piperazine 1-tert-butoxycarbonyl-2(S)-n-butylpiperazine (0.325 g, 1.34 mmol), 1-hydroxybenzotriazole (HOBT) (0.203 g, 1.34 mmol) and 1-ethyl-3-(3-dimethylamino-propyl)carbodiimide hydrochloride (EDC.HCl) (0.254 g, 1.34 mmol) were added to dry, degassed dimethylformamide (7 mL). The pH of the reaction was adjusted to 7 with triethylamine, and the reaction stirred for 2 h. The dimethylforrnamide (DMF) was distilled in vacuo, and the residue partitioned between ethyl acetate and water. The organic phase was washed with 2% aqueous potassium hydrogen sulfate, saturated sodium bicarbonate solution, saturated sodium chloride solution, and dried over magnesium sulfate. The title compound was obtained as a thick oil.

Step E: 2(S)-n-Butyl-4-(1-naphthoyl)piperazine hydrochloride

The product from Step D was dissolved in ethyl acetate, cooled to −40° C. under nitrogen, and the solution saturated with HCl(g). The solution was warmed to 0° C. for 30 min, and then purged with nitrogen. The solvent was removed in vacuo. The product was evaporated from ethyl acetate three times. The title compound was obtained as a white solid.

Step F: 2,3-(bis-tert-Butoxycarbonylamino)propanoic acid

Diaminopropanoic acid monohydrochloride (2.86 g, 0.0204 mol) was suspended in 1:1 water-dioxane (100 mL) containing triethylamine (5.97 mL, 0.0204 mol). BOC-ON (11.0 g, 0.0448 mol) was added along with additional triethylamine to adjust the pH to 9.5. The reaction was stirred under nitrogen overnight at 20° C. The clear solution was diluted with water and extracted with diethyl ether (5×100 mL). The aqueous solution was adjusted to pH 1 with cold 5% aqueous hydrochloric acid and extracted with ethyl acetate. The organic layer was washed with water, saturated sodium chloride, then dried over magnesium sulfate. The resulting foam (5.46 g) was crystallized from ethyl acetate to give the title compound as a white solid.

Step G: N-Methoxy-N-methyl-2,3-(bis-tert-butoxycarbonylamino)proprionamide 2,3-bis-(tert-Butoxycarbonylamino)propanoic acid (1.80 g, 5.92 mmol) in dimethylformamide (25 mL) was stirred overnight with N-methoxy-N-methylamine hydrochloride (0.635 g, 6.51 mmol), EDC.HCl (1.24 g, 6.51 mmol), N-hydroxybenzotriazole (0.80 g, 5.92 mmol) and triethylamine (0.825 mL, 5.92 mmol). The dimethylformamide was removed in vacuo and the residue partitioned between ethyl acetate and water. The organic phase was washed with 10% hydrochloric acid, saturated sodium bicarbonate solution, saturated brine, and dried over magnesium sulfate. The crude product was chromatographed on silica gel with 30% ethyl acetate in hexane. The title compound was obtained as a foam. $^1$HNMR (CDCl$_3$, 300 MHz) d 5.51 (1H, br d), 4.87 (1H, br s), 4.72 (1H, br s), 3.77 (3H, s), 3.50 (1H, m), 3.40 (1H, dt, J=12, 6 Hz), 3.20 (3H, s), 1.44 (9H, s), 1.42 (9H, s).

Step H: 2,3-(bis-tert-Butoxycarbonylamino)propanal

Lithium aluminum hydride (0.384 g, 10.14 mmol) was suspended in diethyl ether (20 mL) and cooled to −45° C. under nitrogen. N-Methoxy-N-methyl-2,3-(bis-tert-butoxycarbonylamino)proprionamide (2.07 g, 5.96 mmol) in 1:1 ether-tetrahydrofuran (60 mL) was added at such a rate so as to keep the reaction temperature less than −35° C. The reaction was allowed to warm to 5° C., then cooled to −45° C. and quenched with a solution of potassium hydrogen sulfate (3.08 g, 22.6 mmol) in water (20 mL). The reaction was stirred at 20° C. 1 h, then filtered through celite. The organic phase was washed with 10% citric acid and saturated brine, then dried over magnesium sulfate. The title compound was obtained as a foam. NMR (CDCl$_3$, 300 MHz) d 9.61 (1H, s), 5.60 (1H, br s), 4.88 (1H, br s), 4.24 (1H, br d, J=6 Hz), 3.68 (1H, m), 3.50 (1H, m), 1.40 (9H, s), 1.39 (9H, s).

Step I: 1-[(2,3-bis-tert-Butoxycarbonylamino)prop-1-yl]-2 (S)-butyl-4-(1-naphthoyl)piperazine A solution of 3(S)-butyl-1-(1-naphthoyl)piperazine (1.83 g, 6.20 mmol) (free base of the product from Step E), acetic acid (0.17 mL, 2.9 mmol) in dichloroethane (20 mL) was adjusted to pH 5.5 with triethylamine. Sodium triacetoxyborohydride (1.87 g, 8.79 mmol) and crushed molecular sieves (1 g) were added, and the reaction cooled to 0° C. under nitrogen. A solution of 2,3-(bis-tert-butoxycarbonylamino)propanal (1.69 g, 5.86 mmol) in dichloroethane (10 mL) was added dropwise, and the reaction stirred at 20° C. overnight. The reaction was cooled to 0° C., quenched with saturated sodium bicarbonate and stirred for 1 h. The layers were separated and the organic layer washed with saturated brine, then dried over magnesium sulfate. The crude product was chromatographed on silica gel with 40–50% ethyl acetate in hexane, and the title compound was isolated as a foam (Rf 0.30, 50% ethyl acetate in hexane).

Step J: 1-(2,3-Diaminoprop-1-yl)-2(S)-butyl-4-(1-naphthoyl)piperazine trihydrochloride Trifluoroacetic acid (25 mL) was added to a solution of 1-[(2,3-bis-tert-butoxycarbonylamino)prop-1-yl]-2(S)-butyl-4-(1-naphthoyl)piperazine (2.13 g, 3.75 mmol) in dichloromethane (75 mL). After 25 min at 20° C., the solvent was evaporated and the residue partitioned between chloroform and 20% aqueous sodium hydroxide. The organic layer was washed with saturated brine and dried over magnesium sulfate. The free base of the title compound was obtained as a yellow gum (1.72 g). A portion of this material (52 mg) was purified by preparative HPLC using a 100 mm Waters PrepPak® reverse phase column (DeltaPak™ C$_{18}$, 50 mM, 100 Å), and pure product isolated by gradient elution using 100% 0.1% trifluoroacetic acid in water (Solvent A) to 50% Solvent A and 50% 0.1% trifluoracetic acid in acetonitrile (Solvent B). The pure fractions were combined and the solvent evaporated, and the crude product dissolved in water and passed through an ion exchange column (Biorad AG® 3×4 ion exchange resin, chloride form). After lyophilization, the title compound was obtained as a white solid. Anal. Calc. for C$_{22}$H$_{32}$N$_4$O.4.45 HCl C, 49.79; H, 6.92; N, 10.56. Found: C, 49.75; H, 6.72; N, 10.36.

Example 2

1-(3-Amino-2-(2-naphthylmethylamino)prop-1-yl)-2(S)-butyl-4-(1-naphthoyl)piperazine trihydrochloride Step A: 1-[(2-Amino-3-tert-butoxycarbonylaminoprop-1-yl]-2(S)-butyl-4-(1-naphthoyl)piperazine Di-tert-butyl dicarbonate (0.282 g, 1.29 mmol) was added to a solution of 4-(2,3-diaminoprop-1-yl)-2(S)-butyl-1-(1-naphthoyl)piperazine (0.476 g, 1.29 mmol) in dichloromethane (10 mL). The reaction was stirred a total of 2 h at 20° C., then quenched and extracted with water. The organic phase was washed with saturated brine and dried over magnesium sulfate. The crude product was chromatographed on silica gel with 5% methanol in chloroform followed by 5% (9:1 methanol-ammonium hydroxide) in chloroform. The title compound was isolated as the major product. FAB ms (m+1) 469.

Step B: 1-(3-tert-Butoxycarbonylamino-2-(2-naphthylmethylamino)prop-1-yl)-2(S)-butyl-4-(1-naphthoyl)piperazine The title compound was prepared according to the procedure described in Example 1, Step D except using 1-[(2-amino-3-tert-butoxycarbonylaminoprop-1-yl]-2(S)-butyl-4-(1-naphthoyl)piperazine (0.287 g, 0.613 mmol), naphthalene-2-carboxaldehyde (0.95 g, 0.613 mmol), sodium triacetoxyborohydride (0.194 g, 0.919 mmol), in dichloroethane (15 mL) at pH 6. The crude product was chromatographed on silica gel with 5% methanol in chloroform (R$_f$ 0.30), and the title compound isolated as a foam. FAB ms (m+1) 609.

Step C: 1-(3-Amino-2-(2-naphthylmethylamino)prop-1-yl)-2(S)-butyl-4-(1-naphthoyl)piperazine trihydrochloride A solution of 1-(3-tert-butoxycarbonylamino-2-(2-naphthylmethylamino)prop-1-yl)-2(S)-butyl-4-(1-naphthoyl)piperazine (0.313 g, 0.514 mmol) in methylene chloride (10 mL) was deprotected with trifluoroacetic acid (5 mL) and converted to the free base (255 mg) according to the procedure described in Example 1, Step E. Purification of 40 mg by preparative HPLC used gradient elution with solvents A and B (from Example 1; 95% to 5% solvent A). Ion exchange and lyophilization as described furnished the title compound as a white solid. FAB ms (m+1) 509. Anal. Calc. for $C_{33}H_{40}N_4O.0.05 H_2O$ 4.45 HCl: C, 59.00; H, 6.68; N, 8.34. Found: C, 59.00; H, 6.51; N, 8.44.

Example 3

2(S)-Butyl-1-{5-[1-(2-naphthylmethyl)]-4,5-dihydroimidazol}methyl-4-(1-naphthoyl)piperazine ditrifluoroacetate 1-(3-Amino-2-(2-naphthylmethylamino)prop-1-yl)-2(S)-butyl-4-(1-naphthoyl)piperazine (0.105 g, 0.207 mmol), tert-butylisocyanate (1.5 mL) and silver cyanide (0.023 g, 0.207 mmol) were heated in a sealed tube under nitrogen at 90° C. overnight. The volatiles were removed in vacuo, and the residue chromatographed on silica gel with 5–10% methanol in chloroform to give the free base (73 mg). This was purified by preparative HPLC as described in Example 1 by gradient elution with solvents A and B (from Example 1; 95% to 5% solvent A ). Lyophilization furnished the title compound as a white solid. FAB ms (m+1) 519. Anal. Calc. for $C_{34}H_{38}N_4O.0.85 H_2O$ 3.75 TFA: C, 51.84; H, 4.55; N, 5.83. Found: C, 51.83; H, 4.56; N, 6.32.

Example 4

1-[5-(1-Benzylimidazol)methyl]-2(S)-butyl-4-(1-naphthoyl)piperazine dihydrochloride Benzyl bromide (0.012 mL, 0.103 mmol) was added to a solution of 2(S)-butyl-1-[5-(3-triphenylmethylimidazol)]methyl-4-(1-naphthoyl)piperazine (63 mg, 0.103 mmol) in acetonitrile (0.5 mL) at 20° C. under nitrogen. The reaction was stirred overnight, concentrated in vacuo, and taken up in dichlormethane (2 mL) containing triethylsilane (0.100 mL). Trifluoroacetic acid was added and the reaction stirred for 1 h at 20° C. The solvent was evaporated and the residue purified by HPLC (95% to 5% solvent A). Pure fractions were combined and converted to the HCl salt as described in Example 1, Step E. After lyophilization, the title compound was isolated as a white solid. FAB ms (m+1) 467. Anal. Calc. for $C_{30}H_{34}N_4O.0.05 H_2O.3.70 HCl$: C, 59.81; H, 6.32; N, 9.30. Found: C, 59.78; H, 6.33; N, 9.30.

Example 5

1-{5-[1-(4-nitrobenzyl)]imidazolylmethyl}-2(S)-butyl-4-(1-naphthoyl)piperazine ditrifluoroacetate The title compound was prepared according to the procedure described in Example 4, except using p-nitrobenzylbromide (0.043 g, 0.199 mmol) and 2(S)-butyl-1-[5-(3-triphenylmethylimidazol)]methyl-4-(1-naphthoyl)piperazine (123 mg, 0.199 mmol) in acetonitrile (2 mL). The crude product was treated with triethylsilane (0.127 mL, 0.80 mmol) and trifluoroacetic acid (2 mL) in dichloroethane (4 mL). Preparative HPLC (95–5% solvent A) provided the title compound as a white solid. FAB ms (m+1) 512. Anal. Calc. for $C_{30}H_{33}N_5O_3.2 CF_2CO_2H.0.03 H_2O$: C, 41.42; H, 3.98; N, 10.18. Found: C, 41.43; H, 3.96; N, 10.51.

Example 6

1-(3-Acetamidomethylthio-2(R)-aminoprop-1-yl)-2 (S)-butyl-4-(1-naphthoyl)piperazine ditrifluoroacetate 1-(3-Acetamidomethylthio-2(R)-aminoprop-1-yl)-2(S)-butyl-4-(1-naphthoyl)piperazine dihydrochloride and N-hydroxymethylacetamide (0.010 g, 0.105 mmol) (prepared as described in M. Bodansky, A. Bodansky, "The Practice of Peptide Synthesis", Springer-Verlag, 1984, p.82) were dissolved in trifluoroacetic acid for 0.5 h. The solvent was removed in vacuo and the residue purified by preparative HPLC (85–60% solvent A). After lyophilization, the title compound was isolated as a solid. FAB ms (m+1) 457. Anal. Calc. for $C_{25}H_{36}N_4O_2S.2 CF_2CO_2H.1.9 H_2O$. C, 44.39 H, 5.12; N, 6.64. Found: C, 44.35; H, 5.11; N, 6.97.

Example 7

2(S)-Butyl-1-[2-(1-imidazolyl)ethyl]sulfonyl-4-(1-naphthoyl)piperazine ditrifluoroacetate Step A: 2(S)-Butyl-4-(1-naphthoyl)-1-vinylsulfonylpiperazine Chloroethylsulfonylchloride (0.038 mL, 0.314 mmol) was added to a solution of 3(S)-butyl-1-(1-naphthoyl) piperazine (0.095 g, 0.285 mmol) and diisopropylethylamine (0.119 mL, 0.685 mmol) in dichloromethane (3 mL). The reaction was stirred overnight under nitrogen, quenched with saturated sodium bicarbonate and extracted into ethyl acetate. After drying with magnesium sulfate, the title compound was isolated.

Step B: 2(S)-Butyl-1-[2-(1-imidazolyl)ethyl]sulfonyl-4-(1-naphthoyl)piperazine ditrifluoroacetate Imidazole (0.043 g, 0.627 mmol) was added to sodium hydride (60% dispersion in oil, 0.024 g, 0.598 mmol) suspended in dimethylformamide (2 mL). The reaction was cooled to 0° C. under nitrogen, and 2(S)-butyl-4-(1-naphthoyl)-1-vinylsulfonylpiperazine (0.011 g, 0.29 mmol) in dimethylformamide (5 mL) was added. The reaction was stirred at 20° C. overnight. The dimethylformaide was removed in vacuo and the residue dissolved in ethyl acetate. This was extracted with saturated sodium bicarbonate solution, saturated brine and dried over magnesium sulfate. The crude product was first purified by silica gel chromatography using 8% methanol in chloroform, then by preparative HPLC (80 to 40% solvent A). The trifluoroacetate salt was dissolved in water and partitioned between saturated sodium bicarbonate and ethyl acetate. The organic phase was washed with saturated brine and dried over magnesium sulfate. The title compound was obtained as a foam. FAB ms (m+1) 455. Anal. Calc. for $C_{25}H_{36}N_4O_2S.0.8 H_2O$. C, 61.46; H, 6.79; N, 11.95. Found: C, 61.44; H, 6.97; N, 10.72.

Example 8

2(R)-Butyl-1-imidazolyl-4-methyl-4-(1-naphthoyl) piperazine

Step A: 2(R)-Butyl-4-(1-naphthoyl)-1-[4-(1-triphenylmethylimidazolyl]methyl-piperazine 3(R)-Butyl-1-(1-naphthoyl)piperazine (0.202 g, 0.607 mmol) (prepared as described for the (S) enantiomer in Example 1) was reacted with 1-triphenylmethylimidazole- 4-carboxaldehye (0.226 g, 0.667 mmol), sodium triacetoxyborohydride (0.321 g, 1.52 mmol), in dichloroethane (7 mL) in the presence of crushed molecular sieves. The pH was adjusted to 5–6 with triethylamine/acetic acid. The reaction was stirred overnight, then quenched with saturated sodium bicarbonate. The organic layer was washed with saturated brine, and dried over magnesium sulfate. The crude product was purified by chromatography on silica gel with 30% ethyl acetate in hexane followed by 5% methanol in chloroform, to obtain the title compound.

Step B: 2(R)-Butyl-1-imidazolyl-4-methyl-4-(1-naphthoyl) piperazine ditrifluoroacetate Triethylsilane (1.0 mL, 11.80 mmol) was added to a solution of 2(R)-butyl-4-(1-naphthoyl)-1-[4-(1-triphenylmethylimidazolyl]methyl-piperazine (0.381 g, 0.616 mmol) in dichloromethane, followed by trifluoroacetic acid (8 mL). After 1 h, the solvents were evaporated and the residue partitioned between water and hexane. The aqueous phase was injected directly onto a preparative HPLC column (100–40% solvent A) and the title compound isolated after lyophilization. FAB ms (m+1) 377. Anal. Calc. for $C_{25}H_{36}N_4O_2$.2.35 $CF_3CO_2H$.0.32 $H_2O$. C, 48.93; H, 4.52; N, 7.98. Found: C, 48.93; H, 4.55; N, 8.26.

Example 9

2(S)-Butyl-4-(1-naphthoyl)-1-(3-pyridylmethyl) piperazine dihydrochloride

3(S)-Butyl-1-(1-naphthoyl)piperazine hydrochloride (0.200 g, 0.601 mmol) was reacted with pyridine-3-carboxaldehyde (0.062 mL, 0.661 mmol), sodium triacetoxyborohydride (0.321 g, 1.52 mmol), in dichloroethane (7 mL) at pH 5–6 in the presence of crushed molecular sieves as described in Example 8, Step A. The crude product was purified by silica gel chromatography with 30% acetone in hexane, followed by preparative HPLC (80–75% solvent A). After ion exchange, the title compound was isolated. FAB ms (m+1) 388. Anal. Calc. for $C_{25}H_{29}N_3O$.2.3 HCl.0.95 $H_2O$. C, 61.49; H, 6.85; N, 8.60. Found: C, 61.49; H, 7.01; N, 8.76.

Example 10

1-2(S)-Butyl-(2(R)-(4-nitrobenzyl)amino-3-hydroxypropyl)-4-(1-naphthoyl)piperazine dihydrochloride 1-(2(R)-amino-3-hydroxypropyl)-2(S)-butyl-4-(1-naphthoyl)piperazine (120 mg, 0.326 mmol) was converted to the title compound according to the procedure described in Example 8, Step A using 4-nitrobenzaldehyde (0.493 g, 0.327 mmol), sodium triacetoxyborohydride (0.173 g, 0.817 mmol), in dichloroethane. The crude product was purified by preparative HPLC (100–75% solvent A), and after ion exchange to the HCl salt and lyophilization, the title compound was obtained. FAB ms (m+1) 505. Anal. Calc. for $C_{25}H_{29}N_3O$.3.6 HCl.0.10 $H_2O$. C, 54.69; H, 6.30; N, 8.80. Found: C, 54.66; H, 5.85; N, 8.31.

Example 11

1-(2(R)-Amino-3-hydroxyheptadecyl)-2(S)-butyl-4-(1-naphthoyl)piperazine ditrifluoroacetate Step A: 1-(2(R)-t-Butyoxycarbonylamino-2-formylethyl)-2(S)-butyl-4-(1-naphthoyl)piperazine A solution of oxalyl chloride (1.36 mL, 14.9 mmol) in dichloromethane (35 mL) was cooled to –65° C. under nitrogen, and dimethylsulfoxide (2.30 mL, 32.4 mmol) in methylene chloride (7 mL) added, and the reaction stirred 2 min. A solution of 1-(2(R)-amino-3-hydroxypropyl)-2(S)-butyl-4-(1-naphthoyl)piperazine (3.19 g, 6.79 mmol) was added to this solution at –10° C. and the reaction stirred at this temperature for 15 min. The reaction was cooled to –55° C. and triethylamine (4.76 mL, 34 mmol) added. The reaction was stirred for 5 min then warmed to room temperature. Additional methylene chloride is added and the reaction is extracted with water. The organic phase was washed with 2% potassium hydrogen sulfate, water, dilute sodium bicarbonate solution, and saturated brine. After drying with agnesium sulfate, the title compound was obtained.

Step B: 1-(2(R)-Amino-3-hydroxyheptadecyl)-2(S)-butyl-4-(1-naphthoyl)piperazine ditrifluoroacetate A solution of 0.25 g, 0.53 mmol)1-(2(R)-t-butoxycarbonylamino-2-formylethyl)-2(S)-butyl-4-(1-naphthoyl)piperazine in dry tetrahydrofuran (5 mL) was cooled to 0° C. under nitrogen in a flame-dried three necked flask. A solution of heptadecylmagnesium chloride (1.01 mL of a 1M solution in ether, 1.01 mmol) was added via syringe, and the reaction allowed to warm to room temperature. The reaction was quenched with saturated sodium bicarbonate solution, and then extracted with ethyl acetate. After drying over magnesium sulfate, the crude product was chromatographed on silica gel with 25% ethyl acetate in hexane followed by 5% methanol in chloroform. The purified product was dissolved in methylene chloride (7 mL) and treated with trifluoroacetic acid (3.5 mL). After 45 min, the solvents were removed in vacuo and the residue purified by preparative HPLC (95–40% solvent A). Two isomers were separated. After lyophilization, the title compound was isolated as diastereomer A (retention time 8.405 min, gradient 100–50% solvent A over15 min), FAB ms (m+1) 566, Anal. Calc. for $C_{36}H_{59}N_3O_2$. 2.35 $CF_3CO_2H$. 0.35 $H_2O$. C, 58.19; H, 7.44; N, 5.00. Found: C, 58.21; H, 7.46; N, 5.36. After lyophilization, the title compound was also isolated as diastereomer B (retention time 9.269 min, gradient 100–50% solvent A over15 min), FAB ms (m+1) 566, Anal. Calc. for $C_{36}H_{59}N_3O_2$. 2.35 $CF_3CO_2H$. 0.05 $H_2O$. C, 58.56; H, 7.42; N, 5.03. Found: C, 58.53; H, 7.41; N, 5.17.

Example 12

2(S)-Benzyl-1-imidazolyl-4-methyl-4-(1-naphthoyl) piperazine

Step A: 1,(3S)-Dibenzylpiperazine-2,5-dione

The title compound was prepared according to the procedure described in Example 1, Step A, except using Boc-L-phenylalanine (12.8 g, 48.2 mmol), ethyl N-henzylglycinate (9.32 g, 48.2 mmol) and dicyclohexylcarbodiimide (96.5 mL 0.5M in dichloromethane, 48.2 mmol). The crude diketopiperazine was triturated with hexane to give the title compound as a white powder. $^1$HNMR (300 MHz, $CD_3OD$) δ 7.0–7.4 (10H, m), 4.61 (1H, d, J=16 Hz), 4.37 (1H, t, J=5 Hz), 4.24 (1H, d, J=16 Hz), 3.42 (1H, d, J=18 Hz), 3.28 (1H, dd, J=4, 16 Hz), 2.96 (1H, dd, J=6, 16 Hz), 2.55 (1H, d, J=18 Hz).

Step B: 1-tert -Butoxycarbonyl-2(S)-,(S),4-dibenzylpiperazine

The title compound was prepared according to the procedure described in Example 1, Step B, except using 1,3(S)-dibenzylpiperazine-2,5-dione (5.01 g, 17.1 mmol) and lithium aluminum hydride (2.33 g, 61.4 mmol), followed by di-tert-butyl dicarbonate (4.02 g, 18.4 mmol). The crude product was purified by column chromatography on silica gel, eluting with 7.5% ethyl acetate in hexane. The title compound was obtained as a white solid. $^1$HNMR (300

MHz, CD$_3$OD) δ 7.2–7.4 (5H, m), 7.0–7.2 (5H, m), 4.15 (1H, m), 3.90 (1H, d, J=15 Hz), 3.60 (1H, d, J=15 Hz), 3.15 (1H, m), 2.95 (3H, m), 2.7 (1H, d, J=13 Hz), 2.02 (1H, dt, J=6, 13 Hz), 1.95 (1H, br d), 1.35 (9H, s).

Step C: 2(S)-Benzyl-1-tert-butoxycarbonylpiperazine

The title compound was prepared according to the procedure described in Example 1, Step C, except using 1-tert-butoxycarbonyl-2(S),4-dibenzylpiperazine (4.78 g, 11.3 mmol) and 10% palladium on carbon (1.04 g). The title compound was obtained as an oil. $^1$HNMR (300 MHz, CD$_3$OD) δ 7.25 (5H, m), 4.35 (1H, m), 4.00 (1H, d, J=12 Hz), 2.7–3.3 (7H, m), 1.25 (9H, s).

Step D: 2(S)-Benzyl-1-tert-butoxycarbonyl-4-(1-naphthoyl) piperazine

The title compound was prepared according to the procedure described for Example 1, Step A except using 2(S)-benzyl-1-tert-butoxycarbonylpiperazine (0.292 g, 1.06 mmol), 2,3-dimethylbenzoic acid (0.159 g, 1.06 mmol), HOBT (0.157 g, 1.02 mmol), EDC.HCl (0.213 g, 1.11 mmol) and triethylamine to adjust the pH to 7. The title compound was obtained as a thick oil. $^1$HNMR (DMSO-d$_6$, 300 MHz) δ 7.15 (2H, m), 6.06 (1H,m), 4.42 (1H,m), 3.6–4.2 (2H, m), 2.7–3.24 (4H, m), 2.24 (3H, s), 2.03–2.20 (3H, 4s), 1.10–1.6 (15H, m), 0.72–1.00 (3H, m).

Step E: 2(S)-Benzyl-4-(1-naphthoyl)-1-[4-(1-triphenylmethylimidazolyl]methyl-piperazine 3(S)-Benzyl-1-(1-naphthoyl)piperazine (0.173 g, 0.472 mmol) was reacted with 1-triphenylmethylimidazole-4-carboxaldehyde (0.160 g, 0.472 mmol), sodium triacetoxyborohydride (0.300 g, 1.42 mmol), in dichloroethane (7 mL) in the presence of crushed molecular sieves as described in Example 8, Step A. The title compound was obtained as an oil.

Step F: 2(S)-Benzyl-1-imidazolyl-4-methyl-4-(1-naphthoyl) pilperazine ditrifluoroacetate Triethylsilane (0.300 mL, 1.89 mmol) was added to a solution of 2(S)-benzyl-4-(1-naphthoyl)-1-[4-(1-triphenylmethylimidazolyl]methyl-piperazine (0.310 g, 0.472 mmol) in dichloromethane (5 mL), followed by trifluoroacetic acid (5 mL). After 1 h, the solvents were evaporated and the residue partitioned between water and hexane. The aqueous phase was injected directly onto a preparative HPLC column (85–45% solvent A) and the title compound isolated after lyophilization. FAB ms (m+1) 411. Anal. Calc. for C$_{26}$H$_{26}$N$_4$O$_2$. 2.75 CF$_3$CO$_2$H. 0.05 H$_2$O. C, 52.11; H, 4.14; N, 7.72. Found: C, 52.10; H, 4.03; N, 8.16.

Example 13

1-(2(R)-Amino-3-(3-benzylthio)propyl)-2(S)-butyl-4-(1-naphthoyl) piperazine ditrifluoroacetate Step A: 1-[(1-Aziridinyl)methyl]-2(S)-butyl-4-(1-naphthoyl) piperazine A solution of 1-(2(R)-butoxycarbonylamino-3-hydroxypropyl)-2(S)-butyl-4-(1-naphthoyl)piperazine (1.67 g, 3.56 mmol) in dimethylformamide (10 mL) was cooled to 0° C. under nitrogen. Sodium hydride (0.427 g, 10.6 mmol, 60% dispersion in oil) was added, followed by 1,1'-sulfonyldiimidazole (0.704 g, 3.56 mol). The reaction was warmed to 20° C. for 1 h, cooled to 0° C. and quenched with water. Dimethylformamide was distilled in vacuo, and the residue partitioned between ethyl acetate and water. The organic phase was washed with saturated brine and dried over magnesium sulfate. The crude product was chromatographed on silica gel with 70% ethyl acetate in hexane, followed by 5% methanol in chloroform. The title compound was obtained as the major product, FAB ms (m+1) 352. A lesser amount of 1-[(1-butoxycarbonylaziridinyl) methyl]-2(S)-butyl-4-(1-naphthoyl)piperazine was also isolated.

Step B: 1-(2(R)-Amino-3-(3-benzylthio)propyl)-2(S)-butyl-4-(1-naphthoyl)piperazine ditrifluoroacetate 1-[(1-Aziridinyl)methyl]-2(S)-butyl-4-(1-naphthoyl) piperazine (0.050 g, 0.142 mmol) was refluxed for 18 h with benzyl mercaptan (0.100 mL, 0.852 mmol) and triethylamine (0.200 mL) in methanol (4 mL). The crude product was first chromatographed on silica gel with 3% methanol in chloroform, and then purified by preparative HPLC (85% to 10% solvent A). The title compound was obtained after lyophilization. FAB ms (m+1) 476. Anal. Calc. for C$_{29}$H$_{37}$N$_3$OS. 2.6 CF$_3$CO$_2$H. 0.3 H$_2$O. C, 52.83; H, 5.21; N, 5.40. Found: C, 52.78; H, 5.17; N, 5.66.

Example 14

1-(2(R)-Amino-3-[3-(4-nitrobenzylthio)propyl]))-2(S)-butyl-4-(1-aphthoyl)piperazine ditrifluoroacetate A solution of 1-[(1-butoxycarbonylaziridinyl)methyl]-2(S)-butyl-4-(1-naphthoyl)piperazine (0.050 g, 0.111 mmol) in methanol (4 mL) was reluxed with p-nitrobenzylthioacetate (0.070 g, 0.333 mmol) and triethylamine (0.200 mL) for 2 h. The crude product was hromatographed on silica gel with 3% methanol in chloroform. The purified product was treated with 33% trifluoroacetic acid in methylene chloride for 20 min. The solvents were evaporated and the product purified by preparative HPLC (85%–10% solvent A). The title compound was obtained after lyophilization. FAB ms (m+1) 529. Anal. Calc. for C$_{29}$H$_{36}$N$_4$O$_3$. 2 CF$_3$CO$_2$H. 0.08 H$_2$O. C, 51.94; H, 5.23; N, 7.34. Found: C, 51.87; H, 5.06; N, 7.47.

Example 15

2(S)-Butyl-1-[(4-imidazolyl)ethyl]-4-(1-naphthoyl) piperazine dihydrochloride

Step A: N-Methyl-N-methoxy-2-(1-triphenylmethyl-1H-imidazol-4-yl)acetamide

To a solution of 4-imidazoleacetic acid (1.04 g, 6.40 mmol) and triphenylmethyl bromide (2.48 g, 7.68 mmol) in dimethylformamide (40 ml) was added triethylamine (4.46 ml, 32 mmol) and the suspension allowed to stir for 18 hours at room temperature. After this time, the mixture was treated with 3-hydroxy-1,2,3-benzotriazin-4(3)-one (HOOBT) (1.31 g, 8 mmol), N, O-dimethylhydroxyamine hydrochloride (1.56 g, 16 mmol) and 1-(3-dimethylaminopropyl)-3-ethylcarbodiimide hydrochloride (EDC) (1.53 g, 8 mmol) and stirred for 24 hours at room temperature. After this time, sat. aq. sodium bicarbonate (50 ml) and water (50 ml) were added and the mixture was extracted with ethyl acetate (2×100 ml). The combined extracts were washed with sat. aq. NaHCO$_3$ (100 ml) and then brine (50 ml) and the solvent evaporated in vacuo. The residue was suspended in ether (20 ml) and the white solid filtered to give the title compound as a white solid. $^1$NMR(CD$_3$OD, 300 MHz) δ 7.37(10H, m), 7.16(6H, m), 6.84(1H, s), 3.73(2H, s), 3.68(3H, s) and 3.18(3H, s)ppm.

Step B: 2-(1-triphenylmethyl-1H-imidlazol-4-yl) acetaldehyde

To a solution of the product from Step A (300 mg, 0.73 mmol) in freshly distilled THF (15 ml) cooled to −40° C. over dry ice/acetone was added lithium aluminum hydride (33.2 mg, 0.874 mmol). The resulting suspension was allowed to warm to +5° C. and then maintained at 0° C. for 30 min. After this time, the reaction mixture was recooled to −40° C. and quenched sequentially with water (33 μl), 1.0N NaOH (33 μl) and water (100 μl). The resulting suspension was stirred for 30 min, filtered and the solvent removed in vacuo. The residue was dissolved in methylene chloride (5 ml) and washed with 10% aq. citric acid (5 ml) and then water (5 ml). The organic layer was dried(MgSO$_4$) and the solvent evaporated in vacuo to give the title compound. $^1$HNMR (CDCl$_3$, 300 MHz) δ 9.79(1H, t, J=3 Hz), 7.44(1H, s), 7.4–7.1(15H, m), 6.76(1H, s) and 3.63(2H, d, J=3 Hz)ppm.

Step C: 2(S)-Butyl-1-[(4-imidazolyl)ethyl]-4-(1-naphthoyl) piperazine ditrifluoroacetate To a solution of the product from Step B (89 mg, 0.263 mmol) and 3(S)-butyl-1-naphthoylpiperazine hydrochloride (62.6 mg, 0.188 mmol) in 1,2-dichloroethane (4 ml) was added 3A molecular sieves (400 mg) and sodium triacetoxyborohydride (200 mg, 0.94 mmol). This mixture was stirred at room temperature for 4 days. After this time, filtered the mixture through sintered glass. The filtrate was diluted with methylene chloride (50 ml) and washed with water (25 ml). The solvent was evaporated in vacuo and the residue was purified by flash chromatography eluting with 2–5% methanol/methylene chloride to provide the trityl protected title compound as an oil. This oil was dissolved in methylene chloride (2 ml) and trifluoroacetic acid (1 ml) and treated with triethylsilane (2 drops) to give a colorless solution. This solution was stirred at room temperature for 3 hours and then the solvent was evaporated in vacuo. The resulting residue was dissolved in water (20 ml) and washed with hexanes (20 ml). The aqueous layer was lyophilized to give the title compound. $^1$HNMR (CD$_3$OD, 300 MHz) δ 8.83(1H, s), 8.08–7.75(3H, m), 7.67–7.49(4H, m), 7.45(1H, s), 4.5–3.8 (2H, m), 3.65–2.95(9H, m), 2.0–1.3(4H, m) and 2.2–0.2(5H, m)ppm. Anal. calc'd for C$_{24}$H$_{30}$N$_4$O 3.45 TFA 0.75H$_2$O: C, 46.54; H, 4.42; N, 7.03. Found: C, 46.54; H, 4.41; N, 7.35. FAB HRMS exact mass calc'd for C$_{23}$H$_{31}$N$_4$O 391.249787 (MH$^+$), found 391.249028

Example 16

2(S)-Butyl-1-[(4-imidazolyl)methyl]-4-(1-naphthoyl) piperazine ditrifluoroacetate To a solution of the product from Step C (102 mg, 0.30 mmol) and 3(S)-butyl-1-naphthoylpiperazirie hydrochloride (62.6 mg, 0.188 mmol) in 1,2-dichloroethane (5 ml) was added sodium triacetoxyborohydride (200 mg, 0.94 mmol) and triethylamine to pH=5.5 and stirred at room temp. for 18 hours. After this time, the mixture was filtered. The filtrate was concentrated in vacuo and dissolved in ethyl acetate (25 ml) and washed with sat. aq. NaHCO$_3$ (10 ml) and then brine (10 ml). The solvent was evaporated in vacuo and the residue was purified by flash chromatography eluting with 3–8% methanol/methylene chloride to provide the trityl protected title compound. This oil was dissolved in methylene chloride (4 ml) and trifluoroacetic acid (2 ml) and treated with triethylsilane until the yellow color disappeared to give a colorless solution. Stirring continued at room temp. for 10 min. and the solvent evaporated in vacuo. The resulting white solid was partially dissolved in water (7 ml) and filtered. The filtrate was purified by Prep HPLC using a Nova Prep 5000 Semi Preparative HPLC system and a Waters PrepPak cartridge (47×300 mm, C18, 15 μm, 100Å) eluting with 5–95% acetonitrile/water (0.1% TFA) at 100 ml/min (Chromatography A) to give the title compound after lyophilization $^1$HNMR (DMSO-d$_6$, 400 MHz, 150° C.) δ 8.53(1H, s), 7.94(2H, m), 7.79(1H, m), 7.53(3H, m), 7.41 (1H, m), 7.40(1H, s), 4.12(1H, d, J=4.8Hz), 3.95(1H, d, J=4.8Hz), 3.70(1H, s), 3.63(1H, s), 3.48(1H, s), 3.40(1H, s), 3.01(1H, s), 2.82(1H, s), 2.74(1H, s), 1.70(1H, m), 1.49(1H, m). 1.18(2H, s), 1.08(2H, s) and 0.77(3H, t, J=5.5 Hz)ppm.

Anal. calc'd for C$_{23}$H$_{29}$N$_4$O 2 TFA 0.70H$_2$O: C, 52.55; H, 5.13; N, 9.08. Found: C, 52.54; H, 5.11; N, 9.35. FAB MS mass calc'd for C$_{23}$H$_{30}$N$_4$O 377 (MH$^+$), found 377.

Example 17

2(S)-Butyl-1-[(1-naphth-2-ylmethyl)-1H-imidazol-5-yl)acetyl]-4-(1-naphthoyl)piperazine dihydrochloride Step A: Preparation of 1H-Imidazole-4-acetic acid methyl ester hydrochloride To a solution of 1H-imidazole-4-acetic acid hydrochloride (4.00 g, 24.6 mmol) in methanol (100 ml) was bubbled hydrogen chloride gas until saturated. This solution was allowed to stand for 18 h at room temperature and the solvent evaporated in vacuo to give the title compound as a white solid. $^1$H NMR(CDCl$_3$, 400 MHz) δ 8.85(1H, s),7.45 (1H, s), 3.89(2H, s) and 3.75(3H, s) ppm.

Step B: Preparation of 1-(Triphenylmethyl)-1H-imidazol-4-ylacetic acid methyl ester To a suspension of the product from Step A (7.49 g, 42.4 mmol) in methylene chloride (200 ml) was added triethylamine (17.7 ml, 127 mmol) and triphenylmethyl bromide (16.4 g, 50.8 mmol) and stirred for 72 h. After this time, the reaction mixture was washed with sat. aq. NaHCO$_3$ (100 ml) and water (100 ml). The organic layer was evaporated in vacuo and the residue was purified by flash chromatography (30–100% ethyl acetate in hexanes gradient elution) to provide the title compound as a white solid. $^1$H NMR (CDCl$_3$, 400 MHz) δ 7.35(1H, s), 7.31(9H, m), 7.22(6H, m), 6.76(1H, s), 3.68(3H, s) and 3.60(2H, s) ppm.

Step C: Preparation of 2-[1-(Naphth-2-ylmethyl)-1H-imidazol-5-yl)]acetic acid methyl ester To a solution of the product of Step B (4.36 g, 11.4 mmol) in acetonitrile (70 ml) was added 2-(bromomethyl) naphthalene and heated to 55° C. for 4 h. After this time, the reaction was cooled to room temperature and the resulting white precipitate was collected by filtration. The filtrate was concentrated to 30 ml and heated to 55° C. for 18 h. After this time, the reaction was cooled to room temperature and filtered the resulting white precipitate collected by filtration. The filtrate was concentrated to 10 ml volume and heated to 55° C. for 1 h. After this time, the reaction was again cooled to room temperature and diluted with ethyl acetate (25 ml). The resulting precipitate was collected by filtration and combined with the previous 2 precipitates in methanol (100 ml) and heated to reflux for 30 m. After this time, the solvent was removed in vacuo and the resulting residue was partioned between methylene chloride(200 ml) and sodium bicarbonate (100 ml). The organic layer was evaporated in vacuo to dryness and the residue was purified by flash chromatography (0–6% methanol/methylene chloride gradient) to provide the title compound as an off white solid $^1$HNMR (CDCl$_3$, 400 MHz) δ 7.82(2H, m), 7.75(1H, m), 7.70(1H, s), 7.49(3H, m), 7.20(1H, d, J=9.4 Hz), 7.06(1H, s), 5.32(2H, s), 3.57(3H, s) and 3.49(2H, s) ppm.

Step D: Preparation of 2-[1-(Naphth-2-ylmethyl)-1H-imidazol-5-yl]acetic acid hydrochloride 2-[1-(Naphth-2-ylmethyl)-1H-imidazol-5-yl]acetic acid methyl ester (0.92 g, 3.28 mmol ) was dissolved in 2.5N hydrochloric acid (50 ml) and heated to 55° C. for 3 h. After this time, the solution was concentrated to dryness in vacuo to give the title compound as a white solid. $^1$HNMR (CD$_3$OD, 400 MHz) δ 8.92(1H, s),7.94(1H, d, J=8.6 Hz), 7.88(2H, m), 7.93(1H, s), 7.54(3H, m), 7.43(1H, d, J=14 Hz), 5.60(2H, s) and 3.82(2H, s) ppm.

Step E: Preparation of 2(S)-Butyl-1-[(1-(naphth-2-ylmethyl) -1H-imidazol-5-yl)acetyl]-4-(1-naphthoyl)piperazine dihydrochloride To a solution of the product from Step D (100 mg, 0.330 mmol), 3(S)-butyl-1-naphthoylpiperazine hydrochloride (100 mg, 0.300 mmol) and 3-hydroxy-1,2,3-benzotriazin-4 (3H)-one (HOOBT) (54 mg, 0.33 mmol) in dimethylformamide (2 ml) was added 1-(3-dimethylaminopropyl)-3-ethylcarbodiimide hydrochloride (EDC) (63 mg, 0.33 mmol) and triethylamine (161 ul, 1.16 mmol) and the resulting suspension stirred for 18 hours. After this time, sat. aq. NaHCO$_3$ (7 ml) was added and the resulting precipitate filtered. The solid was redissolved in methylene chloride and washed with water (25 ml) and brine (20 ml). The solvent was evaporated in vacuo and the residue purified by Preparative HPLC (Chromatography A) to give after lyophillization the title compound. $^1$HNMR (CDCl$_3$, 400 MHz) δ 8.98(1H, m), 8.03–7.27(15H, m), 5.69–5.50(2H, m), 4.79–4.34(2H, m), 4.15–2.50(7H, m), 1.8–0.2(9H, m)ppm. Anal. calc'd for C$_{35}$H$_{35}$N$_4$O2 HCl 0.65H$_2$O: C, 67.30; H, 6.16; N, 8.97. Found: C, 67.25; H, 6.16; N, 9.15. FAB HRMS exact mass calc'd for C$_{35}$H$_{36}$N$_4$O2 545.291652 (MH$^+$), found 545.292050.

Example 18

2(S)-Butyl-1-[(1-naphth-2-ylmethyl)-1H-imidazol-5-yl)ethyl]4-(1-naphthoyl)piperazine ditrifluoroacetate
Step A: Preparation of N-Methyl-N-methoxy-2-[1-(naphth-2-ylmethyl)-1H-imidazol-5-yl)]acetamide To a solution of 2-[1-(naphth-2-ylmethyl)-1H-imidazol-5-yl]acetic acid hydrochloride (0.819 mg, 2.70 mmol) in imethylformamide (15 ml) was added sequentially N, O-imethylhydroxylamine hydrochloride (293 mg, 3.0 mmol), 3-hydroxy-1,2,3-benzotriazin-4(3H)-one (HOOBT) (489 mg, 3.0 mmol), 1-(3-dimethylaminopropyl)-3-ethylcarbodiimide hydrochloride (EDC) (575 mg, 3.0 mmol) and triethylamine (1.67 ml, 12.0 mmol). This mixture was stirred at room temperature for 18 h. After this time, sat. aq. NaHCO$_3$ (30 ml) and water (30 ml) were added and the mixture was extracted with methylene chloride (2×50 ml). The combined organic extracts were washed with brine (50 ml) and the solvent evaporated in vacuo. The residue was purified by flash chromatography eluting with 2–4% methanol/methylene chloride gradient to provide the title compound as an oil. $^1$HNMR (CDCl$_3$, 400 MHz) δ 7.80(2H, m), 7.74(1H, m), 7.56(1H, s), 7.47(3H, m), 7.22(1H, d, J=8.6 Hz), 6.97(1H, s), 5.37(2H, s), 3.58(2H, s), 3.51(3H, s) and 3.12(3H, s)ppm.
Step B: Preparation of 2-[1-(Naphth-2-ylmethyl)(1H-imidazol-5-yl)]acetaldehyde To a suspension of lithium aluminum hydride (40.8 mg, 1.07 mmol) in tetrahydrofuran (5 ml) cooled to –45° C. over a dry ice/acetone bath was added a solution of the product from Step A (243 mg, 0.895 mmol) in tetrahydrofuran (5 ml) via canula at such a rate to maintain temperature the temperature at <–35° C. After the addition was complete, the solution was allowed to warm to +5° C. and then recooled to –35° C. To this solution was added a solution of potassium bisulfate (272 mg) in water (1 ml). This mixture was stirred for 30 min at room temperature and filtered through celite. The celite pad was washed with ethyl acetate (25 ml). The combined filtrates were washed with sat. sodium bicarbonate (10 ml) and then water (10 ml). The organic layer was dried over magnesium sulfate, filtered and evaporated to give the title compound as a clear oil. $^1$HNMR (CDCl$_3$, 400 MHz) δ 9.50(1H, t, 2 Hz), 7.85–7.70(3H, m), 7.64(1H, s), 7.53–7.40(3H, m), 7.16(1H, d, J=12 Hz), 7.06(1H, s), 5.20 (2H, s) and 3.53(2H, m)ppm.
Step C: Preparation of 2(S)-Butyl-1-1-[(1-naphth-2-ylmethyl)-1H-imidazol-5-yl)ethyl]-4-(1-naphthoyl) piperazine ditrifluoroacetate To a solution of the product from Step B (58.4 mg, 0.232 mmol) and 3(S)-butyl-1-naphthoylpiperazine hydrochloride (96.5 mg, 0.279 mmol) in 1,2-dichloroethane (10 ml) and dimethylformamide (5 ml) was added 3 Å molecular sieves (250 mg) and sodium triacetoxyborohydride (236.5 mg, 1.12 mmol). This mixture was stirred at room temperature for 18 h. After this time, the mixture was filtered. The filtrate was diluted with methylene chloride (100 ml) and washed with sat sodium bicarbonate (50 ml). The organic layer was dried(MgSO$_4$), filtered and evaporated in vacuo. The residue was purified first by flash chromatography eluting with 2–5% methanol/methylene chloride and then by Prep HPLC (Chromatography A) to provide the title compound. $^1$H NMR(CD$_3$OD, 400 MHz) δ 9.04(1H, s), 8.17–7.30(15H, m), 5.65(2H, s), 4.6–2.2(11H, m) and 1.6–0.2(9H, m)ppm. FAB HRMS exact mass calc'd for C$_{35}$H$_{39}$N$_4$O 531.312387 (MH$^+$), found 531.313011.

Example 19

1-(2(R)-Amino-3-hydroypropyl)-2(S)-butyl-4-(1-naphthoyl)piperazine bis trifluoracetate salt
Step A: N-Boc-O-Benzylserine-(N'-Methoxy) methyl amide N-Boc-O-Benzylserine (Bachem; 5.0 g, 16.9 mmol) and HOBT (2.29 g, 16.9 mmol) were dissolved in dry DMF (100 mL) under argon. To this solution was added N,O-dimethylhydroxyl amine hydrochloride (1.98 g, 20.3 mmol) and then, at 0° C., EDC hydrochloride (3.56 g, 18.6 mmol). 4-Methylmorpholine was added to bring the pH to ~7 (4.5 mL) and the mixture was stirred at room temperature for 3 h. The solution was diluted with EtoAc and poured into 0.5N HCl. After extraction with EtoAc (twice), the organic layers were washed with water then brine, dried (MgSO$_4$) and evaporated in vacuo to give a pale yellow oil. Column chromatograph (silica gel; hexanel/EtoAc 2:1) gave the title compound as an oil Rf (silica; hexare/EtoAc 1:1)=0.45.
Step B: N-Boc-O-Benzyl-serine aldehyde The amide from Step A (5.7 g, 16.9 mmol) in dry ether (20 mL) was added dropwise to a suspension of LAH (0.705 g, 18.5 mmol) in 80 mL of ether at –50° C. After the addition was complete, the solution was stirred at 0° C. for 45 min. then cooled back to –50° C. and a solution of KHSO$_4$ (4 g in 11 mL H$_2$O) was added slowly. This mixture was then stirred at room temperature for 1 h, filtered through celite, washed successively with 10% citric acid solution, saturated NaHCO$_3$ solution and brine, dried (MgSO$_4$) and evaporated to give an oil which was used as such in the next step. Rf (silica; hexane/EtoAc 2:1)=0.58.
Step C: 1-(2(R)-N-Boc-Amino-3-benzyloxy propyl)-2(S)-butyl-4-(1-naphythoyl) piperazine A solution of the piperazine hydrochloride from Example 1, Step E (1.7 g, 574 mmol) in CH$_2$Cl$_2$ (25 mL) was adjusted to pH 6 using Et$_3$N then freshly ground and activated 4 Å sieves were added followed by sodium triacetoxyborohydride (4.85 g, 22.9 mmol). The aldehyde from Step B (2.08 g, 747 mmol) dissolved in 20 mL CH$_2$Cl$_2$ was added dropwise at 0° C. over 20 min. then the mixture was sitrred at room temperature for 16 h. After this time, the mixture was filtered through celite, diluted with EtoAc and washed successively with H$_2$O, KHSO$_4$, solution, NaHCO$_3$ solution and then brine. The dried (MgSO$_4$) solution was evaporated in vacuo to give a pale yellow oil which was subjected to column chromatography (silica gel; exane/EtOAc 1:1) to give the title compound as a foam. Rf (silica; exane/EtoAc 2:1)=0.15.
Step D: 1-(2(R)-N-Boc-Amino-3-hydroxy propyl)-2-(S)-butyl-4-(1-naphthoyl) piperazine The benzyl ether from Step C (700 mg, 1.25 mmol) was dissolved in 20 mL MeOH with 150 μL of acetic acid and then 20% Pd(OH)$_2$ on carbon (500 mg) was added and the mixture hydrogenated at 50 psi for 16 hr. After filtration through celite, the solvent was removed and the residue was chromatographed on silica gel (EtoAc/hexane 1:1 then 5% MeOH/EtoAc) to give the title compound as an oil.

Step E: 1-(2(R)-Amino-3-hydroxy propyl)-2(S)-butyl-4-(1-naphythoyl )piperazine bis trifluoroacetate salt A solution of the N-Boc amine from Step D (140 mg) in 10 mL EtoAc was treated with HCl (gas) until saturated. After 5 min, the solution was purged with argon then the solvent was removed to give a solid which was purified by preparative HPLC (C-18 column; H$_2$O/CH$_3$CN with 0.1% TGA; gradient). The aqueous solution was frozen and lyophilized to give the title compound as a hygroscopic powder. FAB mass spectrum m/z=370 (M+1).

Analysis calculated for C$_{22}$H$_{32}$N$_3$O$_2$.2.35 TFA C, 50.31; H, 5.27; N, 6.59 Found: C, 50.28; H, 5.49; N, 6.70

Example 20

1-(2(R)-Amino-4-hydroxybutyl)-2(S)-butyl-4-(1-naphthoyl)piperazine bishydrochloride salt Following the procedure of Example 19, Steps A to E but using N-Boc-O-benzyl homoserine (Bachem) as starting material, the title compound was obtained as the bis hydrochloride salt. FAB Mass spectrum, m/z=394 (M+1).

Analysis calculated for C$_{23}$H$_{33}$N$_3$O$_2$.1.5 HCl C, 54.04; H, 7.20; N, 8.22 Found: C, 53.95; H, 7.23; N, 8.50

Example 21

1-(2-Amino-3-(2-benzyloxyphenyl)propyl)-2(S)-butyl-4-(1-naphthoyl)piperazine bistrifluoroacetate salt Step A: D,L-N-Boc-ortho-tyrosine methyl ester The title compound was prepared as a crystalline solid from D,L-orthotyrosine (Sigma) in two steps ((Boc)$_2$O/K$_2$CO$_3$ in THF/H$_2$O followed by diazomethane in EtOAc).

Step B: 3-(2-Hydroxyphenyl)-2-(N-Boc-Amino)propanol

To a solution of the ester from Step A (1.34 g, 4.54 mmol) in THF (20 mL) at 0° C. was added LAH (400 mg, 10.5 mmol) in portions. After 4 hs at room temperature, 0.4 mL H$_2$O was added dropwise followed by 0.4 mL 1N NaOH and then 1.2 mL H$_2$O. The slurry was stirred for 1 h, filtered through (elite rinsing with THF and the solvent was removed chromatography of the residue (silica gel; hexane/EtoAc 1:1) gave the title compound as a solid. Rf (silica; hexane/EtoAc 1:1)=0.45.

Step C: 3-(2-Benzyloxyphenyl)-2-(N-Boc-amino)propanol

A mixture of the alcohol from Step B (280 mg, 1.05 mmol) benzyl bromide (150 μL, 1.26 mmol) and Cs$_2$CO$_3$ (513 mg, 1.57 mmol) in DMF (10 mL) was stirred at room temperature under argon for 16 h. The mixture was poured into H$_2$O, extracted twice with EtOAc, washed with water then brine, dried (MgSO$_4$) and evaporated to give an oil. Purification by chromatography (silica gel; hexane/EtoAc 2:1) gave the title compound as an oil. Rf (silica; hexane/EtoAc 2:1)=0.36.

Step D: 3-(2-Benzyloxyphenyl)-2-(N-Boc-amino)propanol

To a solution of the alcohol from Step C (280 mg, 0.78 mmol) in 3 mL DMSO, 3 mL CH$_2$Cl$_2$ and 0.55 mL Et$_3$N at room temperature under argon was added pyridine SO$_3$ complex (500 mg, 3.14 mmol) and the mixture stirred for 1 h. The solution was poured into saturated NaHCO$_3$ solution, extracted twice with EtoAc, washed with water then brine, dried (MgSO$_4$) and concentrated in vacuo. The title compound was thus obtained as an oil and was used as such in the following step. Rf (silica; hexane/EtoAc 4:1)=0.41.

Step E: 1-(2-N-Boc-Amino-3-(2-benzyloxyphenyl)propyl)-2(S)-butyl-4-(1-naphthoyl)piperazine The aldehyde from Step D and the piperazine hydrochloride from Example 1, Step E were coupled via reductive alkyltion using the procedure described for Example 19, Step C. Purification by column chromatgraphy (silica gel; hexane/EtoAc 3:2) gave the title compound as a 1:1 mixture of diastereomers. Rf (silica; hexane/EtOAc 1:1)=0.51 and 0.45.

Step F: 1-(2-Amino-3-(2-benzyloxyphenyl)propyl)-2(S)-butyl-4-(1-naphthoyl)piperazine bis trifluoroacetate salt A solution of the N-Boc amine from Step E (70 mg) in EtOAc (15 mL) was treated with HCl (g) until saturated. After 15 min., the solution was purged with argon and then the solvent removed to yield a solid. Purification by preparative HPLC (C-18 column, H$_2$O/CH$_3$CN with 0.1% TFA; gradient) afforded (after lyophilization) the title compound as a powder. FAB mass spectrum, m/z=536 (M+1).

Analysis calculated for C$_{35}$H$_{41}$N$_3$O$_2$.2.2 TFA.0.35 H$_2$O C, 59.68; H, 5.58; N, 5.30 Found: C, 59.70; H, 5.60; N, 5.56

Example 22

1-(2-Amino-3-(2-hydroxyphenyl)propyl)-2(S)-butyl-4-(1-naphthoyl)piperazine bis trifluoroacetate salt, diastereomer A Step A: 1-(2-N-Boc-Amino-3-(2-hydroxyphenyl)propyl)-2(S)-butyl-4-(1-naphthoyl)piperazine A mixture of 1-(2-N-Boc-Amino-3-(2-benzyloxy-phenyl)propyl)-2(S)-butyl-4-(1-naphthoyl)piperazine (from Example 19, Step E; 290 mg, 0.5 mmol), acetic acid (60 μL, 1.0 mmol) and 20% Pd(OH)$_2$ on carbon (100 mg) in MeOH (20 mL) was hydrogenated at 67 psi for 5 h. The solution was filtered through celite and the solvent evaporated to give an oil which showed 2 well resolved spots on silica tic. Column chromatography (silica gel; hexane:EtoAc 1:1) gave:

a) diastereomer A of the title compound RF (silica; hexane/EtoAc 1:1)=0.49.

b) diastereomer B of the title compound RF (silica; hexane/EtoAc 1:1)=0.35.

Step B: 1-(2-Amino-3-(2-hydroxyphenyl)propyl)-2(S)-butyl-4-(1-naphthoyl)piperazine bis trifluoroacetate salt, diastereomer A The N-Boc amine, diastereomer A from Step A, was deprotected using HCl (gas) in EtoAc. Removal of the solvent followed by preparative HPLC (C-18 column; H$_2$O/CH$_3$CN with 0.1% TFA; gradient) gave (after lyophilization) the title compound as a powder. FAB mass spectrum, m/z=446 (M+1).

Analysis calculated for C$_{28}$H$_{35}$N$_3$O$_2$.2 TFA C, 57.05; H, 5.54; N, 6.24 Found: C, 57.08; H, 5.64; N, 6.32

Example 23

1-[3-(4-imidazolyl)propyl]-2(S)-butyl-4-(1-naphthoyl)piperazine bis trifluoroacetate salt Step A: Ethyl 3-(4-imidazolyl)propionate The title compound was prepared from urocanic acid (Aldrich) in 2 steps using standard chemical procedures (esterification using HCl in EtOH followed by hydrogenation with 10% Pd-C in EtOH). $^1$H NMR (CDCl$_3$): δ 1.23 (3H, t), 2.65 (2H, t), 2.94 (2H, t), 4.15 (2H, q), 6.81 (1H, S), 7.56 (1H, s).

Step B: 3-(4-imidazolyl) propanol

To a solution of the ester from Step A (120 g, 71.4 mmol) in dry THF (230 mL) at 0° C. was added LAH (2.99 g, 78.6 mmol) portionwise over 30 min. The mixture was stirred for 2 h at room temperature then cooled back to 0° C. and H$_2$O (4.2 mL) was added (care!) dropwise. This was followed by the dropwise addition of 10.6 mL of 1N NaOH then the resulting slurry was stirred at room temperature for 1 h. After filtration through celite washing with EtOAc, the solvent was removed to give the title compound as a clear oil (8.16 g). $^1$H NMR (CD$_3$OD): δ 1.84 (2H, pentet), 2.68 (2H, t), 3.58 (2H, t), 6.88 (1H, s), 7.80 (1H, s).

Step C: 3-(4-N-BOC-imidazolyl)propanol

The imidazole from Step B (166 mg, 1.32 mmol), (Boc)$_2$O (302 mg, 1.38 mmol) and K$_2$CO$_3$ (190 mg, 1.38 mmol) were stirred in THF (10 mL) for 2 h. After filtration, the solvent was removed in vacuo to give the desired compound as an oil. Rf (silica; 5% MeOH/CHCl$_3$)=0.17. This was used as such in the next step.

Step D: 1-[3-(4-imidazolyl)propyl]-2(S)-butyl-4-(1-naphthoyl) piperazine bis trifluoroacetate salt The alcohol from Step C (~1.32 mmol) was dissolved in 4 mL DMSO, 4 mL CH$_2$Cl$_2$ and 0.92 mL Et$_3$N and then pyridine SO$_3$ complex (600 mg, 5.28 mmol) was added in portions. After 3 h, the mixture was poured into EtOAc, extracted with saturated NaHCO$_3$ solution then brine, dried and evaporated to afford the corresponding aldehyde which was used without further purification.

This aldehyde was coupled with the piperazine from Example 1, Step E by reductive alkylation following the procedure described for Example 19, Step C and the product was obtained by column chromatography (silica gel; 5% MeOH/CHCl$_3$). This product was dissolved in 10 mL EtOAc saturated with HCl (gas). The solvent was removed and the residue purified by preparative HPLC (C-18; H$_2$O/CH$_3$CN with 0.1% TFA; gradient). Lyophilization of the frozen aqueous solution gave the title compound as a hygroscopic powder. FAB mass spectrum, m/z=405 (M+1).

Analysis calculated for C$_{25}$H$_{32}$N$_4$O.2.35 TFA 0.4 H$_2$O C, 52.48; H, 5.21; N, 8.24 Found: C, 52.45; H, 5.22; N, 8.27

Example 24

2(S)-n-Butyl-4-(1-naphthoyl)-1-[1-(1-naphtliylmethyl)imidazol-5-ylmethyl]-piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 1-bromomethylnaphthalene (0.046 g, 0.21 mmol) according to the procedure described in Example 4. The title compound was obtained after purification by reverse phase preparative HPLC (gradient elution with 30%–75% acetonitrile/0.1% TFA; 70%–25% 0.1% aqueous TFA over 50 min.) and lyophilization. FAB ms (m+1) 517. Anal. Calc. for C$_{34}$H$_{36}$N$_4$O.0.05 H$_2$O.2.0 TFA: C, 60.55; H, 5.22; N, 7.43. Found: C, 60.48; H, 5.12; N, 7.42.

Example 25

2(S)-n-Butyl-4-(1-naphthoyl)-1-[1-(2-naphthylmethyl)imidazol-5-ylmethyl]-piperazine ditrifluoroacetic acid salt The title compound was prepared from 2(S)-n-butyl-1-[5-(3-triphenylmethytimidazolyl)methyl]-4-(1-naphthoyl) piperazine (0.124 g, 0.200 mmol) and 2-bromomethylnaphthalene (0.046 g, 0.21 mmol) according to the procedure described in Example 4. The title compound was obtained after purification by reverse phase preparative HPLC (gradient elution with 30%–75% acetonitrile/0.1% TFA; 70%–25% 0.1% aqueous TFA over 50 min.) and lyophilization. FAB ms (m+1) 517. Anal. Calc. for C$_{34}$H$_{36}$N$_4$O.1.7 H$_2$O.2.0 TFA: C, 58.87; H, 5.38; N, 7.23. Found: C, 58.90; H, 4.93; N, 7.13.

Example 26

2(S)-n-Butyl-1-1-[1-(4-cyanobenzyl)imidazol-5-ylmethyl]-4-(1-naphthoyl)piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 4-cyanobenzylbromide (0.041 g, 0.21 mmol) according to the procedure described in Example 4. The title compound was obtained after purification by reverse phase preparative HPLC (gradient elution with 25%–65% acetonitrile/0.1% TFA; 75%–35% 0.1% aqueous TFA over 50 min.) and lyophilization. FAB ms (m+1) 492. Anal. Calc. for C$_{31}$H$_{33}$N$_5$O.0.35 H$_2$O.2.0 TFA: C, 57.91; H, 4.96; N, 9.65. Found: C, 57.93; 11, 4.91; N, 9.55.

Example 27

(S)-n-Butyl-1-[1-(4-methoxybenzyl)imidazol-5-ylmethyl]-4-(1-aphthoyl)piperazine ditrifluoroacetic acid salt The title compound was prepared from 2(S)-n-butyl-1-[5-3-triphenylmethylimidazolyl)methyl]-4-(1-naphthoyl) piperazine (0.124 g, 0.200 mmol) and 4-methyoxybenzylchloride (0.041 mL, 0.21 mmol) according to the procedure described in Example 4, with the addition of potassium iodide (100 mg) to the reaction mixture. The title compound was obtained after purification by reverse phase preparative HPLC (gradient elution with 25%–65% acetonitrile/0.1% TFA; 75%–35% 0.1% aqueous TFA over 50 min.) and lyophilization. FAB ms (m+1) 497. Anal. Calc. for C$_{31}$H$_{36}$N$_4$O$_2$. 1.7 H$_2$O.2.0 TFA: C, 53.40; H, 5.30; N, 7.12. Found: C, 53.37; H, 4.78; N, 7.00.

Example 28

2(S)-n-Butyl-1-[1-(3-methyl-2-butenyl)imidazol-5-ylmethyl]-4-(1-naphthoyl)piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 4-bromo-2-methyl-2-butene (0.024 mL, 0.21 mmol) according to the procedure described in Example 4. The title compound was obtained after purification by reverse phase preparative HPLC (gradient elution with 5%–95% acetonitrile/0.1% TFA; 95%–5% 0.1% aqueous TFA over 50 min.) and lyophilization. FAB ms (m+1) 445. Anal. Calc. for C$_{28}$H$_{36}$N$_4$O.1.8 H$_2$O.2.0 TFA: C, 54.51; H, 5.95; N, 7.95. Found: C, 54.54; H, 5.39; N, 7.73.

Example 29

2(S)-n-Butyl-1-[1-(4-fluorobenzyl)imidazol-5-ylmethyl]-4-(1-naphthoyl)piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 4-fluorobenzylbromide (0.026 mL, 0.21 mmol) according to the procedure described in Example 4. The title compound was obtained after purification by reverse phase preparative HPLC (gradient elution with 25%–65% acetonitrile/0.1% TFA; 75%–35% 0.1% aqueous TFA over 50 min.) and lyophilization. FAB ms (m+1) 495. Anal. Calc. for $C_{30}H_{33}FN_4O.3.0\ H_2O.2.0$ TFA: C, 53.26; H, 5.39; N, 7.31. Found: C, 53.21; H, 4.56; N, 7.08.

Example 30

2(S)-n-Butyl-1-[1-(4-chlorobenzyl)imidazol-5-ylmethyl]-4-(1-naphthoyl)piperazine ditrifluoroacetic acid salt The title compound was prepared from 2(S)-n-butyl-1-[5-(3-triphenylmethylimidazolyl)methy]-4-(1-naphthoyl) piperazine (0.124 g, 0.200 mmol) and 4-chlorobenzylchloride (0.034 mg, 0.21 mmol) according to the procedure described in Example 4, with the addition of sodium iodide (100 mg) to the reaction mixture. The title compound was obtained after purification by reverse phase preparative HPLC (gradient elution with 25%–65% acetonitrile/0.1% TFA; 75%–35% 0.1% aqueous TFA over 50 min.) and lyophilization. FAB ms (m+1) 501. Anal. Calc. for $C_{30}H_{33}ClN_4O.4.8\ H_2O.2.0$ TFA: C, 50.07; H, 5.51; N, 6.87. Found: C, 50.10; H, 4.25; N, 6.48.

Example 31

1-[1-(4-Bromobenzyl)imidazol-5-ylmethyl]2(S)-n-butyl-4-(1-naphthoyl)piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 4-bromobenzylbromide (0.053 mg, 0.21 mmol) according to the procedure described in Example 4, with the addition of sodium iodide (100 mg) to the reaction mixture. The title compound was obtained after purification by reverse phase preparative HPLC (gradient elution with 30%–65% acetonitrile/0. 1% TFA; 70%–35% 0.1% aqueous TFA over 50 min.) and lyophilization. FAB ms (m+1) 545. Anal. Calc. for $C_{30}H_{33}BrN_4O.1.7\ H_2O.2.0$ TFA: C, 50.78; H, 4.81; N, 6.97. Found: C, 50.81; H, 4.39; N, 6.88.

Example 32

2(S)-n-Butyl-4-(1-naphthoyl)-1-[1-(4-trifluoromethylbenzyl)imidazol-5-ylmethyl]-piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 4-trifluoromethylbenzylbromide (0.053 mg, 0.21 mmol) according to the procedure described in Example 4. The title compound was obtained after purification by reverse phase preparative HPLC (gradient elution with 30%–65% acetonitrile/0.1% TFA; 70%–35% 0.1% aqueous TFA over 50 min.) and lyophilization. FAB ms (m+1) 535. Anal. Calc. for $C_{30}H_{33}BrN_4O.2.0$ TFA: C, 55.12; H, 4.63; N, 7.35. Found: C, 57.46; H, 4.98; N, 7.84.

Example 33

2(S)-n-Butyl-1-[1-(4-methylbenzyl)imidazol -5-ylmethyl]-4-(1-naphthoyl)-piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 4-methylbenzylbromide (0.029 mL, 0.21 mmol) according to the procedure described in Example 4, with the addition of sodium iodide (100 mg) to the reaction mixture. The title compound was obtained after purification by reverse phase preparative HPLC (gradient elution with 30%–65% acetonitrile/0.1% TFA; 70%–35% 0.1% aqueous TFA over 50 min.) and lyophilization. FAB ms (m+1) 481. Anal. Calc. for $C_{31}H_{36}N_4O.2.6\ H_2O.2.0$ TFA: C, 55.64; H, 5.76; N, 7.42. Found: C, 55.61; H, 5.09; N, 7.43.

Example 34

2(S)-n-Butyl-1-[1-(3-methylbenzyl)imidazol-5-ylmethyl]4-(1-naphthoyl)-piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 3-methylbenzylbromide (0.029 mL, 0.21 mmol) according to the procedure described in Example 4. The title compound was obtained after purification by reverse phase preparative HPLC (gradient elution with 25%–65% acetonitrile/0.1% TFA; 75%–35% 0.1% aqueous TFA over 50 min.) and lyophilization. FAB ms (m+1) 481. Anal. Calc. for $C_{31}H_{36}N_4O.2.0$ TFA: C, 67.26; H, 6.92; N, 10.12. Found: C, 69.60; H, 6.98; N, 10.51.

Example 35

1-[1-(4-Phenylbenzyl)imidazol-5-ylmethyl]-2(S)-n-butyl-4-(1-naphthoyl)-piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 4-phenylbenzylbromide (0.029 mL, 0.21 mmol) according to the procedure described in Example 4. The title compound was obtained after purification by reverse phase preparative HPLC (gradient elution with 30%–65% acelonitrile/0.1% TFA; 70%–35% 0.1% aqueous TFA over 50 min.) and iyophilization. FAB ms (m+1) 543. Anal. Calc. for $C_{36}H_{38}N_4O.4.95\ H_2O.2.0$ TFA: C, 55.87; H, 5.85; N, 6.52. Found: C, 55.55; H, 4.58; N, 6.23.

Example 36

2(S)-n-Butyl-4-(1-naphthoyl)-1-[1-(2-phenylethyl)imidazol-5-ylmethyl]-piperazine ditrifluoroacetic acid salt The title compound was prepared from 2(S)-n-butyl-1-[5-(3-triphenylmethylimidazolyl)methyl]-4-(1-naphthoyl) piperazine (0.124 g, 0.200 mmol) and 2-phenylethylbromide (0.029 mL, 0.21 mmol) according to the procedure described in Example 4, except with the addition of sodium iodide (120 mg) and refluxing for 12 h. The title compound was obtained after purification by reverse phase preparative HPLC (gradient elution with 30%–65% acetonitrile/0.1% TFA; 70%–35% 0.1% aqueous TFA over 50 min.) and lyophilization. FAB ms (m+1) 481. Anal. Calc. for $C_{36}H_{38}N_4O.4.20\ H_2O.2.0$ TFA: C, 53.60; H, 5.96; N, 7.14. Found: C, 53.54; H, 4.86; N, 6.86.

Example 37

2(S)-n-Butyl-4-(1-naphthoyl)-1-[1-(4-trifluoromethoxy)imidazol-5-ylmethyl]piperazine ditrifluoroacetic acid salt The title compound was prepared from 2(S)-n-butyl-1-[5-(3-triphenylmethylimidazolyl)methyl]-4-(1-naphthoyl)

piperazine (0.124 g, 0.200 mmol) and 4-trifluoromethoxybenzylbromide (0.032 mL, 0.21 mmol) according to the procedure described in Example 4, except with the addition of sodium iodide (120 mg) and refluxing for 12 h. The title compound was obtained after purification by reverse phase preparative HPLC (gradient elution with 35%–70% acetonitrile/0.1% TFA; 65%–30% 0.1% aqueous TFA over 50 min.) and lyophilization. FAB ms (m+1) 551. Anal. Calc. for $C_{31}H_{33}F_3N_4O_2 \cdot 4.00\ H_2O \cdot 2.0\ TFA$: C, 49.42; H, 5.09; N, 6.59. Found: C, 48.95; H, 4.06; N, 6.26.

Example 38

Preparation of 1-{[1-(4-cyanobenzyl)-1H-imidazol-5-yl]acetyl}-2(S)-n-butyl-4-(1-naphthoyl)piperazine trifluoroacetate Step A: Preparation of 1H-Imidazole-4-acetic acid methyl ester hydrochloride.

A solution of 1H-imidazole-4-acetic acid hydrochloride 4.00 g, 24.6 mmol) in methanol (100 ml) was saturated with gaseous hydrogen chloride. The resulting solution was allowed to stand at room temperature (RT) for 18 hr. The solvent was evaporated in vacuo to afford the title compound as a white solid. $^1H\ NMR(CDCl_3,\ 400\ MHz)$ δ 8.85(1H, s), 7.45(1H, s), 3.89(2H, s) and 3.75(3H, s) ppm.

Step B: Preparation of 1-(Triphenylmethyl)-1H-imidazol-4-ylacetic acid methyl ester.

To a solution of the product from Step A (24.85 g, 0.141 mol) in dimethyl formamide (DMF) (115 ml) was added triethylamine (57.2 ml, 0.412 mol) and triplhenylmethyl bromide(55.3 g, 0.171 mol) and the suspension was stirred for 24 hr. After this time, the reaction mixture was diluted with ethyl acetate (EtOAc) (1 L) and water (350 ml). The organic phase was washed with sat. aq. $NaHCO_3$ (350 ml), dried ($Na_2SO_4$) and evaporated in vacuo. The residue was purified by flash chromatography ($SiO_2$, 0–100% ethyl acetate in hexanes; gradient elution) to provide the title compound as a white solid. $^1H\ NMR(CDCl_3,\ 400\ MHz)$ δ 7.35(1H, s), 7.31(9H, m), 7.22(6H, m), 6.76(1H, s), 3.68 (3H, s) and 3.60(2H, s) ppm.

Step C: Preparation of [1-(4-cyanobenzyl)-1H-imidazol-5-yl]acetic acid methyl ester.

To a solution of the product from Step B (8.00 g, 20.9 mmol) in acetonitrile (70 ml) was added bromo-p-toluonitrile (4.10 g, 20.92 mmol) and heated at 55° C. for 3 hr. After this time, the reaction was cooled to room temperature and the resulting imidazolium salt (white precipitate) was collected by filtration. The filtrate was heated at 55° C. for 18 hr. The reaction mixture was cooled to room temperature and evaporated in vacuo. To the residue was added EtOAc (70 ml) and the resulting white precipitate collected by filtration. The precipitated imidazolium salts were combined, suspended in methanol (100 ml) and heated to reflux for 30 min. After this time, the solvent was removed in vacuo, the resulting residue was suspended in EtOAc (75 ml) and the solid isolated by filtration and washed (EtOAc). The solid was treated with sat aq $NaHCO_3$ (300 ml) and $CH_2Cl_2$ (300 ml) and stirred at room temperature for 2 hr. The organic layer was separated, dried ($MgSO_4$) and evaporated in vacuo to afford the title compound as a white solid: $^1HNMR(CDCl_3,\ 400\ MHz)$ δ 7.65(1H, d, J=8 Hz), 7.53(1H, s), 7.15(1H, d, J=8 Hz), 7.04(1H, s), 5.24(2H, s), 3.62(3H, s) and 3.45(2H, s) ppm.

Step D: Preparation of [1-(4-cyanobenzyl)-1H-imidazol-5-yl]acetic acid

A solution of [1-(4-cyanobenzyl)-1H-imidazol-5-yl] acetic acid methyl ester (4.44 g, 17.4 mmol ) in THF (100 ml) and 1M lithium hydoxide (17.4 ml, 17.4 mmol) was stirred at RT for 18 hr. 1M HCl (17.4 ml) was added and the THF was removed by evaporation in vacuo. The aqueous solution was lyophilised to afford the title compound containing lithium chloride as a white solid. $^1H\ NMR(CD_3OD,\ 400\ MHz)$ δ 8.22(1H, s), 7.74(1H, d, J=8.4 Hz), 7.36(1H, d, J=8.4 Hz), 7.15(1H, s), 5.43(2H, s) and 3.49(2H, s) ppm.

Step E: Preparation of 1-{[1-(4-cyanobenzyl)-1H-imidazol-5-yl]acetyl}-2(S)-n-butyl-4-(1-naphthoyl)piperazine trifluoroacetate To a solution of the acid from step D (100 mg, 0.35 mmol), the amine hydrochloride salt from example step (117 mg, 0.35 mmol), HOOBT (58 mg, 0.35 mmol), and triethylamine (0.123 ml, 0.88 mmol) in DMF (2 ml) was added EDC (75 mg, 0.38 mmol). The reaction was stirred at room temperature for 16 hrs, diluted with EtOAc and the organic layer washed with sat. aq $NaHCO_3$, brine, dried ($Na_2SO_4$). and evaporated in vacuo. The residue was purified by preparative HPLC (C-18; 95:5 to 5:95 water:$CH_3CN$ containing 0.1% trifluoroacetic acid; gradient elution). Lyophilisation of the collected fractions afforded the title compound as a white solid. $^1H\ NMR(CD_3OD,\ 400\ MHz)$ δ 9.00–8.90(1H, m), 8.05–7.94(2H,m), 7.94–7.40(10H,m), 5.60–5.40(2H,m), 5.00–2.80(9H,m), 1.90–1.15(4H,m) and 1.05–0.40(5H, m)ppm. Anal. calc'd for $C_{32}H_{33}N_5O_2$ 1.40 TFA; $0.55H_2O$: C, 60.65; H, 5.19; N, 10.16. Found: C, 60.66; H, 5.17; N, 10.06.

Example 39

5(S)-n-Butyl-1-(2,3-dimethylphenyl)-4-(4-imidazolylmethyl)piperazin-2-one ditrifluoroacetic acid salt Step A: N-Methoxy-N-methyl 2(S)-(tert-butoxycarbonylamino) hexanamide 2(S)-(tert-Butoxycarbonylamino)hexanoic acid (24.6 g, 0.106 mol), N,O-dimethylhydroxylamine hydrochloride (15.5 g, 0.15 mol), EDC hydrochloride (22.3 g, 0.117 mol) and HOBT (14.3 g, 0.106 mol) were stirred in dry, degassed DMF (300 mL) at 20° C. under nitrogen. N-Methylmorpholine was added to obtain pH 7. The reaction was stirred overnight, the DMF distilled under high vacuum, and the residue partitioned between ethyl acetate and 2% potassium hydrogen sulfate. The organic phase was washed with saturated sodium bicarbonate, water, and saturated brine, and dried with magnesium sulfate. The solvent was removed in vacuo to give the title compound.

Step B: 2(S)-(tert-Butoxycarbonylamino)hexanal

A mechanically stirred suspension of lithium aluminum hydride (5.00 g, 0.131 mol) in ether (250 mL) was cooled to −45° C. under nitrogen. A solution of the product from Step A (28.3 g, 0.103 mol) in ether (125 mL) was added, maintaining the temperature below −35° C. When the addition was complete, the reaction was warmed to 5° C., then recooled to −45° C. A solution of potassium hydrogen sulfate (27.3 g, 0.200 mol) in water was slowly added, maintaining the temperature below −5° C. After quenching, the reaction was stirred at room temperature for 1 h. The mixture was filtered through Celite, the ether evaporated, and the remainder partitioned between ethyl acetate and 2% potassium hydrogen sulfate. After washing with saturated brine, drying over magnesium sulfate and solvent removal, the title compound was obtained.

Step C: N-(2,3-Dimethylphenyl)-2(S)-(tert-butoxycarbonylamino) hexanamine 2,3-Dimethylaniline (8.32 mL, 68.3 mmol) was dissolved in dichloroethane under nitrogen. Acetic acid was added to obtain pH 5, and sodium triacetoxyborohydride (17.2 g, 80.8 mmol) and crushed molecular sieves (4 g) were added. A solution of the product from Step B (13.3 g, 62.1 mmol) in dichloroethane (80 mL) was added slowly dropwise at 20° C. The reaction was stirred overnight, then quenched with saturated sodium bicarbonate solution. The aqueous layer was removed, the organic phase washed with saturated brine and dried over magnesium sulfate. Crystallization from hexane gave the title compound.

Step D: 4-tert-Butoxycarbonyl-5(S)-n-butyl-1-(2,3-dimethylphenyl)piperazin-2-one A solution of the product from Step C (8.50 g, 26.5 mmol) in ethyl acetate (250 mL) was vigorously stirred at 0° C. with saturated sodium bicarbonate (150 mL). Chloroacetyl chloride (2.33 mL, 29.1 mmol) was added, and the reaction stirred at ) 0° C. for 1 h. The layers were separated, and the ethyl acetate phase was washed with saturated brine, and dried over magnesium sulfate. The crude product was dissolved in DMF (300 mL) and cooled to 0° C. under nitrogen. Sodium hydride (1.79 g, 60% dispersion in oil, 44.9 mmol) was added portionwise to maintain moderate hydrogen evolution. After 30 min, an additional amount of sodium hydride was added (0.8 g). The reaction was stirred another 30 min, then quenched with saturated ammonium chloride. The DMF was distilled in vacuo, and the residue partitioned between ethyl acetate and water. The organic phase was washed with water, saturated brine, and dried over magnesium sulfate. The crude product was chromatographed on silica gel with 20–30% ethyl acetate in hexane to obtain the title compound.

Step E: 5(S)-n-Butyl-1-(2,3-dimethylphenyl)-4-[4-(1-triphenylmethylimidazolyl)methyl]pilperazin-2-one A solution of the product from Step D (0.570 g, 1.58 mmol) in ethyl acetate (50 mL) was cooled to −15° C. under nitrogen. HCl gas was bubbled through for 15 min, and the reaction solution warmed to 0° C. for 2 h. The solvent was removed in vacuo, and the resulting solid was dissolved in dichloroethine (20 mL). Sodium triacetoxyborohydride (0.502 g, 2.37 mmol) and 1-triphenylmethyl-4-imidazolyl carboxaldehyde (0.534 g, 1.58 mmol) was added. The reaction was stirred overnight at 20° C. then poured into saturated sodium bicarbonate solution. The organic phase was washed with saturated brine and dried over magnesium sulfate. Silica gel chromatography using 4% methanol in dichloromethane as eluant yielded the title compound.

Step F: 5(S)-n-Butyl-1-(2,3-dimethylphenyl)-4-(4-imidazolylmethyl)piperazin-2-one ditrifluoroacetic acid salt To a solution of the compound from Step E (0.233 g, 0.40 mmol) in dichloromethane (6 mL) was added triethylsilane (0.254 mL) and trifluoroacetic acid (2 mL) were added, and the reaction stirred at 20° C. for 2 h. The volatiles were removed in vacuo, and the residue partitioned between hexane and water-methanol. The aqueous phase was injected onto a preparative HPLC column and purified with a mixed gradient of 15%–60% acetonitrile/0.1% TFA; 85%–40% 0.1% aqueous TFA over 50 min. The title compound was isolated after lyophilization. FAB ms (m+1) 341. Anal. Calc. for $C_{20}H_{28}N_4O.2.0$ TFA: C, 50.80; H, 5.15; N, 9.87. Found: C, 51.31; H, 5.41; N, 10.11.

Example 40

5(S)-n-Butyl-4-[1-(4-cyanobenzyl)imidazol-5-ylmethyl]-1-(2,3-dimethylphenyl)piperazin-2-one ditrifluoroacetic acid salt 4-Cyanobenzylbromide (0.043 g, 0.22 mmol) was added at 20° C. to a solution of 5(S)-n-butyl-1-(2,3-dimethylphenyl)-4-[4-(1-triphenylmethylimidazolyl) methyl]piperazin-2-one (0.120 g, 0.21 mmol) from Example 39, Step E, in acetonitrile (10 mL). After 48 h, the solvent was removed in vacuo, and the crude product dissolved in dichloromethane (6 mL). Triethylsilane (0.13 mL) and trifluoroacetic acid (2 mL) were added, and the reaction stirred at 20° C. for 2 h. The volatiles were removed in vacuo, and the residue partitioned between hexane and water-methanol. The aqueous phase was injected onto a reverse phase preparative HPLC column and purified with a mixed gradient of 30%–60% acetonitrile/0.1% TFA; 70%–40% 0.1% aqueous TFA over 50 min. The title compound was isolated after lyophilization from water-acetonitrile solution. FAB ms (m+1) 456. Anal. Calc. for $C_{28}H_{33}N_5O.0.7\ H_2O.2.0$ TFA: C, 55.28; H, 5.13; N, 10.07. Found: C, 55.27; H, 5.20; N, 10.41.

Example 41

4-[1-(4-Cyanobenzyl)imidazol-5-ylmethyl]-1-(2,3-dimethylphenyl)-5(S)-(2-methoxyethyl)piperazin-2-one ditrifluoroacetic acid salt Step A: N-Methoxy-N-methyl 4-benzyloxy-2(S)-(tert-butoxycarbonylamino)butanamide 4-Benzyloxy-2(S)-(tert-butoxycearbonylamino)butanoic acid (1.00 g, 3.23 mmol) was converted to the title compound following the procedure described in Example 39, Step A, using EDC.HCl (0.680 g, 3.55 mmol). HOBT (0.436 g, 3.23 mmol) and N,O-dimethylhydroxylamine hydrochloride (0.473 g, 4.85 mmol) in DMF (50 mL) at pH 7. After workup, the title compound was obtained as a clear gum.

Step B: 4-(1-Benzyloxyethyl)-2(S)-(tert-butoxycarbonylamino) butanal

The title compound was obtained by lithium aluminum hydride reduction of the product of Step A using the procedure described in Example 39, Step B.

Step C: N-(2,3-Dimethylphenyl)-4-(2-benzyloxyethyl)-2-(S)-(tert-butoxycarbonylamino)butanamnine The title compound was prepared from the product of Step C according to the procedure described in Example 39, Step B, using 2,3-dimethylaniline (0.505 mL, 4.14 mmol), sodium triacetoxyborohydride (1.20 g, 5.65 mmol) and crushed molecular sieves (1 g) at pH 5 in dichloroethane (20 mL). The title compound was obtained after purification on silica gel, eluting with 15% ethyl acetate in hexane.

Step D: 5(S)-(2-Benzyloxyethyl)-4-tert-butoxycarbonyl-1-(2,3-dimethylphenyl)piperazin-2-one The title compound was prepared from the product of Step C according to the procedure described in Example 39, Step D, using chloroacetyl chloride (0.21 mL, 2.57 mmol) in 60 mL 1:1 ethyl acetate:saturated sodium bicarbonate, followed by reaction of the crude product with sodium hydride (0.373 g, 60% dispersion in oil, 9.32 mmol) in DMF (30 mL). After workup, the crude product was chromatographed on silica gel with 30% ethyl acetate in hexane to obtain the title compound.

Step E: 4-tert-Butoxycarbonyl-1-(2,3-dimethylphenyl)-5(S)-(2-hydroxyethyl)piperazin-2-one The product from Step D was dissolved in methanol (40 mL) and 10% Pd/C was added (0.160 g). The reaction was shaken under 60 psi hydrogen overnight. The catalyst was removed by filtration, and the solvent evaporated to give the title compound.

Step F: 4-tert-Butoxycarbonyl-1-(2,3-dimethylphenyl)-5(S)-(2-methoxyethyl)piperazin-2-one The product from Step E (0.241 g, 0.699 mmol) was dissolved in DMF (10 mL) containing methyl iodide (0.21 mL, 3.44 mmol) and the stirred solution cooled to 0° C. under nitrogen. Sodium hydride (0.070 g, 60% dispersion in oil, 1.72 mmol) was added and the reaction stirred for 1 h.

The reaction was quenched with water, and the DMF removed under vacuum. The residue was partitioned between ethyl acetate and water, and the organic phase washed with saturated brine and dried over magnesium sulfate. The crude product was chromatographed on silica gel with 40% ethyl acetate in hexane to give the title compound.

Step G: 1-(2,3-Dimethylphenyl)-5(S)-(2-methoxyethyl)-4-[4-(1-triphenylmethylimidazolyl)methyl]piperazin-2-one The product from Step F (0.113 g, 0.312 mmol) was converted to the title compound according to the procedure described in Example 39, Step E, except using 30% trifluoroacetic acid in dichloromethane (10 mL) for 1 h for the initial deprotection. The volatiles were removed in vacuo, and the residue dissolved in dichloroethane. Triethylamine was added to obtain pH 5. Sodium triacetoxyborohydride (0.100 g, 0.468 mmol) and 1-triphenylmethyl-4-imidazolylcarboxaldehyde (0.1164 g, 0.343 mmol) was added. The reaction was stirred overnight at 20° C. then poured into saturated sodium bicarbonate solution. The organic phase was washed with saturated brine and dried over magnesium sulfate. Silica gel chromatography using 5% methanol in chloroform as eluant yielded the title compound.

Step H: 4-[1-(4-Cyanobenzyl)imidazol-5-ylmethyl]-1-(2,3-dimethylphenyl)-5(S)-(2-methoxyethyl)piperazin-2-one ditrifluoroacetic acid salt The product from Step G (0.182 g, 0.312 mmol) was converted to the title compound according to the procedure described in Example 40, using 4-cyanobenzylbromide (0.061 g, 0.312 mmol) in acetonitrile (10 mL), followed by reaction of the crude imidazolium salt with triethylsilane (0.13 mL) and trifluoroacetic acid (2 mL) in dichloromethane (6 mL). Purification was accomplished by reverse phase preparative HPLC with a mixed gradient of 0%–70% acetonitrile/0.1% TFA; 100%–30% 0.1% aqueous TFA over 60 min. The title compound was isolated after lyophilization from water. FAB ms (m+1) 458. Anal. Calc. for $C_{27}H_{31}N_5O_2 \cdot 0.35\ H_2O \cdot 2.0$ TFA: C, 53.81; H, 4.91; N, 10.21. Found: C, 53.83; H, 4.95; N, 10.29.

Example 42

Preparation of (S)-1-(3-chlorophenyl)-4-[1-(4-cyanobenzyl)-5-imidazolylmethyl]-5-[2-(methanesulfonyl)ethyl]-2-piperazinone dihydrochloride Step A: Preparation of 1-triphenylmethyl-4-(hydroxymethyl) imidazole To a solution of 4-(hydroxymethyl)imidazole hydrochloride (35.0 g, 260 mmol) in 250 ml, of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO₃, and brine, then dried (Na₂SO₄), filtered, and concentrated in vacuo to provide the crude product. The acetate was isolated as a white powder which was sufficiently pure for use in the next reaction.

Step C: Preparation of 1-(4-cyanobenzyl)-5-(acetoxymethyl)-imidazole hydrobromide A solution of the product from Step B (85.8 g, 225 mmol) and (α-bromo-p-tolunitrile (50.1 g, 232 mmol) in 500 mL of EtOAc was stirred at 60° C. for 20 hours, during which at pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: Preparation of 1-(4-cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. NaHCO₃ and brine. The solution was then dried (Na₂SO₄), filtered, and concentrated in vacuo to provide the crude product as a pale yellow fluffy solid which was sufficiently pure for use in the next step without further purification.

Step E: Preparation of 1-(4-cyanobenzyl)-5-imidazolecarboxaldehyde

To a solution of the alcohol from Step D (21.5 g, 101 mmol) in 500 mL of DMSO at room temperature was added triethylamine (56 mL, 402 mmol), then SO₃-pyridine complex (40.5 g, 254 mmol). After 45 minutes, the reaction was poured into 2.5 L of EtOAc, washed with water (4×1 L) and brine, dried (Na₂SO₄), filtered, and concentrated in vacuo to provide the aldehyde as a white powder which was sufficiently pure for use in a subsequent step (Step L) without further purification.

Step F: Preparation of (S)-2-(tert-butoxycarbonylamino)-N-methoxy-N-methyl-4-(methylthio)butanamide L-N-Boc-methionine (30.0 g, 0.120 mmol), N,O-dimethylhydroxylamine hydrochloride (14.1 g, 0.144 mol), EDC hydrochloride (27.7 g, 0.144 mol) and HOBT (19.5 g, 0.144 mol) were stirred in dry DMF (300 mL) at 20° C. under nitrogen. More N,O-dimethylhydroxylamine hydrochloride (2.3 g, 23 mmol) was added to obtain pH 7–8. The reaction was stirred overnight, the DMF distilled to half the original volume under high vacuum, and the residue partitioned between ethyl acetate and sat. NaHCO₃ soln. The organic phase was washed with saturated sodium bicarbonate, water, 10% citric acid, and brine, and dried with sodium sulfate. The solvent was removed in vacuo to give the title compound.

Step G: Preparation of (S)-2-(tert-butoxycarbonylamino)-4-(methylthio)butanal

A suspension of lithium aluminum hydride (5.02 g, 0.132 mol) in ether (500 mL) was stirred at room temperature for one hour. The solution was cooled to −50° C. under nitrogen, and a solution of the product from Step F (39.8 g, ca. 0.120 mol) in ether (200 mL) was added over 30 min, maintaining the temperature below −40° C. When the addition was complete, the reaction was warmed to 5° C., then recooled to −45° C. Analysis by tlc revealed incomplete reaction. The solution was rewarmed to 5° C., stirred for 30 minutes, then cooled to −50° C. A solution of potassium hydrogen sulfate (72 g, 0.529 mol) in 200 mL water was slowly added, maintaining the temperature below −20° C. The mixture was warmed to 5° C. filtered through Celite, and concentrated in vacuo to provide the title aldehyde.

Step H: Preparation of (S)-2-(tert-butoxycarbonylamino)-N-(3-chlorophenyl)-4-(methylthio)butanamine To a solution of 3-chloroaniline (10.3 mL, 97.4 mmol), the product from Step G (23.9 g, 97.4 mmol), and acetic acid (27.8 mL, 487 mmol) in dichloroethane (250 mL) under nitrogen was added sodium triacetoxyborohydride (41.3 g, 195 mmol). The reaction was stirred overnight, then quenched with saturated sodium bicarbonate solution. The solution was diluted with $CHCl_3$, and the organic phase was washed with water, 10% citric acid and brine. The solution was dried over sodium sulfate and concentrated in vacuo to provide the crude product (34.8 g) which was chromatographed on silica gel with 20% ethyl acetate in hexane to obtain the title compound.

Step I: Preparation of (S)-4-(tert-butoxycarbonyl)-1-(3-chlorophenyl)-5-[2-(methylthio)ethyl]piperazin-2-one A solution of the product from Step H (22.0 g, 63.9 mmol) in ethyl acetate (150 mL) was vigorously stirred at 0° C. with saturated sodium bicarbonate (150 mL). Chloroacetyl chloride (5.6 mL, 70.2 mmol) was added dropwise, and the reaction stirred at 0° C. for 2 h. The layers were separated, and the ethyl acetate phase was washed with 10% citric acid and saturated brine, and dried over sodium sulfate. After concentration in vacuo, the resulting crude product (27.6 g) was dissolved in DMF (300 mL) and cooled to 0° C. under argon. Cesium carbonate (63.9 g, 196 mmol) was added, and the reaction was stirred for two days, allowing it to warm to room temperature. Another portion of cesium carbonate (10 g, 30 mmol) was added, and the reaction was stirred for 16 hours. The DMF was distilled in vacuo, and the residue partitioned between ethyl acetate and water. The organic phase was washed with saturated brine, and dried over sodium sulfate. The crude product was chromatographed on silica gel with 20–25% ethyl acetate in hexane to obtain the title compound.

Step J: Preparation of (S)-4-(tert-butoxycarbonyl)-1-(3-chlorophenyl)-5-[2-(methanesulfonyl)ethyl]piperazin-2-one A solution of the product from Step I (14.2 g, 37 mmol) in methanol (300 mL) was cooled to 0° C. and a solution of magnesium monoperoxyphthalate (54.9 g, 111 mmol) in 210 mL MeOH was added over 20 minutes. The ice bath was removed, and the solution was allowed to warm to room temperature. After 45 minutes, the reaction was concentrated in vacuo to half the original volume, then quenched by the addition of 2N $Na_2S_2O_3$ soln. The solution was poured into EtOAc and sat $NaHCO_3$ solution, and the organic layer was washed with brine, dried ($Na_2SO_4$), filtered, and concentrated in vacuo to provide the crude sulfone. This material was chromatographed on silica gel with 60–100% ethyl acetate in hexane to obtain the titled compound.

Step K: Preparation of (S)-1-(3-chlorophenyl)-5-[2-(methanesulfonyl)ethyl]piperazin-2-one Through a solution of Boc-protected piperazinone from Step J (1.39 g, 3.33 mmol) in 30 mL of EtOAc at 0° C. was bubbled anhydrous HCl gas. The saturated solution was stirred for 35 minutes, then concentrated in vacuo to provide the hydrochloride salt as a white powder. This material was suspended in EtOAc and treated with dilute aqueous $NaHCO_3$ solution. The aqueous phase was extracted with EtOAc, and the combined organic mixture was washed with brine, dried ($Na_2SO_4$), filtered, and concentrated in vacuo. The resulting amine was reconcentrated from toluene to provide the titled material suitable for use in the next step.

Step L: Preparation of (S)-1-(3-chlorophenyl)-4-[1-(4-cyanobenzyl)-5-imidazolylmethyl]-5-[2-(methanesulfonyl)-ethyl]-2-piperazinone dihydrochloride To a solution of the amine from Step K (898 mg, 2.83 mmol) and imidazole carboxaldehyde from Step E (897 mg, 4.25 mmol) in 15 mL of 1,2-dichloroethane was added sodium triacetoxyborohydride (1.21 g, 5.7 mmol). The reaction was stirred for 23 hours, then quenched at 0° C. with sat. $NaHCO_3$ solution. The solution was poured into $CHCl_3$, and the aqueous layer was back-extracted with $CHCl_3$. The combined organics were washed with brine, dried ($Na_2SO_4$), filtered, and concentrated in vacuo. The resulting product was purified by silica gel chromatography (95:5:0.5–90:10:0 EtOAc:MeOH:$NH_4Cl$), and the resultant product was taken up in EtOAc/methanol and treated with 2.1 equivalents of 1M HCl/ether solution. After concentrated in vacuo, the product dihydrochloride was isolated as a white powder.

Example 43

Preparation of (S)-1-(3-chlorophenyl)-4-[1-(4-cyanobenzyl)-5-imidazolylmethyl]-5-[2-(ethanesulfonyl)ethyl]-2-piperazinone dihydrochloride Step A: Preparation of (S)-N-(tert-butoxycarbonyl) homoserine lactone To a solution of (S)-homoserine lactone hydrochloride (11.0 g, 79.9 mmol) and di-tert-butylpyrocarbonate (19.2 g, 88.0 mmol) in 160 mL of dichloromethane at 0° C. was added diisopropylethylamine (13.9 mL, 79.9 mmol) over 3 min. The solution was allowed to warm to room temperature. After 3 hours, another portion of di-tert-butylpyrocarbonate (1.75 g, 8.0 mmol) and diisopropylethylamine (0.70 mL, 4.0 mmol) were added, and the mixture was stirred for an additional 2.5 hours. The solution was washed with 10% citric acid, sat. $NaHCO_3$, and brine, dried ($Na_2SO_4$), filtered, and concentrated in vacuo. The resulting material was purified by silica gel chromatography (50% EtOAc/hexane) to provide pure titled compound.

Step B: Preparation of (S)-N-(tert-butoxycarbonyl) homoserine lactol

To a solution of the lactone from Step A (7.0 g, 35 mmol) in 175 mL of THF at −78° C. was added diisobutylaluminum hydride (72.0 mL, 1M in THF, 72 mmol) dropwise, while maintaining the reaction temperature below −72° C. After 3 hours, another portion of diisobutylaluminum hydride (10.0 mL, 10 mmol) was added, followed by another after 1 hour (20.0 mL, 20 mmol). After an additional hour, the reaction was quenched with EtOAc at −78° C., followed by sat. Na-K-tartrate soln., then warmed to room temperature. The solution was poured into EtOAc, washed with brine, dried ($Na_2SO_4$), filtered, and concentrated in vacuo. The resulting material was purified by silica gel chromatography (50% EtOAc/hexane) to give the titled lactol.

Step C: Preparation of (S)-3-(tert-butoxycarbonylamino)-N-(3-chlorophenyl)-4-hydroxy-1-butanamine To a solution of lactol from Step B (4.49 g, 22.2 mmol) and 3-chloroaniline (2.58 mL. 24.4 mmol) in 50 mL of dichloromethane at room temperature was added acetic acid (1.27 mL. 22.2 mmol). After 10 min, sodium triacetoxyborohydride (6.59 g, 31.1 mmol) was added, and the solution was stirred for 1.5 hours. The reaction was quenched with sat. aq. NaHCO$_3$, diluted with CH$_2$Cl$_2$, and the layers were separated. The organic material was dried (Na$_2$SO$_4$), filtered, and concentrated in vacuo to provide a solid which was purified by silica gel chromatography (EtOAc/hexane) to give the titled amine.

Step D: Preparation of (S)-N-[2-(tert-butoxycarbonylamino)-4-hydroxybutyl]-2-chloro-N-(3-chlorophenyl)acetamide The aniline derivative from Step C (5.29 g, 16.9 mmol) was dissolved in 60 mL of EtOAc and 60 mL of sat. NaHCO$_3$ soln., then cooled to 0° C. With vigorous stirring, chloroacetyl chloride (1.48 mL. 18.5 mmol) was added dropwise. After 2 hours, the reaction was diluted with water and EtOAc, and the organic layer was washed with brine, dried (Na$_2$SO$_4$), filtered, and concentrated in vacuo to provide the titled chloroacetamide, which was used without further purification.

Step E: Preparation of (S)-4-(tert-butoxycarbonyl)-1-(3-chlorophenyl)-5-(2-hydroxyethyl)piperazin-2-one To a solution of the chloroacetamide from Step D (6.32 g, 16.1 mmol) in 80 mL of DMF at 0° C. was added cesium carbonate (15.8 g, 48.3 mmol). The solution was stirred until tlc analysis indicated consumption of the starting material (ca. 5 hours). The solution was poured into EtOAc, washed with water and brine, dried (Na$_2$SO$_4$), filtered, and concentrated in vacuo to provide the crude product. This material was purified by silica gel chromatography (99:1:0–95:5:0.15 CHCl$_3$:MeOH:NH$_4$OH) to yield the product containing a minor amount of DMF impurity.

Step F: Preparation of (S)-4-(tert-butoxycarbonyl)-1-(3-chlorophenyl)-5-[2-(methanesulfonyloxy)ethyl]piperazin-2-one To a solution of the alcohol from Step E (3.58 g, 10.1 mmol) in 50 mL of dichloromethane at 0° C. was added diisopropylethylamine (3.5 mL, 20.2 mmol), followed by methanesulfonyl chloride (0.936 mL, 12.1 mmol). The solution was stirred for 45 minutes, then quenched with 10% citlic acid. The solution was washed with brine, dried (Na$_2$SO$_4$), filtered, and concentrated in vacuo to provide the crude product which was used in the next step without further purification.

Step G: Preparation of (S)-4-(tert-butoxycarbonyl)-1-(3-chlorophenyl)-5-[2-(ethylthio)ethyl]piperazin-2-one To a solution of the mesylate from Step F (3.6 g, 8.3 mmol) in 100 mL of DMF at 0° C. was added sodium ethanethiolate (1.4 g, 16.6 mmol). After 2 hours, the reaction was poured into EtOAc, washed with sat. NaHCO$_3$ and brine, dried (Na$_2$SO$_4$), filtered, and concentrated in vacuo to provide the crude product which was used in the next step without further purification.

Step H: Preparation of (S)-4-(tert-butoxycarbonyl)-1-(3-chlorophenyl)-5-[2-(ethanesulfonyl)ethyl]piperazin-2-one To solution of the product from Step G (3.12 g, 7.82 mmol) in methanol (50 mL) was added a solution of magnesium monoperoxyphthalate (11.6 g, 23.5 mmol) in 50 mL MeOH at room temperature. After 45 minutes, the reaction was quenched by the addition of 2N Na$_2$S$_2$O$_3$ soln. The solution was poured into EtOAc and sat NaHCO$_3$ solution, and the organic layer was washed with brine, dried (Na$_2$SO$_4$), filtered, and concentrated in vacuo to provide the crude sulfone. This material was chromatographed on silica gel with 2% methanol in chloroform to obtain the titled compound.

Step I: Preparation of (S)-1-(3-chlorophenyl)-5-[2-(ethanesulfonyl)ethyl]piperazin-2-one Through a solution of the Boc-protected piperazinone from Step H (1.75 g, 4.06 mmol) in 20 mL of EtOAc at 0° C. was bubbled anhydrous HCl gas. The saturated solution was stirred for 30 minutes, then concentrated in vacuo to provide the hydrochloride of title compound as a white powder. This material was suspended in EtOAc and treated with dilute aqueous NaHCO$_3$ solution. The aqueous phase was extracted with EtOAc, and the combined organic mixture was washed with brine, dried (Na$_2$SO$_4$), filtered, and concentrated in vacuo. The resulting titled amine was reconcentrated from toluene to provide the title compound suitable for use in the next step.

Step J: Preparation of (S)-1-(3-chlorophenyl)-4-[1-(4-cyanobenzyl)-5-imidazolylmethyl]-5-[2-(ethanesulfonyl)ethyl]-2-p2iperazinone dihydrochloride To a solution of the amine from Step I (480 mg, 1.45 mmol), imidazole carboxaldehyde from Step E of Example 42 (460 mg, 2.2 mmol), and acetic acid (0.415 mL, 7.25 mmol) in 10 mL of 1,2-dichloroethane was added sodium triacetoxyborohydride (615 mg, 2.9 mmol). The reaction was stirred for 18 hours, then quenched at 0° C. with sat. NaHCO$_3$ solution. The solution was poured into CH$_2$Cl$_2$, and the organic layer was washed with brine, dried (Na$_2$SO$_4$), filtered, and concentrated in vacuo. The resulting product was purified by silica gel chromatography (2–5% MeOH:CHCl$_3$), to give the desired product and less polar boron complex. The latter compound was taken up in dichloromethane (1 mL) and benzene (5 mL), treated with n-propylamine (1 mL) for 18 hours, and concentrated in vacuo. The residue was purified by silica gel chromatography (2–5% MeOH:CHCl$_3$), combined with the former batch, taken up in EtOAc/methanol, and treated with 2.1 equivalents of 1M HCl/ether solution. After concentrated in vacuo), the product dihydrochloride was isolated as a white powder.

Example 44

Preparation of (R)-1-(3-chlorophenyl)-4-[1-(4-cyanobenzyl)-5-imidazolylmethyl]-5-[2-(ethanesulfonyl)methyl]-2-piperazinone dihydrochloride Step A: Preparation of (R)-2-(tert-butoxycarbonylamino)-N-(3-chlorophenyl)-3-[(triphenylmethyl)thio]-1-propanamine To a solution of 3-chloroaniline (0.709 mL. 6.70 mmol) in 30 mL of dichloromethane at room temperature was added 1.2 g of crushed 4 Å molecular sieves. Sodium triacetoxyborohydride (3.55 g, 16.7 mmol) was added, followed by diopwise addition of N-methylmorpholine to achieve a pH of 6.5. L-S-Trityl-N-Boc-cysteinal (3.15 g, 7.04 mmol) (prepared according to S. L. Graham et al. *J. Med. Chem.*, (1994) Vol. 37, 725–732) was added, and the solution was stirred for 48 hours. The reaction was quenched with sat. aq. NaHCO$_3$, diluted with EtOAc, and the layers were separated. The organic material was washed with brine, dried (Na$_2$SO$_4$), filtered, and concentrated in vacuo to provide an oil which was purified by silica gel chromatography (15% EtOAc/hexane) to give the title amine.

Step B: Preparation of (R)-N-[2-(tert-butoxycarbonylamino)-3-((triphenylmethyl)thio)propyl]-2-chloro-N-(3-chlorophenyl)acetamide The aniline derivative from Step A (2.77 g, 4.95 mmol) was dissolved in 73 mL of EtOAc and 73 mL of sat. NaHCO$_3$ soln., then cooled to 0° C. With vigorous stirring, chloroacetyl chloride (0.533 mL. 6.69 mmol) was added dropwise. After 3 hours, the reaction was diluted with water and EtOAc, and the organic layer was washed with brine, dried (Na$_2$SO$_4$), filtered, and concentrated in vacuo to provide crude titled chloroacetamide which was used without further purification.

Step C: Preparation of (R)-4-(tert-butoxycarbonyl)-1-(3-chlorophenyl)-5-[S-(triphenylmethyl)thiomethyl]piperazin-2-one To a solution of chloroacetamide from Step B (3.29 g crude, theoretically 4.95 mmol) in 53 mL of DMF at 0° C. was added cesium carbonate (4.84 g, 14.95 mmol). The solution was stirred for 48 hours, allowing it to warm to room temperature. The solution was poured into EtOAc, washed with water and brine, dried ($Na_2SO_4$), filtered, and concentrated in vacuo to provide the crude product as an oil. This material was purified by silica gel chromatography (20% EtOAc/hexane) to yield the product as a white solid.

Step D: Preparation of (R)-4-(tert-butoxycarbonyl)-1-(3-chlorophenyl)-5-(thiomethyl)piperazin-2-one A solution of piperazinone from Step C (625 mg, 1.04 mmol) in degassed EtOAc (38 mL) and EtOH (12 mL) was warmed to 30° C. A solution of $AgNO_3$ (177 mg, 1.04 mmol) and pyridine (0.084 mL, 1.04 mmol) in 8 mL of EtOH was added, and the solution was heated to reflux. After 45 minutes, the reaction was concentrated in vacuo, then redissolved in 26 mL of degassed EtOAc. Through this solution was bubbled $H_2S$ gas for 2.5 minutes, then activated charcoal was added after 4 minutes. The material was filtered through celite and rinsed with degassed EtOAc, concentrated in vacuo, then reconcentrated from degassed $CH_2Cl_2$ to provide the crude product which was used without further purification.

Step E: Preparation of (R)-4-(tert-butoxycarbonyl)-1-(3-chlorophenyl)-5-[(ethylthio)methyl]piperazin-2-one A solution of the thiol from Step D (ca. 1.04 mmol) in 3 mL of THF was added via cannula to a suspension of NaH (51.4 mg, 60% disp. in mineral oil, 1.28 mmol) in 2 mL THF at 0° C. After 10 minutes, iodoethane was added (0.079 mL, 0.988 mmol), and the solution was stirred for 1.5 hours. The reaction was poured into EtOAc, washed with sat. $NaHCO_3$ and brine, dried ($Na_2SO_4$), filtered, and concentrated in vacuo to provide the crude product. This material was purified by silica gel chromatography (1% $MeOH/CH_2Cl_2$) to yield the titled product.

Step F: Preparation of (R)-4-(tert-butoxycarbonyl)-1-(3-chlorophenyl)-5-[(ethanesulfonyl)methyl]piperazin-2-one To a solution of the sulfide from Step E (217 mg, 0.563 mmol) in 3 mL of MeOH at 0° C. was added a solution of magnesium monoperoxyphthalate (835 mg, 1.69 mmol) in 2 mL MeOH. The reaction was stirred overnight, allowing it to warm to room temperature. The solution was cooled to 0° C., quenched by the addition of 4 mL 2N $Na_2S_2O_3$ soln., then concentrated in vacuo. The residue was partitioned between EtOAc and sat $NaHCO_3$ solution, and the organic layer was washed with brine, dried ($Na_2SO_4$), filtered, and concentrated in vacuo to provide the crude sulfone as a white waxy solid.

Step G: Preparation of (R)-1-(3-chlorophenyl)-4-[1-(4-cyanobenzyl)-5-imidazolylmethyl]-5-[2-(ethanesulfonyl)methyl]-2-piperazinone dihydrochloride To a solution of the Boc-protected piperazinone from Step F (224 mg, 0.538 mmol) in 5 mL of dichloromethane at 0° C. was added 2.5 mL of trifluoroacetic acid (TFA). After 45 minutes, the reaction was concentrated in vacuo, then azeotroped with benzene to remove the excess TFA. The residue was taken up in 4 mL of 1,2-dichloroethane and cooled to 0° C. To this solution was added 4 Å powdered molecular sieves (340 mg), followed by sodium triacetoxyborohydride (285 mg, 1.34 mmol) and several drops of triethylamine to achieve pH=6. The imidazole carboxaldehyde from Step E of Example 42 (125 mg, 0.592 mmol) was added, and the reaction was stirred at 0° C. After 2 days, the reaction was poured into EtOAc, washed with dilute aq. $NaHCO_3$, and brine, dried ($Na_2SO_4$), filtered, and concentrated in vucuo. The crude product was taken up in methanol and injected onto a preparative HPLC column and purified with a mixed gradient of 15%–50% acetonitrile/0.1% TFA; 85%–50% 0.1% aqueous TFA over 60 minutes. After concentration in vacuo, the resultant product was partitioned between dichloromethane and aq. $NaHCO_3$ soln., and the aqueous phase was extracted with $CH_2Cl_2$. The organic solution was washed with brine, dried ($Na_2SO_4$), filtered, and concentrated to dryness to provide the product free base, which was taken up in $CH_2Cl_2$ and treated with 2.1 equivalents of 1M HCl/ether solution. After concentrated in vacuo, the product dihydrochloride was isolated as a white powder.

Example 45

Preparation of (S)-1-(3-chlorophenyl)-4-[1-(4-cyanobenzyl)-5-imidazolylmethyl]-5-[N-ethyl-2-acetamido]-2-piperazinone dihydrochloride Step A: Preparation of (S)-4-(tert-butoxycarbonyl)-1-(3-chlorophenyl)-5-[2-(oxo)ethyl]piperazin-2-one To a solution of oxalyl chloride (0.608 mL, 6.97 mmol) in dichloromethane (40 mL) at −78° C. was added DMSO (0.990 mL, 13.9 mmol) over 2–3 minutes. The solution was stirred for 10 minutes, then a solution of the alcohol from Step E of Example 43 (2.06 g, 5.81 mmol) in 10 mL of dichloromethane was added over 5 minutes, keeping the reaction temperature below −70° C. The reaction was stirred for 10 minutes, then triethylamine (2.43 mL) was added, and the reaction was stirred at −78° C. for 5 minutes, then allowed to warm to room temperature. After 45 minutes, the solution was poured into dichloromethane, and washed with sat. $NH_4Cl$ soln., 10% citric acid soln., water, and brine. The solution was dried ($Na_2SO_4$), filtered, and concentrated in vacuo to provide the titled aldehyde.

Step B: Preparation of (S)-4-(tert-butoxycarbonyl)-5-(carboxymethyl)-1-(3-chlorophenyl)piperazin-2-one To a solution of the aldehyde from Step A (1.52 g, 4.31 mmol) in 2-methyl-2-propanol (50 mL) and 2-methyl-2-butene (10 mL) at room temperature was added a solution of sodium chlorite (585 mg, 5.17 mmol) and sodium dihydrogenphosphate (595 mg, 4.31 mmol) in 10 mL of water. The reaction turned yellow, then slowly faded to light pink over 45 minutes. The solution was poured into EtOAc, and washed with sat. sodium bisulfite soln. The aqueous layer was acidified to pH 3 with 2.75M $KHSO_4$ soln., and extracted several times with EtOAc. The combined organic extracts were dried ($Na_2SO_4$), filtered, and concentrated in vacuo to provide the titled carboxylic acid.

Step C: Preparation of (S)-4-(tert-butoxycarbonyl)-5-[N-ethyl-2-acetamido]-1-(3-chlorophenyl)piperazin-2-one The product from Step B (200 mg, 0.56 mmol), ethylamine hydrochloride (114 mg, 1.4 mmol), EDC hydrochloride (140 mg, 0.73 mmol) and HOBT hydrate (113 mg, 0.84 mmol) were stirred in dry DMF (3 mL) at 0° C. under nitrogen. After one hour, the solution was warmed to room temperature, and stirred overnight. The DMF was removed in vacuo, and the residue was partitioned between ethyl acetate and water. The organic phase was washed with 10% citric acid, saturated sodium bicarbonate, water, and brine, and dried with sodium sulfate. The solvent was removed in vacuo to give the title compound.

Step D: Preparation of (S)-1-(3-chlorophenyl)-4-[1-(4-cyanobenzyl)-5-imidazolylmethyl]-5-[N-ethyl-2-acetamido]-2-piperazinone dihydrochloride The titled product was prepared from the product of Step C (184 mg, 0.47 mmol) in analogy to Example 42, Steps K and L. The product was isolated as a white solid.

Example 46

Preparation of (±)-5-(2-butynyl)-1-(3-chlorophenyl)-4-[1-(4-cyanobenzyl)-5-imidazolylmethyl]-2-piperazinone dihydrochloride Step A: Preparation of 1-(methanesulfonyl)-2-butyne To a solution of 2-butynol (10.0 mL, 134 mmol) in 200 mL of dichloromethane at 0° C. was added methanesulfonyl chloride (23.4 g, 134 mmol), followed by dropwise addition of diisopropylethylamine (30 mL, 174 mmol). After 1.5 hours, the solution was poured into 0.5N KHSO$_4$ soln, and the organic layer was washed with brine. The solution was dried over Na$_2$SO$_4$, filtered, and concentrated in vacuo to provide the titled product.

Step B: Preparation of (±)-ethyl 2-[(phenylmethyl)imino]-4-hexynoate

To a solution of glycine ethyl ester hydrochloride (10.11 g, 72.4 mmol) in 200 mL of dichloromethane was added benzaldehyde (7.36 mL, 72.4 mmol), triethylamine (20.0 mL, 143 mmol), and magnesium sulfate (6 g). The solution was stirred at room temperature for 16 hours, filtered through a glass frit, and concentrated in vacuo. The residue was partitioned between ether and water, and the organic layer was washed with brine. The solution was dried over Na$_2$SO$_4$, filtered, and concentrated in vacuo to provide a pale yellow oil. A portion of this oil (9.90 g, 51.8 mmol) was dissolved in 200 mL of THF and cooled to −78° C. under nitrogen atmosphere. A solution of potassium tert-butoxide in THF (51.8 mL of 1M, 51.8 mmol) was added dropwise to produce a bright red solution. After 20 minutes, a solution of the mesylate from Step A (8.05 g, 54,4 mmol) in 20 mL of THF was added dropwise via cannula, and the solution was allowed to warm to room temperature. After 2 hours, the reaction was poured into EtOAc and washed with sat. NaHCO$_3$ soln. and brine, dried (Na$_2$SO$_4$), filtered, and concentrated in vacuo to provide the titled product.

Step C: Preparation of (±)-ethyl 2-[(tert-butoxycarbonyl)amino]-4-hexynoate

A solution of the product from Step B (ca. 51.8 mmol) was stirred at room temperature in 5% aqueous HCl solution (100 mL). After 12 hours, the solution was concentrated in vacuo to give an orange oil. This product was taken up in 50 mL of THF and sat. NaHCO$_3$ soln. was added (50 mL), followed by di-tert-butylpyrocarbonate (11.3 g, 51.8 mmol) at room temperature. After 6 hours, the reaction was poured into EtOAc and washed with sat. NaHCO$_3$ soln. and brine, dried (Na$_2$SO$_4$), filtered, and concentrated in vacuo to provide the titled product.

Step D: Preparation of (±)-2-[(tert-butoxycarbonyl)amino]-4-hexynoic acid

To a solution of the product from Step C (ca. 51.8 mmol) in THF (100 mL) and water (20 mL) was added at 0° C. a solution of lithium hydroxide monohydrate (6.5 g, 155 mmol). The solution was stirred for 1 hour at 0° C., then warmed to room temperature. After 48 hours, the solution was concentrated in vacuo. The aqueous mixture was extracted with EtOAc, acidified at 0° C. with 10% aq. HCl soln., then extracted with three portions of dichloromethane. The combined dichloromethane extracts were dried (Na$_2$SO$_4$), filtered, and concentrated in vacuo to provide the tilled product as an orange oil.

Step E: Preparation of (±)-2-(tert-butoxycarbonylamino)-N-methoxy-N-methyl-4-hexynamide The product from Step D (10.58 g, 46.6 mmol), N,O-dimethylhydroxylamine hydrochloride (9.09 g, 93.2 mmol), HOBT hydrate (9.44 g, 69.9 mmol) and triethylamine (13.0 mL, 93.2 mmol) were stirred in dry DMF (150 mL) at 0° C. under nitrogen. EDC hydrochloride (11.5 g, 60.6 mmol) was added, and the reaction was stirred for 3 hours. The solution was partitioned between 2:1 ethyl acetate:hexane and water, washed with water, 10% aq. HCl, sat. NaHCO$_3$ soln and brine, then dried with sodium sulfate. The solvent was removed in vacuo to give the title compound as an orange oil Step F: Preparation of (±)-2-(tert-butoxycarbonylamino)-4-hexynal A suspension of lithium aluminum hydride (1.56 g, 41.1 mmol) in ether (150 mL) was stirred at room temperature for 30 minutes. The solution was cooled to −55° C. under nitrogen, and a solution of the product from Step E (11.10 g, 41.1 mmol) in ether (150 mL) was added over 15 min, maintaining the temperature below −50° C. When the addition was complete, the reaction was warmed to 5° C., then recooled to −40° C. A solution of potassium hydrogen sulfate (21.8 g) in 25 mL water was slowly added, maintaining the temperature below −35° C. The mixture was warmed to room temperature and stirred for one hour, filtered through Celite, and concentrated in vacuo to provide the title aldehyde.

Step G: Preparation of (±)-2-(tert-butoxycarbonylamino)-N-(3-chlorophenyl)-4-butylamine To a 0° C. solution of 3-chloroaniline (4.33 mL, 40.9 mmol), the product from Step F (ca. 41 mmol), and crushed 4 Å molecular sieves (10 g) in dichloroethane (100 mL) under nitrogen was added sodium triacetoxyborohydride (12.9 g, 61.5 mmol). The reaction was stirred for one hour, then warmed to room temperature. After 3 hours, the solution was poured into EtOAc and washed with water, sat. NaHCO$_3$ soln. and brine. The solution was dried over sodium sulfate and concentrated in vacuo to provide the crude product.

Step H: Preparation of (±)-N-[2-(tert-butoxycarbonylamino)-4-hexynyl]-2-chloro-N-(3-chlorophenyl)acetamide A solution of the product from Step G (1.68 g, 5.22 mmol) and triethylamine (1.20 mL, 8.61 mmol in 15 mL of CH$_2$Cl$_2$ was cooled to 0° C. Chloroacetyl chloride (0.457 mL, 5.74 mmol) was added dropwise, and the reaction was maintained at 0° C. with stirring. after 30 minutes, another portion of chloroacetyl chloride (0.20 mL) and triethylamine (0.5 mL) was added dropwise. After 30 min, the reaction was poured into EtOAc and washed with 10% aq. HCl, sat. aq. NaHCO$_3$ soln., and brine. The solution was dried (Na$_2$SO$_4$), filtered, and concentrated in vacuo to provide a brown oil This material was purified by silica gel chromatography (20–35% EtOAc/hexane) to yield the titled product.

Step I: Preparation of (±)-4-(tert-butoxycarbonyl)-5-(2-butynyl)-1-(3-chlorophenyl)-2-piperazinone To a solution of the chloroacetamide from Step H (1.68 g, 4.23 mmol) in 15 mL of dry DMF at 0° C. was added Cs$_2$CO$_3$ (3.08 g, 9.48 mmol). The solution was stirred for 30 minutes, then allowed to warm to room temperature. After 14 hours, the reaction was poured into 50% EtOAc/hexane, washed with water and brine, dried (Na$_2$SO$_4$), filtered, and concentrated in vacuo to provide the crude product. This material was purified by silica gel chromatography (20–40% EtOAc/hexane) to yield the titled product.

Step J: Preparation of (±)-5-(2-butynyl)-1-(3-chlorophenyl)-4-[1-(4-cyanobenzyl)-5-imidazolylmethyl]-2-piperazinone dihydrochloride To a solution of the Boc-protected piperazinone from Step I (1.03 g, 2.85 mmol) in 7 mL of dichloromethane at 0° C. was added 4 mL of trifluoroacetic acid (TFA). After 4 hours, the reaction was warmed to room temperature, and stirred an additional 6 hours. The solution was concentrated in vacuo, then azeotroped with benzene to remove the excess TFA. A portion of the residue (255 mg, 0.678 mmol) was taken up in 6 mL of 1,2-dichloroethane and cooled to 0° C. To this solution was added 4 Å powdered molecular sieves (600 mg), followed by sodium triacetoxyborohydride (214 mg, 1.02 mmol). The imidazole carboxaldehyde from Step E of Example 42 (186 mg, 0.881 mmol) was added, and the reaction was stirred at 0° C. After 24 hours, the reaction was poured into EtOAc, washed with dilute aq. NaHCO$_3$, and brine, dried (Na$_2$SO$_4$), filtered, and concentrated in vacuo. This material was purified by silica gel chromatography (2–5% MeOH:CH$_2$Cl$_2$) to yield a white foam which was taken up in CH$_2$Cl$_2$ and treated with 2.1 equivalents of 1M HCl/ether solution. After concentrated in vacuo, the product dihydrochloride was isolated as a white powder.

Example 47

Preparation of 1-(3-chlorophenyl)-4-[1-(4-cyanobenzyl)imidazolylmethyl]-2-piperazinone dihydrochloride Step A: Preparation of N-(3-chlorophenyl)ethylenediamine hydrochloride To a solution of 3-chloroaniline (30.0 mL, 284 mmol) in 500 mL of dichloromethane at 0° C. was added dropwise a solution of 4N HCl in 1,4-dioxane (80 mL, 320 mmol HCl). The solution was warmed to room temperature, then concentrated to dryness in vacuo to provide a white powder. A mixture of this powder with 2-oxazolidinone (24.6 g, 282 mmol) was heated under nitrogen atmosphere at 160° C. for 10 hours, during which the solids melted, and gas evolution was observed. The reaction was allowed to cool, forming the crude diamine hydrochloride salt as a pale brown solid.

Step B: Preparation of N-(tert-butoxycarbonyl)-N'-(3-chlorophenyl)ethylenediainine The amine hydrochloride from Step A (ca. 282 mmol, crude material prepared above) was taken up in 500 mL of THF and 500 mL of sat. aq. NaHCO$_3$ soln., cooled to 0° C., and di-tert-butylpyrocarbonate (61.6 g, 282 mmol) was added. After 30 h, the reaction was poured into EtOAc, washed with water and brine, dried (Na$_2$SO$_4$), filtered, and concentrated in vacuo to provide the titled carbamate as a brown oil which was used in the next step without further purification.

Step C: Preparation of N-[2-(tert-butoxycarbamoyl)ethyl]-N-(3-chlorophenyl)-2-chloroacetamide A solution of the product from Step B (77 g, ca. 282 mmol) and triethylamine (67 mL, 480 mmol) in 500 mL of CH$_2$Cl$_2$ was cooled to 0° C. Chloroacetyl chloride (25.5 mL, 320 mmol) was added dropwise, and the reaction was maintained at 0° C. with stirring. After 3 h, another portion of chloroacetyl chloride (3.0 mL) was added dropwise. After 30 min, the reaction was poured into EtOAc (2 L) and washed with water, sat. aq. NH$_4$Cl soln, sat. aq. NaHCO$_3$ soln., and brine. The solution was dried (Na$_2$SO$_4$), filtered, and concentrated in vacuo to provide the chloroacetamide as a brown oil which was used in the next step without further purification.

Step D: Preparation of 4-(tert-butoxycarbonyl)-1-(3-chlorophenyl)-2-piperazinone To a solution of the chloroacetamide from Step C (ca. 282 mmol) in 700 mL of dry DMF was added K$_2$CO$_3$ (88 g, 0.64 mol). The solution was heated in an oil bath at 70°–75° C. for 20 hours, cooled to room temperature, and concentrated in vacuo to remove ca. 500 mL of DMF. The remaining material was poured into 33% EtOAc/hexane, washed with water and brine, dried (Na$_2$SO$_4$), filtered, and concentrated in vacuo to provide the product as a brown oil. This material was purified by silica gel chromatography (25–50% EtOAc/hexane) to yield pure product, along with a sample of product (ca. 65% pure by HPLC) containing a less polar impurity.

Step E: Preparation of 1-(3-chlorophenyl)-2-piperazinone

Through a solution of Boc-protected piperazinone from Step D (17.19 g, 55.4 mmol) in 500 mL of EtOAc at −78° C. was bubbled anhydrous HCl gas. The saturated solution was warmed to 0° C., and stirred for 12 hours. Nitrogen gas was bubbled through the reaction to remove excess HCl, and the mixture was warmed to room temperature. The solution was concentrated in vacuo to provide the hydrochloride as a white powder. This material was taken up in 300 mL of CH$_2$Cl$_2$ and treated with dilute aqueous NaHCO$_3$ solution. The aqueous phase was extracted with CH$_2$Cl$_2$ (8×300 mL) until the analysis indicated complete extraction. The combined organic mixture was dried (Na$_2$SO$_4$), filtered, and concentrated in vacuo to provide the titled free amine as a pale brown oil.

Step F: Preparation of 1-(3-chlorophenyl)-4-[1-(4-cyanobenzyl)-5-imidazolylmethyl]-2-piperazinone dihydrochloride To a solution of the amine from Step E (55.4 mmol, prepared above) in 200 mL of 1,2-dichloroethane at 0° C. was added 4 Å powdered molecular sieves (10 g), followed by sodium triacetoxyborohydride (17.7 g, 83.3 mmol). The imidazole carboxaldehyde from Step E of Example 42 (11.9 g, 56.4 mmol) was added, and the reaction was stirred at 0° C. After 26 hours, the reaction was poured into EtOAc, washed with dilute aq. NaHCO$_3$, and the aqueous layer was back-extracted with EtOAc. The combined organics were washed with brine, dried (Na$_2$SO$_4$), filtered, and concentrated in vacuo. The resulting product was taken up in 500 mL of 5:1 benzene:CH$_2$Cl$_2$, and propylamine (20 mL) was added. The mixture was stirred for 12 hours, then concentrated in vacuo to afford a pale yellow foam. This material was purified by silica gel chromatography (2–7% MeOH/CH$_2$Cl$_2$), and the resultant white foam was taken up in CH$_2$Cl$_2$ and treated with 2.1 equivalents of 1M HCl/ether solution. After concentrated in vacuo, the product dihydrochloride was isolated as a white powder.

Example 48

5(S)-Butyl-4-[1-(4-cyanobenzyl)-2-methyl-5-imidazolylmethyl]-1-(2,3-dimethylphenyl)-piperazin-2-one dihydrochloride Step A: 4-Bromo-2-methylimidazole-5-carboxaldehyde 4-Bromo-5-hydroxymethyl-2-methylimidazole was prepared according to the procedure described by S. P. Watson, Synthetic Communications, 22, 2971–2977 (1992). A solution of 4-bromo-5-hydroxymethyl-2-methylimidazole (4.18 g, 21.9 mmol) was refluxed with manganese dioxide (16.1 g) in 1:1 methylene chloride:dioxane (200 mL) for 16 h. The cooled reaction was filtered through celite and concentrated to yield the title compound as a pale yellow solid. $^1$H NMR (CDCl$_3$, 300 MHz) δ 9.57 (1H, s), 2.52 (3H, s).

Step B: 4-Bromo-1-(4-cyanobenzyl)-2-methylimidazole-5-carboxaldehyde

4-Cyanobenzylbromide (1.05 g, 5.39 mmol) was added to a solution of 4-bromo-2-methylimidazole-5-carboxaldehyde (1.02 g, 5.39 mmol) in dimethylacetamide (15 mL). The solution was cooled to −10° C. and powdered potassium carbonate (0.745 g, 5.39 mmol) added. The reaction was stirred at −10° C. for 2 h, and a further 4 h at 20° C. The reaction was diluted with water and extracted with ethyl acetate. The organic phase was washed with water, saturated brine, and dried over magnesium sulfate. Solvent evaporation yielded a white solid. $^1$H NMR (CDCl$_3$, 400 MHz) δ 9.68 (1H, s), 7.64 (2H, d, J=7 Hz), 7.15 (2H, d, J=7 Hz) 5.59 (2H, s), 2.40 (3H, s).

Step C: 1-(4-Cyanobenzyl)-2-methylimidazole-5-carboxaldehyde

A solution of 4-bromo-1-(4-cyanobenzyl)-2-methylimidazole-5-carboxaldehyde (1.33 g, 4.37 mmol) and imidazole (0.600 g, 8.74 mmol) in 1:1 ethyl acetate-alcohol (150 mL) was stirred with 10% palladium on carbon (0.020 g) under 1 atm hydrogen. After 2 h, the reaction was filtered through celite and concentrated to give the title compound as a white solid. $^1$H NMR (DMSO-$d_6$, 400 MHz) δ 9.62 (1H, s), 7.90 (1H, s), 7.81 (2H, d, J=8 Hz), 7.20 (2H, d, J=8 Hz), 5.64 (2H, s), 2.33 (3H, s).

Step D: 5(S)-Butyl-4-[1-(4-cyanobenzyl)-2-methyl-5-imidazolylmethyl]-1-(2,3-dimethylphenyl)piperazin-2-one dihydrochloride Sodium triacetoxyborohydride (0.265 g, 1.25 mmol) was added to a solution of 1-(4-cyanobenzyl)-2-methylimidazole-5-carboxaldehyde (0.190 g, 0.843 mmol), 5(S)-butyl-1-(2,3-dimethylphenyl)piperazin-2-one hydrochloride (0.250 g, 0.843 mmol), N-methylmorpholine (0.093 mL, 0.843 mmol) in dichloroethane (10 mL), according to the procedure described in Example 39, Step E. The title compound was purified by preparative HPLC using a gradient of 70 to 45% Solvent A. The free base was isolated and converted to dihydrochloride salt. The title compound was obtained as a white solid. FAB ms: 470 (M+1). Anal. Calc for $C_{29}H_{35}N_5O.2$ HCl.1.45 $H_2O$, C, 61.25; H, 7.07; N, 12.32. Found: C, 61.56; H, 6.99; N, 11.32.

Example 49

4-[1-(2-(4-Cyanophenyl)-2-propyl)-5-imidazolylmethyl]-1-(3-chlorophenyl)-5(S)-(2-methylsulfonylethyl)piperazin-2-one dihydrochloride Step A: 4-(tert-Butyldimethylsilyloxymethyl)-1-triphenylmethylimidazole tert-Butyldimethylsilylchloride (2.83 g, 18.76 mmol) was added to a suspension of 4-hydroxymethyl-1-triphenylmethylimidazole (5.80 g, 17.05 mmol) in DMF (200 mL) containing imidazole (3.48 g, 51.1 mmol). After 15 min, a clear colorless solution was obtained which was stirred at room temperature. When reaction was complete, the DMF was removed in vacuo and the residue patitioned between ethyl acetate and water. The organic phase was washed with water, saturated brine, and dried over magnesium sulfate. The title compound was obtained as a clear gum.

Step B: 5-tert-Butyldimethylsilyloxymethyl-1-(4-cyanobenzyl)imidazole

A solution of 4-(tert-butyldimethylsilyloxymethyl)-1-triphenylmethylimidazole (4.66 g, 10.26 mmol) and 1-bromomethyl-4-cyanobenzene (2.01 g, 10.26 mmol) in acetonitrile (50 mL) was refluxed 4 h. The reaction was cooled, acetonitrile removed in vacuo, and the residue dissolved in methanol (30 mL). This solution was refluxed for 2 h, cooled and methanol evaporated. The residue was partitioned between ethyl acetate and saturated sodium bicarbonate. The crude product was chromatographed on silica with 3% methanol in chloroform. The title compound was obtained as a white solid.

Step C: 5-tert-Butoxydimethylsilyloxymethyl-1-[2-(4-cyanophenyl)-2-propyl)]imidazole A solution of 5-tert-butyl(timethylsilyloxymethyl-1-(4-cyanobenzyl)imidazole (1.005 g, 3.07 mmol) in THF (25 mL) under nitrogen was cooled to −78° C. A solution of lithium hexamethyldisilazide (4.61 mL, 1M in THF) was added and the reaction stirred at −78° C. for 1 h, then warmed to −60° C. over 30 min. The reaction was cooled to −78° C., methyl iodide added (0.287 mL, 4.61 mmol), and stirring continued at −78° C. for an additional 2 h, before warming to 0° C. over 2 h. After 30 min, the reaction was cooled to −78° C., and lithium hexamethyldisilazide (4.61 mL, 1M in THF) added. After 1 h, methyl iodide was added (0.287 mL, 4.61 mmol) and the reaction allowed to warm to room temperature overnight. The reaction was quenched with water, extracted with ethyl acetate, and the organic phase washed with saturated brine. The crude product was chromatographed on silica gel with 6:4 ethyl acetate: methylene chloride. The title compound was obtained as a golden oil. $^1$H NMR (CDCl$_3$, 400 MHz) δ 7.78 (1H, s), 7.61 (2H, d, J=8 Hz), 7.15 (2H, d, J=8 Hz), 7.02, (1H, s), 4.00 (2H, s), 1.99 (6H, s), 0.79 (9H, s), −0.74 (6H, s).

Step D: 1-[2-(4-Cyanophenyl)-2-propyl)]-5-hydroxymethyl-imidazole

Tetra-N-butylammonium fluoride (2.99 mL, 1M in THF) was added to a solution of 5-tert-butoxydimethylsilyloxymethyl-1-[2-(4-cyanophenyl)-2-propyl)]imidazole (0.750 g, 2.72 mmol) in THF (10 mL). After 2 h at room temperature, the reaction was poured into ethyl acetate and extracted with saturated sodium bicarbonate solution. The organic phase was extracted with saturated brine, and dried over magnesium sulfate. The crude product was chromatographed on silica gel with 3% methanol in ethyl acetate. The title compound was obtained as a semi-solid. $^1$H NMR (CDCl$_3$, 400 MHz) δ 7.77 (1H, s), 7.62 (2H, d, J=8 Hz), 7.19 (2H, d, J=8 Hz), 7.02, (1H, s), 4.01 (2H, s), 2.57 (1H, br s), 2.01 (6H, s).

Step E: 1-[2-(4-Cyanophenyl)-2-propyl)]imidazole-5-carboxaldehyde

A solution of 1-[2-(4-cyaniophenyl)-2-propyl)]-5-hydroxymethylimidazole (0.450 g, 1.87 mmol) was refluxed in dioxane (20 mL) with manganese dioxide (1.62 g, 18.7 mmol) for 5 h. The reaction was cooled, filtered through celite and concentrated. The crude product was purified by chromatography on silica gel; the title compound was isolated as a semi-solid. $^1$H NMR (CDCl$_3$, 400 MHz) δ 9.37 (1H, s), 8.11 (1H, s), 7.92 (1H, s), 7.58 (2H, d, J=8 Hz), 7.15 (2H, d, J=8 Hz), 2.01 (6H, s).

Step F: 4-[1-(2-(4-Cyanophenyl)-2-propyl)-5-imidazolylmethyl]-1-(3-chlorophenyl)-5(S)-(2-methylsulfonylethyl)piperazin-2-one dihydrochloride The title compound was prepared according to the procedure described in Example 39, Step E, except using 1-(3-chlorophenyl)-5(S)-(2-methylsulfonylethyl)piperazin-2-one hydrochloride (0.297 g, 0.84 mmol), 1-[2-(4-cyanophenyl)-2-propyl)]imidazole-5-carboxaldehyde (0.200 g, 0.84 mmol), N-methylmorpholine (0.092 mL, 0.84 mmol) and sodium triacetoxyborohydride (0.267 g, 1.26 mmol). The crude product was purified by preparative HPLC with an 80 to 58% Solvent A gradient. The pure fractions were combined and converted to the hydrochloride salt, yielding the title compound. FAB ms: 540 (M+1). Anal. Calc for $C_{27}H_{30}ClN_5O_3S.2$ HCl.3 $H_2O$, C, 48.62; H, 5.74; N, 10.50. Found: C, 48.62; H, 5.73; N, 9.89.

Example 50

5(S)-n-Butyl-4-[1-(4-cyanobenzyl)-5-imidazolylmethyl]-1-(2-methylphenyl)piperazin-2-one dihydrochloride Step A: N-(2-Methylphenyl)-2(S)-(tert-butoxycarbonylamino)-hexanamine The title compound was prepared according to the procedure described in Example 39, Step C, except using o-toluidine (0.32 mL, 3.00 mmol), 2(S)-(tert-butoxycarbonylamino)hexanal (0.538, 2.50 mmol), sodium triacetoxyborohydride (0.795 g, 3.75 mmol) in dichloroethane (10 mL) The crude product was purified by column chromatography to yield the title compound.

Step B: 4-tert-Butoxycarbonyl-5(S)-n-butyl-1-(2-methylphenyl)piperazin-2-one

The title compound was prepared essentially according to the procedure described in Example 39, Step D, except using N-(2-methylphenyl)-2(S)-(tert-butoxycarbonylamino) hexanamine (0.506 g, 1.65 mmol), chloroacetyl chloride (0.158 mL, 1.98 mmol) in ethyl acetate-saturated sodium bicarbonate at 0° C. The crude product thus obtained was dissolved in DMF (15 mL), cooled to 0° C. under nitrogen, and treated with cesium carbonate (1.61 g, 4.95 mmol). The reaction was stirred at 0° C. for 2 h, and at room temperature for 2 h. The reaction was quenched with saturated ammonium chloride, and extracted with ethyl acetate. The extracts were dried and evaporated to give the title compound.

Step C: 5(S)-n-Butyl-4-[1-(4-cyanobenzyl)-5-imidazolylmethyl]-1-(2-methylphenyl)piperazin-2-one dihydrochloride The product from Step B (0.534 g, 1.50 mmol) was deprotected with trifluoroacetic acid (4 mL) in methylene chloride (10 mL). The title compound was prepared according to the procedure described in Example 39, Step E, except using 5(S)-n-butyl-1-(2-methylphenyl)piperazin-2-one ditrifluoroacetic acid salt, 1-(4-cyanobenzylimidazole)-5-carboxaldehyde (0.317 g, 1.50 mmol), and sodium triacetoxyborohydride (0.477 g, 2.25 mmol) in dichloroethane (15 mL). The crude product was injected onto a preparative HPLC column and purified with a mixed gradient of acetonitrile/0.1% TFA and 0.1% aqueous TFA. The pure fractions were combined and converted to the HCl salt. The title compound was obtained as a white solid. FAB ms (m+1) 442. Anal. Calc. for $C_{27}H_{31}N_5O.2.5$ HCl.2.05 $H_2O$: C, 56.95; H, 6.66; N, 12.30. Found: C, 56.93; H, 5.75; N, 11.55.

Example 51

4-[1-(4-Cyanobenzyl)-5-imidazolylmethyl]-5(S)-(2-fluoroethyl)-1-(3-chlorophenyl)piperazin-2-one dihydrochloride Step A: 4-tert-Butoxycarbonyl-1-(3-chlorophenyl)-5(S)-(2-fluoroethyl)-piperazin-2-one 4-tert-Butoxycarbonyl-1-(3-chlorophenyl)-5(S)-(2-methylsulfonyloxyethyl)-piperazin-2-one (0.433 g, 1.00 mmol) and tert-butylammonium fluoride (3.0 mL, 1M in THF) were stirred at room temperature in acetonitrile (5 mL) for 72 h. The reaction was quenched with saturated sodium bicarbonate and extracted with ethyl acetate. The organic extracts were dried, concentrated and purified by column chromatography using 20% ethyl acetate in hexane. The title compound was obtained as a thick oil.

Step B: 4-[1-(4-Cyanobenzyl)-5-imidazolylmethyl]-5(S)-(2-fluoroethyl)-1-(3-chlorophenyl)piperazin-2-one dihydrochloride 4-tert-Butoxycarbonyl-1-(3-chlorophenyl)-5(S)-(2-fluoroethyl)-piperazin-2-one (0.191 g, 0.54 mmol) was deprotected with trifluoroacetic acid (4 mL) in methylene chloride (10 mL). The title compound was prepared according to the procedure described in Example 39, Step E, except using 1-(3-chlorophenyl)-5(S)-(2-fluoroethyl)piperazin-2-one ditrifluoroacetic acid salt, 1-(4-cyanobenzylimidazole)-5-carboxaldehyde (0.114 g, 0.54 mmol), and sodium triacetoxyborohydride (0.172 g, 2.25 mmol) in dichloroethane (5 mL). The crude product was injected onto a preparative HPLC column and purified with a mixed gradient of acetonitrile/0.1% TFA and 0.1% aqueous TFA. The pure fractions were combined and converted to the HCl salt. The title compound was obtained as a white solid. FAB ms (m+1) 452. Anal. Calc. for $C_{24}H_{23}ClFN_5O$ .2. HCl 1.7 $H_2O$: C, 51.90; H, 5.15; N, 12.61. Found: C, 52.22; H, 5.10; N, 12.22.

Example 52

4-[3-(4-Cyanobenzyl)pyridin-4-yl]-1-(3-chlorophenyl)-5(S)-(2-methylsulfonylethyl)-piperazin-2-one Step A: 3-(4-Cyanobenzyl)pyridin-4-carboxylic acid methyl ester A solution of 4-cyanobenzyl bromide (625 mg, 3.27 mmol) in dry THF (4 mL) was added slowly over ~3 min. to a suspension of activated Zn (dust; 250 mg) in dry THF (2 mL) at 0° under an argon atmosphere.

The ice-bath was removed and the slurry was stirred at room temperature for a further 30 min. Then 3-bromopyridin-4-carboxylic acid methyl ester (540 mg. 2.5 mmol) followed by dichlorobis(triphenylphosphine)nickel (II) (50 mg). The resultant reddish-brown mixture was stirred for 3 h at ~40°–45° C. The mixture was cooled and distributed between EtOAc (100 ml) and 5% aqueous citric acid (50 mL). The organic layer was washed with $H_2O$ (2×50 mL), dried with $Na_2SO_4$. After evaporation of the solvent the residue was purified on silica gel, eluting with 35% EtOAc in hexane to give 420 mg as a clear gum. FAB ms (M+1) 253.

Step B: 3-(4-Cyanobenzyl)-4-(hydroxymethyl)pyridine

The title compound was obtained by sodium borohydride (300 mg) reduction of the ester from Step A (415 mg) in methanol (5 mL) at room temperature. After stirring for 4 h the solution was evaporated and the product was purified on silica gel, eluting with 2% methanol in chloroform to give the title compound. FAB ms (M+1) 225.

Step C: 3-(4-Cyanobenzyl)-4-pyridinal

The title compound was obtained by activated manganese dioxide (1.0 g) oxidation of the alcohol from Step B (240 mg, 1.07 mmol) in dioxane (10 mL) at reflux for 30 min. Filtration and evaporation of the solvent provided title compound, mp 80°–83° C.

Step D: 4-[3-(4-Cyanobenzyl)pyridine-4-yl]-1-(3-chlorophenyl)-5(S)-(2-methylsulfonylethyl)-piperazin-2-one.

This compound was prepared essentially by the same methods as described in Example 39, Step E, except that the imidazolyl carboxaldehyde was replaced by an equal amount of product from Step C (vide supra) and the piperazinone was replaced by an equal amount of 1-(3-chlorophenyl)-5(S)-(2-methylsulfonylethyl)-piperazin-2-one, there was obtained the title compound. FAB ms 523. Anal. Calc. for $C_{27}H_{27}ClN_4O_3S.0.15$ $CHCl_3$:C, 60.28; H, 5.06; N, 10.36 Found: C, 60.37; H, 5.03; N, 10.64.

Example 53

4-[5-(4-Cyanobenzyl)-1-imidazolylethyl]-1-(3-chlorophenyl)piperazin-2-one.

Step A: 1-Trityl-4-(4-cyanobenzyl)-imidazole.

To a suspension of activated zinc dust (3.57 g, 54.98 mmol) in THF (50 ml)was added dibromoethane (0.315 ml, 3.60 mmol) and the reaction stirred under argon at 20° C. The suspension was cooled to 0° C. and α-bromo-p-tolunitrile (9.33 g, 47.6 mmol) in THF (100 ml) was added dropwise over a period of 10 min. The reaction was then allowed to stir at 20° C. for 6 hr and bis(triphenylphosphine) Nickel II chloride (2.4 g, 3.64 mmol) and 5-iodotrityl imidazole (15.95 g, 36.6 mmol) was added in one portion. The resulting mixture was stirred 16 hr at 20° C. and then quenched by addition of saturated $NH_4Cl$ solution (100 ml) and the mixture stirred for 2 hours. Saturated $NaHCO_3$ solution was added to give a pH of 8 and the solution was extracted with EtOAc (2×250 ml), dried $MgSO_4$ and the solvent evaporated in vacuo. The residue was chromatographed ($SiO_2$, 0–20% EtOAc/$CH_2Cl_2$ to afford the title compound as a white solid. $^1$H NMR δ $CDCl_3$ (7.54 (2H, d, J=7.9 Hz), 7.38 (1H, s), 7.36–7.29 (11H, m), 7.15–7.09 (6H, m), 6.58 (1H, s), and 3.93 (2H, s) ppm.

Step B: 1-Methyl acetyl-5-(4-cyanobenzyl)-imidazole.

To a solution of 1-trityl-4-(4-cyanobenzyl)-imidazole (3.01 g, 6.91 mmol) in acetonitrile (50 ml) was added methyl bromoacetate (0.687 ml, 7.26 mmol) and the mixture heated at 55° C. for 16 hours, and then the solvent was evaporated in vacuo. The solids were triturated with EtOAc, collected by filtration and dissolved in methanol (60 ml). This suspension was heated at reflux for 20 min, cooled and evaporated to dryness. The residue was triturated with EtOAc and the title compound was obtained as a white solid by filtration $^1$H NMR δ CDCl$_3$ (7.61 (2H, d, J=7.9 Hz), 7.53 (1H, s), 7.27 (2H, d, J=7.9 Hz), 6.89 (1H, s), 4.47 (2H, s), 3.98 (2H, s) and 3.66 (3H, s) ppm.

Step C: 1-Hydroxyethyl-5-(4-cyanobenzyl)-imidazole.

A solution of 1-methyl acetyl-5-(4-cyanobenzyl)-imidazole (0.113 g, 0.472 mmol) in methanol (2 ml) at 0° C. was treated with sodium borohydride (80.7 mg, 2.1 mmol). After 1 hour the reaction was quenched by addition of saturated NH$_4$Cl solution (2 ml). Saturated NaHCO$_3$ was added and the mixture extracted with ethyl acetate (3×25 ml), dried MgSO$_4$ and evaporated in vacuo. The title compound was isolated by chromatography (SiO2, 10% MeOH in CH$_2$Cl$_2$) as a white solid. $^1$H NMR δ CDCl$_3$ (7.61 (2H, d, J=7.9 Hz), 7.55 (1H, s), 7.27 (2H, d, J=7.9 Hz), 6.83 (1H, s), 4.05 (2H, s), 3.87 (2H, t, J=5.1 Hz) and 3.74 (2H, t, J=5.1 Hz) ppm.

Step D: 2-(-5-(4-Cyanobenzyl)-imidazolyl)ethyl methanesulfonate

A solution of 1-hydroxyethyl-5-(4-cyanobenzyl)-imidazole (0.532 g, 2.34 mmol) in methylene chloride (70 ml) at 0° C. was treated with Hunigs base (0.489 ml, 2.81 mmol) and methane sulfonyl chloride (0.219 ml, 2.81 mmol). After 2 hour the reaction was quenched by addition of saturated NaHCO$_3$ solution (50 ml) and the mixture extracted with methylene chloride (50 ml), dried MgSO$_4$ and the solvent evaporated in vacuo. The title compound was used without further purification. $^1$H NMR δ CDCl$_3$ (7.62 (2H, d, J=7.9 Hz), 7.54 (1H, s), 7.29 (2H, d, J=7.9 Hz), 6.87 (1H, s), 4.25 (2H, t), 4.10–4.00 (4H, m), 3.74 (2H, t, J=5.1 Hz) and 2.90 (3H, s) ppm.

Step E: 4-[5-(4-Cyanobenzyl)-1-imidazolylethyl]-1-(3-chlorophenyl)piperazin-2-one.

A solution of 2-(-5-(4-cyanobenzyl)-imidazolyl)ethyl methanesulfonate (24 mg, 0.079 mmol) in DMF (0.2 ml) was added to 3-(chlorophenyl)piperazin-2-one (17.7 mg, 0.084 mmol), sodium iodide (50 mg, 0.336 mmol) and Hunigs base (0,0146 ml, 0.084 mmol). The mixture was stirred at 55° C. for 12 hours, and the solvent evaporated in vacuo. The residue was purified by preparative tic eluting with 10% saturated ammonia/acetonitrile to afford the title compound. $^1$H NMR δ CDCl$_3$ (7.61 (2H, d, J=8.4 Hz), 7.56 (1H, s), 7.35–7.20 (7H, m), 7.16 (1H, d, J=8 Hz), 6.85 (1H, s), 4.03 (2H, s), 3.83 (2H, t, J=6.5 Hz),3.61 (2H, t, J=5.4 Hz), 3.27 (2H, s), 2.68 (2H, t, J=5.4 and 2.57 (2H, t, J=6.5 Hz) ppm.

Example 54

In vitro inhibition of ras farnesyl transferase

Assays of farnesyl-protein transferase. Partially purified bovine FPTase and Ras peptides (Ras-CVLS, Ras-CVIM and Ras-CAIL) were prepared as described by Schaber et al. *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μm ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in the above Examples and in the Tables hereinafter were tested for inhibitory activity against human FPTase by the assay described above and were found to have IC$_{50}$ of ≦50 μM.

Example 55

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 56

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.0% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 57

Tables 1–18 show other compounds of the instant invention that were prepared by the procedures described in Examples 1–53. These compounds are meant to be illustrative and are not meant to be limiting. In Table 2, the stereochemistry of the amino-containing carbon atom is as indicated (R or S) or, if unknown, the two separated stereoisomers are delineated by an "A" or "B" designation.

TABLE 1

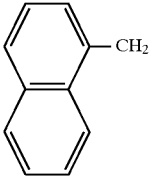

| R | FAB ms (M + 1) | Formula Analysis (Calc, Found) |
|---|---|---|
| 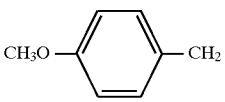 | 526 | $C_{33}H_{39}N_3OS.2.3$ TFA.0.9 $H_2O$<br>C, 56.16; H, 5.40; N, 7.22.<br>C, 56.12; H, 5.37; N, 7.39. |
| 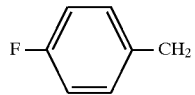 | 506 | $C_{30}H_{39}N_3O_2S.2.55$ TFA.0.55 $H_2O$<br>C, 53.19; H, 5.46; N, 5.36.<br>C, 53.17; H, 5.46; N, 5.60. |
| 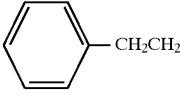 | 494 | $C_{29}H_{36}N_3OS.2.25$ TFA.0.35 $H_2O$<br>C, 53.19; H, 5.18; N, 5.55.<br>C, 53.16; H, 5.18; N, 5.68. |
| 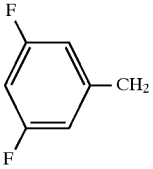 | 490 | $C_{30}H_{39}N_3OS.2$ TFA.0.9 $H_2O$<br>C, 55.64; H, 5.88; N, 5.73.<br>C, 55.57; H, 5.81; N, 5.83. |
|  | 512 | $C_{29}H_{35}F_2N_3OS.2.4$ TFA.0.6 $H_2O$<br>C, 50.99; H, 4.89; N, 5.28.<br>C, 50.98; H, 4.86; N, 5.56. |

TABLE 2

| amine stereo. | X | Y | FAB mass spectrum (M + 1) | Analysis (calcd., found) |
|---|---|---|---|---|
| A | n-Bu | 2-O(CH$_2$)$_{13}$CH$_3$ | 642.5 | C$_{42}$H$_{63}$N$_3$O$_2$.2.55HCl<br>C, 68.46; H, 8.97; N, 5.70.<br>C, 68.40; H, 8.70; N, 5.61. |
| B | n-Bu | 2-O(CH$_2$)$_{13}$CH$_3$ | 642.6 | C$_{42}$H$_{63}$N$_3$O$_2$.2.65HCl<br>C, 68.63; H, 8.99; N, 5.72.<br>C, 68.66; H, 8.90; N, 5.70. |
| A | n-Bu | 2-O(CH$_2$)$_{11}$CH$_3$ | 614.4 | C$_{40}$H$_{59}$N$_3$O$_2$.2.8HCl<br>C, 67.09; H, 8.70; N, 5.87.<br>C, 67.03; H, 8.66; N, 5.76. |
| B | n-Bu | 2-O(CH$_2$)$_{11}$CH$_3$ | 614.4 | C$_{40}$H$_{59}$N$_3$O$_2$.2.85HCl.0.05H$_2$O<br>C, 66.84; H, 8.69; N, 5.85.<br>C, 67.20; H, 8.70; N, 5.45. |
| A | n-Bu | 2-O(CH$_2$)$_9$CH$_3$ | 586.5 | C$_{38}$H$_{55}$N$_3$O$_2$3HCl.0.25hexane<br>C, 66.18; H, 8.65; N, 5.86.<br>C, 66.14; H, 8.44; N, 5.5O. |
| B | n-Bu | 2-O(CH$_2$)$_9$CH$_3$ | 586.5 | C$_{38}$H$_{55}$N$_3$O$_2$C$_3$HCl.0.15hexane<br>C, 65.97; H, 8.55; N, 5.93.<br>C, 66.04; H, 8.41; N, 5.57. |
| A | n-Bu | 2-O(CH$_2$)$_7$CH$_3$ | 558 | C$_{36}$H$_{51}$N$_3$O$_2$.2.15HCl.0.65H$_2$<br>C, 66.73; H, 8.47; N, 6.49.<br>C, 66.74; H, 8.46; N, 6.52. |
| B | n-Bu | 2-O(CH$_2$)$_7$CH$_3$ | 558 | C$_{36}$H$_{51}$N$_3$O$_2$.2.15HCl.0.65H$_2$O<br>C, 66.82; H, 8.42; N, 6.49.<br>C, 66.85; H, 8.43; N, 6.52. |
| A | n-Bu | 2-O(CH$_2$)$_3$Ph | 564 | C$_{37}$H$_{45}$N$_3$O$_2$C$_2$HCl.1.05H$_2$O<br>C, 67.78; H, 7.55; N, 6.41.<br>C, 67.78; H, 7.52; N, 6.26. |
| B | n-Bu | 2-O(CH$_2$)$_3$Ph | 564 | C$_{37}$H$_{45}$N$_3$O$_2$.2HCl.105H$_2$O<br>C, 67.78; H, 7.55; N, 6.4l.<br>C, 67.78; H, 7.44; N, 6.33. |
| A | n-Bu | 3-OCH$_2$Ph | 536 | C$_{35}$H$_{41}$N$_3$O$_2$.3.55HCl<br>C, 63.19; H, 6.75; N, 6.32.<br>C, 63.12; H, 6.61; N, 6.47. |
| B | n-Bu | 3-OCH$_2$Ph | 536 | C$_{35}$H$_{41}$N$_3$O$_2$.3.55HCl.0.4H$_2$O<br>C, 62.52; H, 6.80; N, 6.25.<br>C, 62.14; H, 6.69; N, 6.65. |
| A | n-Bu | 3-O(CH$_2$)$_{13}$CH$_3$ | 642 | C$_{42}$H$_{63}$N$_3$O$_2$.2.4HCl<br>C, 69.15; H, 9.04; N, 5.76.<br>C, 69.08; H, 9.08; N, 5.73. |
| B | n-Bu | 3-O(CH$_2$)$_{13}$CH$_3$ | 642.5 | C$_{42}$H$_{63}$N$_3$O$_2$.2.35HCl.0.25H$_2$O<br>C, 69.15; H, 9.04; N, 5.76.<br>C, 69.08; H, 9.08; N, 5.73. |
| R | n-Bu | 4-O(CH$_2$)$_{13}$CH$_3$ | 642 | C$_{42}$H$_{63}$N$_3$O$_2$.2.2HCl.1H$_2$O<br>C, 68.14; H, 9.15; N, 5.68.<br>C, 68.13; H, 9.03; N, 5.68. |
| S | n-Bu | 4-O(CH$_2$)$_{13}$CH$_3$ | 642 | C$_{42}$H$_{63}$N$_3$O$_2$.2.8HCl<br>C, 67.79; H, 8.91; N, 5.65.<br>C, 67.77; H, 9.80; N, 5.64. |
| S | n-Bu | 4-OCH$_2$Ph | 536 | C$_{35}$H$_{41}$N$_3$O$_2$.2.15HCl.1H$_2$O<br>C, 66.49; H, 7.20; N, 6.65.<br>C, 66.48; H, 7.15; N, 6.62. |
| R/S | H | 2-O(CH$_2$)$_{13}$CH$_3$ | 586 | C$_{38}$H$_{55}$N$_3$Ohd 2.1.5HCl.0.3H$_2$O<br>C, 66.88; H, 8.58; N, 6.16.<br>C, 66.82; H, 8.64; N, 6.15. |

TABLE 3

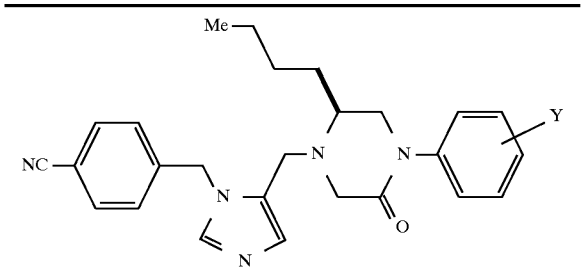

| Y | FAB mass spectrum (M + 1) | Analysis (calcd., found) |
|---|---|---|
| 3-SO₂Me | 506 | C₂₇H₃₁N₅O₃S.3.0HCl.0.10H₂O<br>C, 52.61; H, 5.59; N, 11.36.<br>C, 52.63; H, 5.41; N, 10.72. |
| 3-OCF₃ | 512.23 | C₂₇H₂₈N₅O₂F₃.2.30HCl.0.50H₂O<br>C, 53.66; H, 5.22; N, 11.59.<br>C, 53.73; H, 5.23; N, 10.86. |

TABLE 4

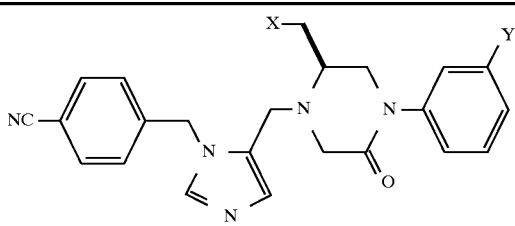

| X | Y | FAB mass spectrum (M + 1) | Analysis (calcd., found) |
|---|---|---|---|
| CH₂OCH₂Ph | CF₃ | 574 | C₃₂H₃₀N₅O₂F₃.1.40HCl.0.30H₂O<br>C, 61.02; H, 5.12; N, 11.12.<br>C, 61.01; H, 5.10; N, 10.78. |
| CH₂SO₂Et | CF₃ | 560 | C₂₇H₂₈N₅O₃F₃S.3.20HCl.0.10H₂O<br>C, 47.86; H, 4.67; N, 10.34.<br>C, 47.89; H, 4.49; N, 9.92. |
| CH₂SO₂Ph | CF₃ | 608 | C₃₁H₂₈N₅O₃F₃S.2.10HCl<br>C, 54.42; H, 4.43; N, 10.24.<br>C, 54.43; H, 4.42; N, 9.98. |
| CH₂SO₂Me | Cl | 512 | C₂₅H₂₆N₅O₃ClS<br>.2.0HCl.0.25CHCl₃.0.25H₂O<br>C, 48.97; H, 4.68; N, 11.31.<br>C, 48.95; H, 4.64; N, 11.51. |
| CH₂SO₂Et | Cl | 526 | C₂₆H₂₈N₅O₃ClS.2HCl.0.25CHCl₃<br>C, 50.14; H, 4.85; N, 11.14.<br>C, 50.20; H, 4.91; N, 10.93. |
| CONHMe | CF₃ | 511 | C₂₆H₂₅N₆O₂F₃.1.90HCl.1.70H₂O<br>C, 51.20; H, 5.01; N, 13.78.<br>C, 51.17; H, 4.99; N, 13.36. |
| CONHEt | CF₃ | 525 | C₂₇H₂₇N₆O₂F₃.1.60HCl.0.10H₂O<br>C, 55.54; H, 4.97; N, 14.39.<br>C, 55.57; H, 4.87; N, 15.28. |
| CH₂SO₂Ph | Cl | 574 | C₃₀H₂₈N₅O₃ClS.2HCl.0.30H₂O<br>C, 55.23; H, 4.73; N, 10.73.<br>C, 55.25; H, 4.57; N, 10.61. |
| CONHMe | Cl | 477 | C₂₅H₂₅N₆O₂Cl.2HCl<br>.0.105CHCl₃.0.85H₂O<br>C, 52.24; H, 5.03; N, 14.56.<br>C, 52.21; H, 5.07; N, 14.98. |
| CONHEt | Cl | 491 | C₂₆H₂₇N₆O₂Cl.2HCl.0.25CHCl₃<br>C, 53.10; H, 4.97; N, 14.15<br>C, 53.32; H, 5.21; N, 13.77. |
| CONHc-Pr | Cl | 503 | C₂₇H₂₇N₆O₂Cl.2HCl.0.40CHCl₃<br>C, 52.77; H, 4.75; N, 13.47.<br>C, 53.01; H, 4.99; N, 13.32. |
| CONHc-Pr | CF₃ | 537 | C₂₈H₂₇N₆O₂F₃.2.45HCl.0.55dioxane |

TABLE 4-continued

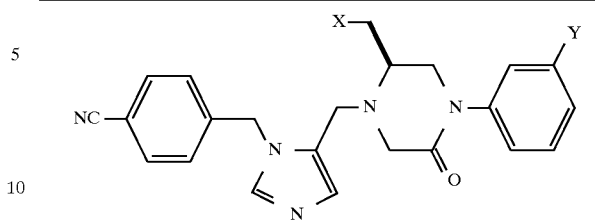

| X | Y | FAB mass spectrum (M + 1) | Analysis (calcd., found) |
|---|---|---|---|
| | | | C, 53.81; H, 5.06; N, 12.47.<br>C, 53.76; H, 5.09; N, 12.44. |
| NHCOMe | Cl | 477 | C₂₅H₂₅N₆O₂Cl<br>.2HCl.0.60CHCl₃.2.0H₂O<br>C, 46.76; H, 4.84; N, 12.78.<br>C, 46.79; H, 4.46; N, 12.37. |
| CONMe₂ | CF₃ | 525 | C₂₇H₂₇N₆O₂F₃.2.0HCl.0.10H₂O<br>C, 54.12; H, 4.91; N, 14.02.<br>C, 54.10; H, 4.96; N, 13.79. |
| SO₂Et | Cl | 512 | C₂₅H₂₆N₅O₃ClS.2.0HCl.0.10H₂O<br>C, 51.18; H, 4.84; N, 11.94.<br>C, 51.24; H, 5.19; N, 11.10. |
| CH₂SMe | Cl | 480 | C₂₅H₂₆N₅OClS.0.15CHCl₃.0.05H₂O<br>C, 52.83; H, 4.98; N, 12.25.<br>C, 52.82; H, 5.36; N, 11.85. |
| (±) C≡CMe | Cl | 458 | C₂₆H₂₄N₅OCl.2.0HCl.1.00H₂O<br>C, 56.89; H, 5.14; N, 12.76.<br>C, 56.99; H, 5.20; N, 12.42. |

TABLE 5

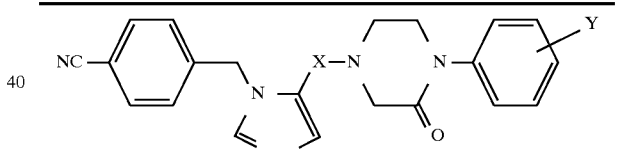

| X | Y | FAB mass spectrum (M + 1) | Analysis (calcd. found) |
|---|---|---|---|
| CH₂CH₂ | H | 386 | C₂₃H₂₃N₅O.1.40HCl.0.40H₂O<br>C, 62.29; H, 5.73; N, 15.79.<br>C, 26.26; H, 5.71; N, 15.43. |
| CH₂CO | H | 400 | C₂₃H₂₁N₅O₂.2.6HCl.1.70H₂O<br>C, 52.71; H, 5.19; N, 13.36.<br>C, 52.82; H, 5.21; N, 13.04. |
| CH₂ | H | 372 | C₂₂H₂₁N₅O.2.0HCl.2.60H₂O<br>C, 53.80; H, 5.79; N, 14.26.<br>C, 52.86; H, 5.98; N, 13.92. |
| CH₂ | 3-Cl | 406 | C₂₂H₂₀N₅OCl.2.50HCl.0.90H₂O<br>C, 51.48; H, 4.77; N, 13.65.<br>C, 51.55; H, 4.75; N, 13.34. |
| NHSO₂ | H | | C₂₁H₂₀N₆O₃S.1.0HCl.2.60H₂O<br>C, 48.53; H, 5.08; N, 16.17<br>C, 48.60; H, 5.19; N, 15.80. |
| CH₂CH₂CO | 3-Cl | 448 | C₂₄H₂₂N₅O₂Cl.1.0HCl.1.10H₂O<br>C, 57.17; H, 5.04; N, 13.89.<br>C, 57.22; H, 4.94; N, 13.47. |
| CH₂ | 2,3-Cl₂ | 440 | C₂₂H₁₉N₅OCl₂.2.0HCl.0.60H₂O<br>C, 50.42; H, 4.27; N, 13.36.<br>C, 50.51; H, 4.56; N, 12.18. |
| CH₂ | 2-Br | 450 | C₂₂H₂₀N₅OBr.2.0HCl.0.30H₂O<br>C, 49.98; H, 4.31; N, 13.25.<br>C, 49.94; H, 4.47; N, 12.53. |

TABLE 5-continued

[Structure: NC-phenyl-CH2-N(imidazole)-X-N-piperazine-N-phenyl-Y with C=O]

| X | Y | FAB mass spectrum (M + 1) | Analysis (calcd. found) |
|---|---|---|---|
| CH₂ | 3-CF₃ | 440 | $C_{23}H_{20}N_5OF_3 \cdot 1.70HCl \cdot 0.40H_2O$<br>C, 54.40; H, 4.47; N, 13.79.<br>C, 54.45; H, 4.49; N, 13.82. |
| CH₂ | 4-Cl | | $C_{22}H_{20}N_5OCl \cdot 1.50HCl \cdot 0.80H_2O$<br>C, 55.71; H, 4.91; N, 14.77.<br>C, 55.81; H, 4.94; N, 14.11. |
| CH₂CO | 3-Cl | | $C_{23}H_{20}N_5O_2Cl \cdot 1.40HCl \cdot 10H_2O$<br>C, 54.73; H, 4.71; N, 13.87.<br>C, 54.80; H, 4.73; N, 13.46. |
| CH₂ | 3-F | | $C_{22}H_{20}N_5OF \cdot 2HCl \cdot 0.35CHCl_3 \cdot 0.95H_2O$<br>C, 51.50; H, 4.69; N, 13.44.<br>C, 51.56; H, 4.73; N, 13.30. |
| CH₂ | 3-Br | | $C_{22}H_{20}N_5OBr \cdot 1.40HCl \cdot 1.30H_2O$<br>C, 50.35; H, 4.61; N, 13.34.<br>C, 50.36; H, 4.63; N, 12.84. |

TABLE 7

[Structure shown with NC-phenyl, imidazole, piperazine with Y and Cl substituents]

| X | Y | FAB mass spectrum (M + 1) | Analysis (calcd., found) |
|---|---|---|---|
| 4-Me | CH₂CH₂SO₂Me | 526 | $C_{26}H_{28}N_5O_3ClS \cdot 2HCl \cdot 0.35CHCl_3 \cdot 0.85H_2O$<br>C, 48.24; H, 4.92; N, 10.67.<br>C, 48.25; H, 4.93; N, 10.36. |
| 4-Me | H | 420 | $C_{23}H_{22}N_5OCl \cdot 2.0HCl \cdot 0.90H_2O$<br>C, 54.27; H, 5.11; N, 13.76.<br>C, 54.21; H, 5.37; N, 12.97. |
| 2-Me | H | 420 | $C_{23}H_{22}N_5OCl \cdot 3.20HCl \cdot 0.10H_2O$<br>C, 51.31; H, 4.76; N, 13.01.<br>C, 51.30; H, 4.74; N, 12.87. |

TABLE 6

[Structure with MeO₂, X-phenyl, Y, Z linker, piperazine, Cl-phenyl]

| X | Y | Z | FAB mass spectrum (M + 1) | Analysis (calcd., found) |
|---|---|---|---|---|
| 4-CN | CH₂ | 5-CH₂CH₂CO | 554 | $C_{27}H_{28}N_5O_4ClS \cdot 1.30HCl \cdot 1.20H_2O$<br>C, 52.05; H, 5.13; N, 11.24.<br>C, 52.09; H, 5.15; N, 10.95. |
| 3-CN | CH₂ | 5-CH₂ | 512 | $C_{25}H_{26}N_5O_3ClS \cdot 2.0HCl \cdot 0.10CHCl_3 \cdot 0.60H_2O$<br>C, 49.61; H, 4.86; N, 11.52.<br>C, 49.63; H, 5.01; N, 11.14. |
| 2-CN | CH₂ | 5-CH₂ | 512 | $C_{25}H_{26}N_5O_3ClS \cdot 2HCl \cdot 0.35H_2O$<br>C, 50.79; H, 4.89; N, 11.84.<br>C, 50.82; H, 5.29; N, 11.90. |
| 4-CN | CH₂ | 4-CH₂CH₂CO | 554 | $C_{27}H_{28}N_5O_4ClS \cdot 2.0HCl \cdot 0.50CHCl_3 \cdot 0.60H_2O$<br>C, 47.36; H, 4.58; N, 10.04.<br>C, 47.35; H, 4.60; N, 9.66. |
| 4-CN | (CH₂)2 | 4-CH₂CH₂CO | | $C_{28}H_{30}N_5O_4ClS \cdot 1.0HCl \cdot 0.40CHCl_3 \cdot 0.95H_2O$<br>C, 50.96; H, 5.01; N, 10.46.<br>C, 50.91; H, 5.02; N, 10.13. |

TABLE 8

| Y | FAB ms (m + 1) | Formula Analysis Calc Found |
|---|---|---|
| 3-CF$_3$ | 496 | C$_{27}$H$_{28}$F$_3$N$_5$O.2HCl.1.55H$_2$O<br>C, 54.36; H, 5.59; N, 11.74<br>C, 54.40; H, 5.29; N, 11.26 |
| 3-CH$_3$ | 442 | C$_{27}$H$_{31}$N$_5$O.2HCl<br>C, 63.01; H, 6.47; N, 13.61<br>C, 63.45; H, 6.71; N, 13.53 |
| 2,3-(CH$_2$)$_4$ | 482 | C$_{30}$H$_{35}$N$_5$O.5.2HCl.0.1H$_2$O<br>C, 53.66; H, 6.06; N, 0.43<br>C, 53.62; H, 5.30; N, 9.35 |
| 3-OCH$_3$ | 458 | C$_{27}$H$_{31}$N$_5$O$_2$. 2HCl<br>C, 61.13; H, 6.27; N, 13.20<br>C, 62.43; H, 6.53; N, 13.24 |
| 3-Cl | 463 | C$_{26}$H$_{28}$ClN$_5$O.2HCl.0.75H$_2$O<br>C, 56.94; H, 5.79; N, 12.77<br>C, 56.92; H, 5.59; N, 12.30 |
| 2-CH$_3$, 3-Cl | 477 | C$_{27}$H$_{30}$ClN$_5$O$_{2.2HCl.3.1H_2O}$<br>C, 53.62; H, 6.37; N, 11.58<br>C, 53.44; H, 5.37; N, 10.76 |
| H | 428 | C$_{26}$H$_{29}$N$_5$O.3.9HCl.2H$_2$O<br>C, 51.63; H, 6.51; N, 11.58<br>C, 51.59; H, 5.10; N, 10.35 |
| 3-F | 446 | C$_{26}$H$_{28}$FN$_5$O.2HCl.2.55H$_2$O<br>C, 55.87; H, 6.22; N, 12.53<br>C, 55.83; H, 5.84; N, 11.71 |

TABLE 9

| R | FAB ms (m + 1) | Formula Analysis Calc Found |
|---|---|---|
| CH$_2$CH$_2$OCH$_2$CF$_3$ | 566 | C$_{27}$H$_{25}$F$_6$N$_5$O$_2$.2HCl.0.67H$_2$O<br>C, 49.85; H, 4.39; N, 10.77<br>C, 49.86; H, 4.26; N, 10.33 |
| cyclopropyl-OCH$_2$CH$_2$ | 524 | C$_{28}$H$_{28}$F$_3$N$_5$O$_2$.2HCl<br>C, 56.38; H, 5.07; N, 11.74<br>C, 56.21; H, 5.27; N, 11.46 |
| CH$_2$CH$_2$N$_3$ | 509 | C$_{25}$H$_{23}$F$_3$N$_8$O$_2$.2HCl.2.35H$_2$O<br>C, 48.14; H, 4.80; N, 17.96<br>C, 48.79; H, 4.38; N, 16.99 |
| CH$_2$CH$_2$NHCOCH$_3$ | 525 | C$_{27}$H$_{27}$F$_3$N$_6$O$_2$.2HCl.0.7H$_2$O<br>C, 53.16; H, 5.02; N, 13.78<br>C, 53.30; H, 5.07; N, 13.39 |
| CH$_2$CH$_2$NHCOC$_2$H$_5$ | 539 | C$_{28}$H$_{29}$F$_3$N$_6$O$_2$.2HCl.3.66H$_2$O<br>C, 52.43; H, 5.39; N, 13.10<br>C, 52.44; H, 5.20; N, 12.48 |
| CH$_2$CH$_2$SO$_2$CH(CH$_3$)$_2$ | 574 | C$_{28}$H$_{30}$F$_3$N$_5$O$_3$S.2HCl.1.35H$_2$O<br>C, 50.13; H, 5.21; N, 10.44<br>C, 50.10; H, 4.88; N, 10.08 |
| CH$_2$CH$_2$SCH(CH$_3$)$_2$ | 542 | C$_{28}$H$_{30}$F$_3$N$_5$OS.2HCl.0.75H$_2$O<br>C, 53.55; H, 5.38; N, 11.51<br>C, 53.57; H, 5.33; N, 11.04 |
| CH$_2$CH$_2$S(O)CH(CH$_3$)$_2$ | 558 | C$_{28}$H$_{30}$F$_3$N$_5$O$_2$S.2HCl.0.7H$_2$O<br>C, 52.29; H, 5.23; N, 10.89<br>C, 52.27; H, 5.08; N, 10.35 |

TABLE 10

| R | FAB ms (m + 1) | Formula Analysis Calc Found |
|---|---|---|
| 4-O$_2$N-C$_6$H$_4$-N(imidazolyl-CH$_3$) | 462 | C$_{26}$H$_{31}$N$_5$O$_3$.2 CF$_2$CO$_2$H.2.8 H$_2$O<br>C, 48.69; H, 5.26; N, 9.46<br>C, 48.70; H, 4.42; N, 9.12 |

TABLE 10-continued
| R | FAB ms (m + 1) | Formula Analysis Calc Found |
|---|---|---|
|  | 470 | $C_{29}H_{35}N_5O.2$ HCl.0.3 $CH_2Cl_2$.0.6 $C_6H_{14}$<br>C, 63.76; H, 7.48; N, 11.30<br>C, 64.77; H, 7.07; N, 11.26 |
| 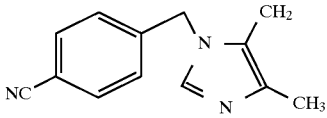 | 431 | $C_{27}H_{34}N_4O.2$ HCl<br>C, 64.41; H, 7.21; N, 11.13<br>C, 66.35; H, 7.28; N, 11.25 |
| 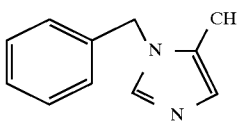 | 445 | $C_{28}H_{36}N_4O.2$ HCl.1.3 $H_2O$<br>C, 62.17; H, 7.56; N, 10.36<br>C, 62.15; H, 7.09; N, 9.83 |
| 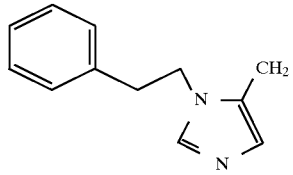 | 470 | $C_{29}H_{35}N_5O.2$ HCl.3.05 $H_2O$<br>C, 58.30; H, 7.27; N, 11.72<br>C, 58.30; H, 6.28; N, 10.90 |
| 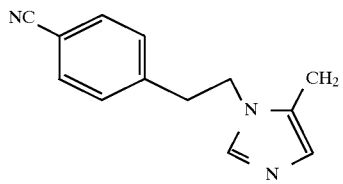 | 548, 550 | $C_{29}H_{34}BrN_5O.2$ HCl.0.1 $H_2O$<br>C, 55.89; H, 5.85; N, 11.24<br>C, 55.91; H, 5.96; N, 10.73 |
TABLE 11
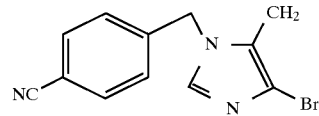
| R | Y | FAB ms (m + 1) | Formula Analysis Calc Found |
|---|---|---|---|
| 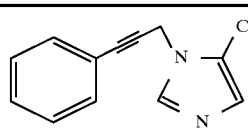 | Cl | 511 | $C_{26}H_{27}ClN_4O_3S.2$ HCl.2.85 $H_2O$<br>C, 49.16; H, 5.51; N, 8.82<br>C, 49.17; H, 4.74; N, 8.87 |

TABLE 11-continued
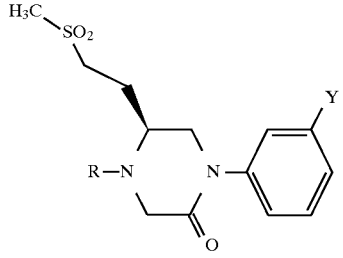
| R | Y | FAB ms (m + 1) | Formula Analysis Calc Found |
|---|---|---|---|
| 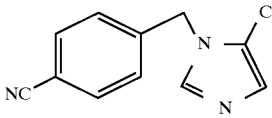 | F | 496 | C25H26FN5O3S.2 HCl.1.65 H2O<br>C, 50.20; H, 5.27; N, 11.71<br>C, 50.19; H, 4.90; N, 11.44 |
| 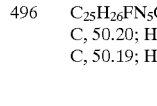 | Cl | 527 | C26H28ClN5O3S.2 HCl.0.55 H2O<br>C, 51.29; H, 5.15; N, 11.50<br>C, 51.32; H, 5.39; N, 11.31 |
| 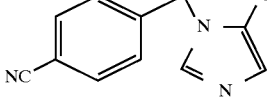 | Cl | 530 | C26H32ClN5O3S.3 HCl.0.6 HCl<br>C, 48.02; H, 5.61; N, 10.77<br>C, 48.30; H, 5.91; N, 9.78 |
TABLE 12
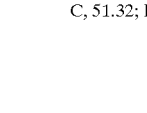
| R | FAB ms (m + 1) | Formula Analysis Calc Found |
|---|---|---|
| 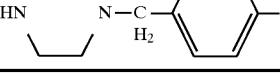 | 545 | C26H30ClN5O4S.2 HCl.0.75 H2O<br>C, 49.53; H, 5.36; N, 11.11<br>C, 49.56; H, 5.58; N, 10.65 |
| 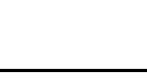 | 552 | C28H29ClN5O3S.2 HCl<br>C, 53.90; H, 5.01; N, 11.22<br>C, 54.06; H, 5.78; N, 10.67 |
| 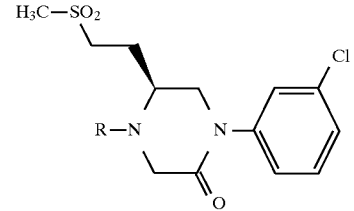 | 396 | C17H20ClN4O3S.2 HCl.0.7 H2O<br>C, 42.41; H, 4.90; N, 11.64<br>C, 42.98; H, 5.49; N, 11.06 |

TABLE 12-continued
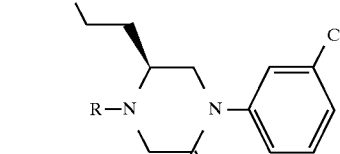
| R | FAB ms (m + 1) | Formula Analysis Calc Found |
|---|---|---|
| 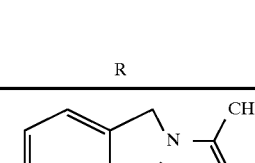 | 544 | $C_{26}H_{30}ClN_5O_4S\cdot2\ HCl\cdot0.75\ H_2O$<br>C, 49.51; H, 5.36; N, 11.11<br>C, 49.74; H, 5.66; N, 10.11 |
| 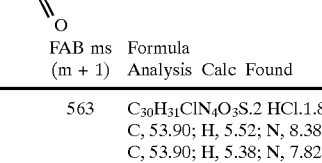 | 524 | $C_{27}H_{27}ClN_4O_3S\cdot0.55\ CHCl_3$<br>C, 58.67; H, 4.92; N, 10.03<br>C, 58.71; H, 4.94; N, 9.95 |
|  | 523 | $C_{28}H_{28}ClN_3O_3S\cdot0.1\ CHCl_3\cdot0.2\ CH_3OH$<br>C, 62.89; H, 5.39; N, 7.78<br>C, 62.87; H, 5.37; N, 7.84 |
TABLE 13
| R | FAB ms (m + 1) | Formula Analysis Calc Found |
|---|---|---|
|  | 563 | $C_{30}H_{31}ClN_4O_3S\cdot2\ HCl\cdot1.8\ H_2O$<br>C, 53.90; H, 5.52; N, 8.38<br>C, 53.90; H, 5.38; N, 7.82 |

TABLE 13-continued
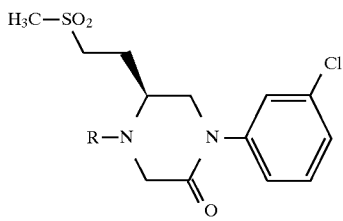
| R | FAB ms (m + 1) | Formula Analysis Calc Found |
|---|---|---|
| 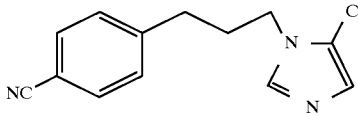 | 540 | $C_{27}H_{30}ClN_5O_3S.2$ HCl.1.35 $H_2O$<br>C, 50.88; H, 5.49; N, 10.99<br>C, 51.37; H, 5.51; N, 10.20 |
| 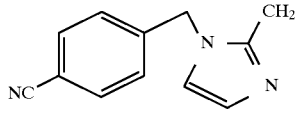 | 512 | $C_{25}H_{26}ClN_5O_3S.2$ HCl.0.3 $H_2O$<br>C, 50.86; H, 4.88; N, 11.86<br>C, 51.06; H, 5.33; N, 10.87 |
| 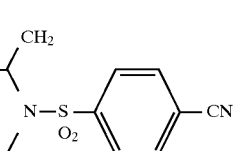 | 415 | $C_{28}H_{27}ClN_4O_3S.3$ HCl.4 $H_2O$<br>C, 36.25; H, 6.42; N, 9.39<br>C, 38.12; H, 5.91; N, 7.41 |
| 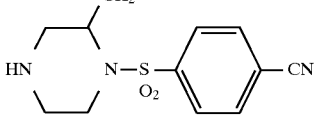 | 580 | $C_{25}H_{30}ClN_5O_5S_2.2$ HCl.0.85 $H_2O$<br>C, 44.93; H, 5.08; N, 10.48<br>C, 44.96; H, 5.08; N, 9.96 |
TABLE 14
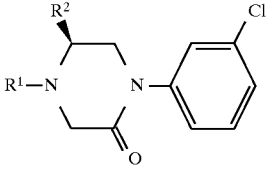
| $R^1$ | $R^2$ | FAB ms (m + 1) | Formula Analysis Calc Found |
|---|---|---|---|
| 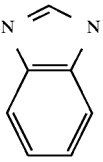 | H | 355 | $C_{19}H_{19}ClN_4O.2$ HCl.0.5 $H_2O$<br>C, 52.25; H, 5.08; N, 12.83<br>C, 52.31; H, 5.14; N, 12.23 |
| 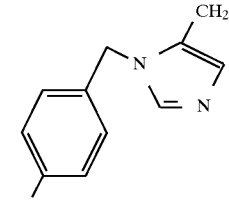 | $CH_2CH_2F$ | 452 | $C_{24}H_{23}ClFN_5O.2$ HCl.1.70 $H_2O$<br>C, 51.90; H, 5.15; N, 12.61<br>C, 52.22; H, 5.10; N, 12.22 |

TABLE 14-continued
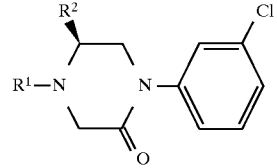
| R¹ | R² | FAB ms (m + 1) | Formula Analysis Calc Found |
|---|---|---|---|
| 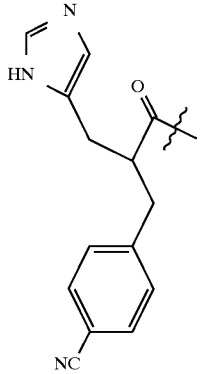 | H | 448 | $C_{24}H_{22}ClN_5O_2 \cdot 1\ HCl \cdot 0.30\ CHCl_3 \cdot 0.85\ H_2O$<br>C, 54.50; H, 4.71; N, 13.08<br>C, 54.51; H, 4.69; N, 12.87 |
TABLE 15
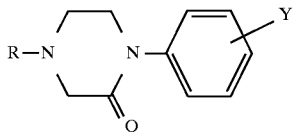
| R | Y | FAB ms (m + 1) | Formula Analysis Calc Found |
|---|---|---|---|
| 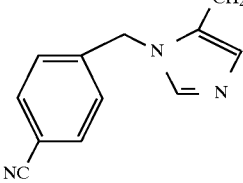 | CH₂ 2,3-(CH₂)₄ | 426 | $C_{26}H_{27}N_5O \cdot 2\ HCl \cdot 0.15\ H_2O$<br>C, 62.31; H, 5.89; N, 13.97<br>C, 62.38; H, 6.18; N, 13.27 |
| 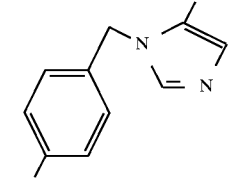 | CH₂ 2-CH₃, 3-Cl | 420 | $C_{23}H_{22}ClN_5O \cdot 2\ HCl \cdot 1.0\ H_2O$<br>C, 54.08; H, 5.13; N, 13.71<br>C, 54.57; H, 5.77; N, 12.92 |
| 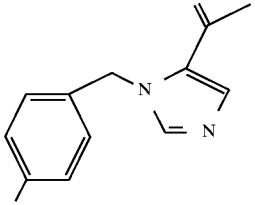 | O⟍ 3-Cl | 420 | $C_{22}H_{18}ClN_5O_2 \cdot 2\ HCl \cdot 0.5\ H_2O$<br>C, 56.78; H, 4.33; N, 15.05<br>C, 56.79; H, 4.69; N, 13.47 |

TABLE 16

[Structure: piperazine with n-C₄H₉ substituent, N-naphthoyl group, and R-N group]

| R | FAB ms (m + 1) | Formula Analysis Calc Found |
|---|---|---|
| [4-cyanobenzyl-imidazolyl-CH₂CH₂ group] | 506 | C₃₂H₃₅N₅O.3.2CF₃CO₂H.2.65H₂O<br>C, 54.14; H, 5.75; N, 9.15<br>C, 54.15; H, 5.74; N, 9.18 |
| [pyridine N-oxide-imidazolyl-CH₂ group] | 484 | C₂₉H₃₃N₅O₂.4HCl.3H₂O<br>C, 51.03; H, 6.35; H, 10.26<br>C, 51.02; H, 5.66; N, 9.67 |
| [4-cyanophenethyl-imidazolyl-CH₂ group] | 506 | C₃₂H₃₅N₅O.2HCl.1.7H₂O<br>C, 63.09; H, 6.68; N, 10.26<br>C, 51.02; H, 5.66; N, 9.67 |

TABLE 17

[Structure: piperazinone with R-N and N-phenyl groups]

| R | FAB ms (m + 1) | Formula Analysis Calc Found |
|---|---|---|
| [imidazolyl-benzyl-CH₂CH₂ group] | 347 | C₂₁H₂₂N₄O.0.2 CHCl₃.<br>0.4 CH₃OH<br>C, 67.71; H, 6.26; N, 14.62<br>C, 67.71; H, 6.26; N, 14.53 |
| [pyridyl-benzyl-CH₂ group] | 358 | C₂₃H₂₃N₃O.0.55 CHCl₃<br>C, 66.85; H, 5.61; N, 9.93<br>C, 66.87; H, 5.70; N, 10.03 |

TABLE 18

| Structure | FAB mass spectrum (M + 1) | Analysis (calcd., found) |
|---|---|---|
| (structure with 2,3-dimethylphenyl, n-butyl, 4-cyanobenzyl-imidazolyl, piperazinone) | | $C_{29}H_{33}N_5O_2 \cdot 1.0HCl \cdot 0.25CHCl_3 \cdot 0.70H_2O$<br>C, 62.45; H, 6.39; N, 12.45.<br>C, 62.45; H, 6.46; N, 12.37. |
| (structure with 3-chlorophenyl, 4-cyanobenzyl, imidazole-NH) | 406 | $C_{22}H_{20}N_5OCl \cdot 2.60HCl$<br>C, 53.97; H, 4.78; N, 14.30<br>C, 53.97; H, 5.21; N, 13.10. |
| (structure with MeO₂S-ethyl, 3-chlorobenzyl, 4-cyanobenzyl-imidazolyl, piperazinone) | 526 | $C_{26}H_{28}N_5O_3ClS \cdot 2.0HCl \cdot 1.20H_2O$<br>C, 50.32; H, 5.26; N, 11.28<br>C, 50.31; H, 5.31; N, 10.72. |
| (structure with 3-chlorophenyl, 4-cyanobenzyl-imidazolylethyl, piperazinone) | 420 | $C_{23}H_{22}N_5OCl \cdot 2.0HCl \cdot 2.10H_2O$<br>C, 52.06; H, 5.36; N, 13.20<br>C, 51.99; H, 5.36; N, 12.57. |

What is claimed is:

1. A compound which inhibits farnesyl-protein transferase which is:

5(S)-n-Butyl-1-(2,3-dimethylphenyl)-4-(4-imidazolylmethyl)-piperazin-2-one

5(S)-n-Butyl-4-[1-(4-cyanobenzyl)imidazol-5-ylmethyl]-1-(2,3-dimethylphenyl)piperazin-2-one 4-[1-(4-Cyanobenzyl)imidazol-5-ylmethyl]-1-(2,3-dimethylphenyl)-5(S)-(2-methoxyethyl)piperazin-2-one (S)-1-(3-Chlorophenyl)-4-[1-(4-cyanobenzyl)-5-imidazolylmethyl]-5-[2-(methanesulfonyl)ethyl]-2-piperazinone (S)-1-(3-Chlorophenyl)-4-[1-(4-cyanobenzyl)-5-imidazolylmethyl]-5-[2-(ethanesulfonyl)ethyl]-2-piperazinone (R)-1-(3-Chlorophenyl)-4-[1-(4-cyanobenzyl)-5-imidazolylmethyl]-5-[2-(ethanesulfonyl)methyl]-2-piperazinone (S)-1-(3-Chlorophenyl)-4-[1-(4-cyanobenzyl)-5-imidazolylmethyl]-5-[N-ethyl-2-acetamido]-2-piperazinone (±)-5-(2-Butynyl)-1-(3-chlorophenyl)-4-[1-(4-cyanobenzyl)-5-imidazolylmethyl]-2-piperazinone 1-(3-Chlorophenyl)-4-[1-(4-cyanobenzyl)-5-imidazolylmethyl]-2-piperazinone 5(S)-Butyl-4-[1-(4-cyanobenzyl-2-methyl)-5-imidazolylmethyl]-1-(2,3-dimethylphenyl)-piperazin-2-one 4-[1-(2-(4-Cyanophenyl)-2-propyl)-5-imidazolylmethyl]-1-(3-chlorophenyl)-5(S)-(2-methylsulfonylethyl) piperazin-2-one 5(S)-n-Butyl-4-[1-(4-cyanobenzyl)-5-imidazolylmethyl]-1-(2-methylphenyl)piperazin-2-one 4-[1-(4-Cyanobenzyl)-5-imidazolylmethyl]-5(S)-(2-fluoroethyl)-1-(3-chlorophenyl)piperazin-2-one 4-[5-(4-Cyanobenzyl)-1-imidazolylethyl]-1-(3-chlorophenyl)piperazin-2-one or a pharmaceutically acceptable salt or optical isomer thereof.

2. The compound according to claim 1 which is:

5(S)-n-Butyl-4-[1-(4-cyanobenzyl)imidazol-5-ylmethyl]-1-(2,3-dimethylphenyl)piperazin-2-one

121

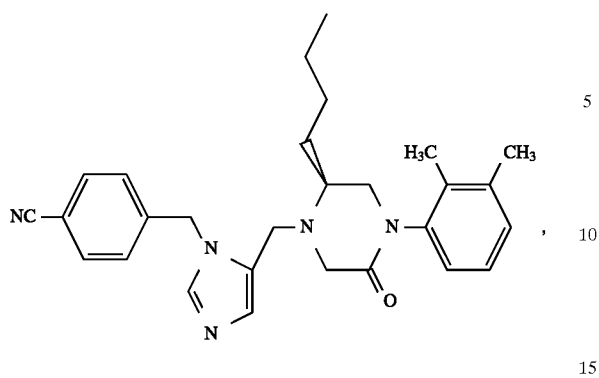

or a pharmnaceutically acceptable salt or optical isomer thereof.

3. The compound according to claim 1 which is:

4-[1-(4-Cyanobenzyl)imidazol-5-ylmethyl]-1-(2,3-dimethylphenyl)-5(S)-(2-methoxyethyl)piperazin-2-one

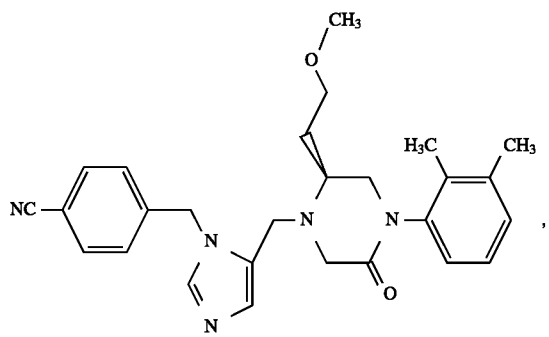

or a pharmaceutically acceptable salt or optical isomer thereof.

4. The compound according to claim 1 which is:

5(S)-n-Butyl-4-[1-(4-cyanobenzyl)-5-imidazolylmethyl]-1-(2-methylphenyl)piperazin-2-one

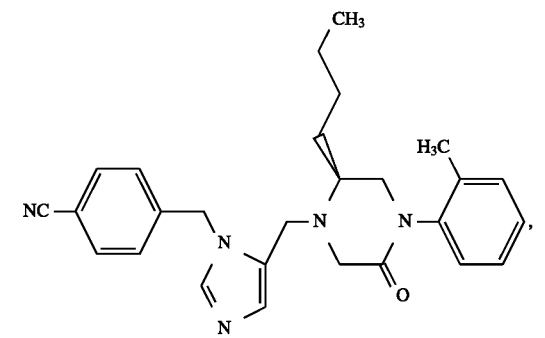

or a pharmaceutically acceptable salt or optical isomer thereof.

5. The compound according to claim 1 which is:

(S)-1-(3-Chlorophenyl)-4-[1-(4-cyanobenzyl)-5-imidazolylmethyl]-5-[2-(methanesulfonyl)ethyl]-2-piperazinone

122

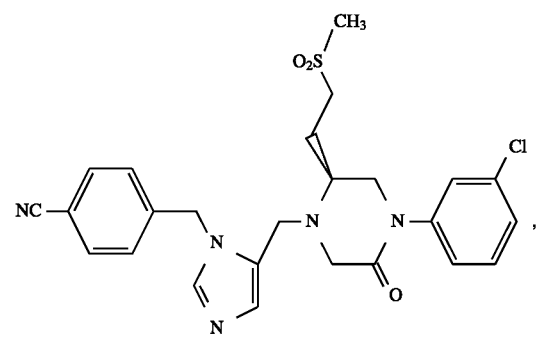

or a pharmaceutically acceptable salt or optical isomer thereof.

6. The compound according to claim 1 which is:

(S)-1-(3-Chlorophenyl)-4-[1-(4-cyanobenzyl)-5-imidazolylmethyl]-5-[2-(ethanesulfonyl)ethyl]-2-piperazinone

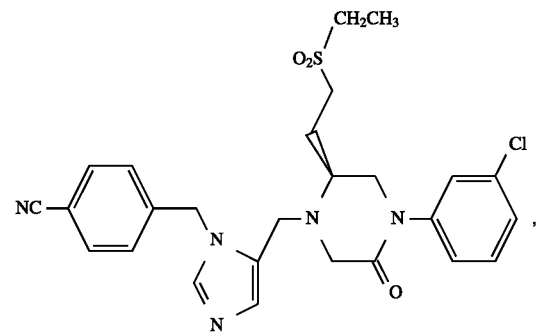

or a pharmaceutically acceptable salt or optical isomer thereof.

7. The compound according to claim 1 which is:

(S)-1-(3-Chlorophenyl)-4-[1-(4-cyanobenzyl)-5-imidazolylmethyl]-5-[2-(ethanesulfonyl)methyl]-2-piperazinone

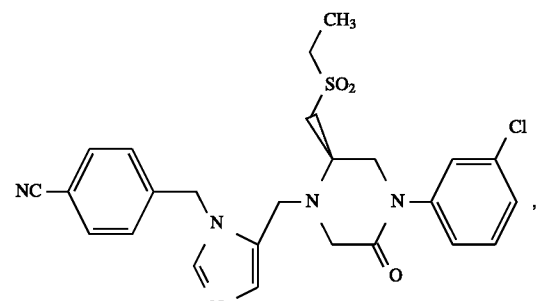

or a pharmaceutically acceptable salt or optical isomer thereof.

8. The compound according to claim 1 which is:

1-(3-Chlorophenyl)-4-[1-(4-cyanobenzyl)-5-imidazolylmethyl]-2-piperazinone

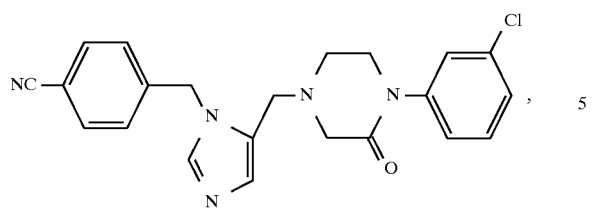

or a pharmaceutically acceptable salt or optical isomer thereof.

9. A pharmaceutical composition comprising a pharmaceutical carrier, and dispersed therein, a therapeutically effective amount of a compound of claim 1.

10. A compound which inhibits farnesyl-protein transferase of the formula B:

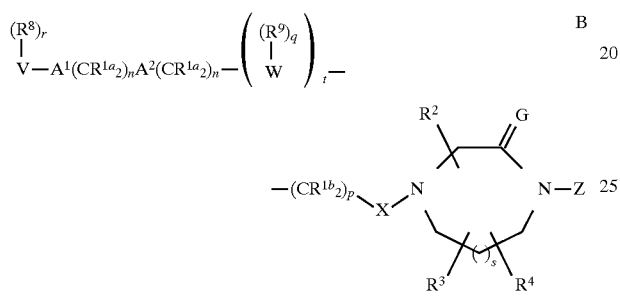

wherein:

$R^{1a}$ and $R^{1b}$ are independently selected from:
  a) hydrogen,
  b) aryl, $C_3$–$C_{10}$ cycloalkyl, $C_2$–$C_6$ alkenyl, $C_2$–$C_6$ alkynyl, $R^{10}O$—, $R^{11}S(O)_m$-, $R^{10}C(O)NR^{10}$-, $CN(R^{10})_2NC(O)$—, $R^{10}{}_2N\text{-}C(NR^{10})$—, CN, $NO_2$, $R^{10}C(O)$—, $R^{10}OC(O)$—, $N_3$, —$N(R^{10})_2$, or $R^{11}OC(O)NR^{10}$-,
  c) unsubstituted or substituted $C_1$–$C_6$ alkyl wherein the substitutent on the substituted $C_1$–$C_6$ alkyl is selected from aryl, cyanophenyl, $C_3$–$C_{10}$ cycloalkyl, $C_2$–$C_6$ alkenyl, $C_2$–$C_6$ alkynyl, $R^{10}O$—, $R^{11}S(O)_m$-, $R^{10}C(O)NR^{10}$-, $(R^{10})_2NC(O)$—, $R^{10}{}_2N\text{-}C(NR^{10})$—, CN, $R^{10}C(O)$—, $R^{10}OC(O)$—, $N_3$, —$N(R^{10})_2$, and $R^{11}OC(O)NR^{10}$-;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl,

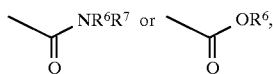

wherein the substituted group is substituted with one or more of:
1) aryl, unsubstituted or substituted with;
   a) $C_{1-4}$ alkyl,
   b) $(CH_2)_pOR^6$,
   c) $(CH_2)_pNR^6R^7$,
   d) halogen,
   e) CN,
2) $C_{3-6}$ cycloalkyl,
3) $OR^6$,
4) $SR^{6a}$, $S(O)R^{6a}$, $SO_2R^{6a}$, 5) 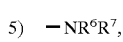—$NR^6R^7$, 6) 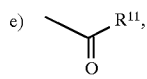

7) 
$$-\underset{\underset{O}{\|}}{\overset{R^6}{\underset{|}{N}}}-\underset{\|}{C}-NR^7R^{7a},$$

8) —O—C(O)—$NR^6R^7$,

9) —O—C(O)—$OR^6$,

10) —C(O)—$NR^6R^7$,

11) —$SO_2$—$NR^6R^7$,

12) $-\underset{\underset{}{\overset{R^6}{|}}}{N}-SO_2-R^{6a}$,

13) —C(O)—$R^6$,

14) —C(O)—$OR^6$,

15) $N_3$, or
16) F;

$R^4$ is selected from H and $CH_3$;
and any two of $R^2$, $R^3$ and $R^4$ are optionally attached to the same carbon atom;

$R^6$, $R^7$ and $R^{7a}$ are independently selected from: H; $C_{1-4}$ alkyl, $C_{3-6}$ cycloalkyl, aryl, aroyl, and arylsulfonyl, unsubstituted or substituted with:
  a) $C_{1-4}$ alkoxy,
  b) aryl,
  c) halogen,
  d) HO, e) 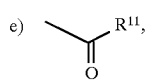—$R^{11}$, f) —SO, or
  g) $N(R^{10})_2$;

$R^{6a}$ is selected from: $C_{1-4}$ alkyl, $C_{3-6}$ cycloalkyl, aryl, unsubstituted or substituted with:
  a) $C_{1-4}$ alkoxy,
  b) aryl,
  c) halogen,
  d) HO, e) —C(O)—$R^{11}$, f) —SO, or
  g) $N(R^{10})_2$;

$R^8$ is independently selected from:

a) hydrogen,
b) aryl, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$-, $R^{10}C(O)NR^{10}$-, $(R^{10})_2NC(O)$—, $R^{10}{}_2N$-$C(NR^{10})$—, CN, $NO_2$, $R^{10}C(O)$—, $R^{10}OC(O)$, $N_3$, —$N(R^{10})_2$, or $R^{11}OC(O)NR^{10}$-, and
c) $C_1$–$C_6$ alkyl unsubstituted or substituted by aryl, cyanophenyl, $C_3$–$C_{10}$ cycloalkyl, $C_2$–$C_6$ alkenyl, $C_2$–$C_6$ akynyl, perfluoroalkyl, F, Cl, Br, $R^{10}O$—, $R^{11}S(O)_m$-, $R^{10}C(O)NH$—, $(R^{10})_2NC(O)$—, $R^{10}{}_2N$-$C(NR^{10})$—, CN, $R^{10}C(O)$—, $R^{10}OC(O)$—, $N_3$, —$N(R^{10})_2$, or $R^{10}OC(O)NH$—;

$R^9$ is selected from:
a) hydrogen,
b) alkenyl, alkynyl, perfluoroalkyl, F, Cl, Br, $R^{10}O$—, $R^{11}S(O)_m$-, $R^{10}{}_2N$-$C(NR^{10})$—, CN, $NO_2$, $R^{10}C(O)$—, $R^{10}OC(O)$—, $N_3$ or $R^{11}OC(O)NR^{10}$-, and
c) $C_1$–$C_6$ alkyl unsubstituted or substituted by perfluoroalkyl, F, Cl, Br, $R^{10}O$—, $R^{11}S(O)_m$-, $R^{10}{}_2N$-$C(NR^{10})$—, CN, $R^{10}C(O)$—, $R^{10}OC(O)$—, $N_3$ or $R^{11}OC(O)NR^{10}$-;

$R^{10}$ is independently selected from hydrogen, $C_1$–$C_6$ alkyl, benzyl and aryl;
$R^{11}$ is independently selected from $C_1$–$C_6$ alkyl and aryl;
$A^1$ and $A^2$ are independently selected from: a bond, —CH=CH—, —C≡C—, —C(O)— or O;
G is O;
V is phenyl or naphthyl;
W is imidazolyl;
X is —$CH_2$-, —$C(=O)$—, or —$S(=O)_m$-;
Z is a unsubstituted or substituted group selected from phenyl, benzyl, naphthyl and naphthylmethyl, wherein the substituted group is substituted with one or more of the following:
1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl,
   e) HO,
   f) —$S(O)_m R^{6a}$, or
   g) —$C(O)NR^6R^7$,
2) aryl,
3) halogen,
4) $OR^6$,
5) $NR^6R^7$,
6) CN,
7) $NO_2$,
8) $CF_3$;
9) —$S(O)_m R^{6a}$,
10) —$C(O)NR^6R^7$, or
11) $C_3$–$C_6$ cycloalkyl;
aryl is independently selected from phenyl, naphthyl, tetrahydronaphthyl, indanyl and biphenyl;
m is 0, 1 or 2;
n is 0, 1, 2, 3 or 4;
p is 0, 1, 2, 3 or 4;
q is 1 or 2;
r is 0 to 5;
s is 0;
t is 1; and
u is 4 or 5;
or an optical isomer or pharmaceutically acceptable salt thereof.

11. The compound according to claim 10 of the formula B:

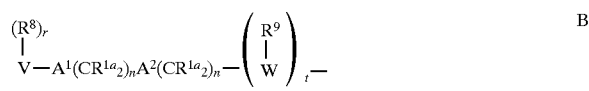

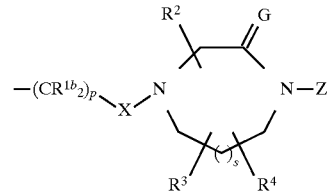

wherein:
$R^{1a}$ is independently selected from: hydrogen or $C_1$–$C_6$ alkyl;
$R^{1b}$ is independently selected from:
a) hydrogen,
b) aryl, cycloalkyl, $R^{10}O$-, —$N(R^{10})_2$ or $C_2$–$C_6$ alkenyl,
c) unsubstituted or substituted $C_1$–$C_6$ alkyl wherein the substitutent on the substituted $C_1$–$C_6$ alkyl is selected from aryl, cyanophenyl, cycloalkyl, alkenyl, $R^{10}O$— and —$N(R^{10})_2$;
$R^3$ and $R^4$ are independently selected from H and $CH_3$;
$R^2$ is H;

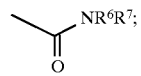

$C_{1-5}$ alkyl, unbranched or branched, unsubstituted or substituted with one or more of:
1) aryl,
2) $OR^6$,
3) $SR^{6a}$, $SO_2R^{6a}$, or
4) 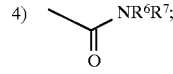

and any two of $R^2$, $R^3$ and $R^4$ are optionally attached to the same carbon atom;
$R^6$, $R^7$ and $R^{7a}$ are independently selected from:
H; $C_{1-4}$ akyl, $C_{3-6}$ cycloalkyl, aryl, unsubstituted or substituted with:
   a) $C_{1-4}$ alkoxy,
   b) halogen, or
   c) aryl;
$R^{6a}$ is selected from:
$C_{1-4}$ alkyl or $C_{3-6}$ cycloalkyl, unsubstituted or substituted with:
   a) $C_{1-4}$ alkoxy,
   b) halogen, or
   c) aryl;
$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$-, CN, $NO_2$, $(R^{10})_2N$-$C(NR^{10})$—, $R^{10}C(O)$—, $R^{10}OC(O)$—, —$N(R^{10})_2$, or $R^{11}OC(O)NR^{10}$-, and
c) $C_1$–$C_6$ alkyl substituted by $C_1$–$C_6$ perfluoroalkyl, $R^{10}O$—, $R^{10}C(O)NR^{10}$-, $(R^{10})_2N$-$C(NR^{10})$—, $R^{10}C(O)$—, $R^{10}OC(O)$—, —$N(R^{10})_2$, or $R^{11}OC(O)NR^{10}$-;
$R^9$ is selected from: hydrogen or methyl;
$R^{10}$ is independently selected from hydrogen, $C_1$–$C_6$ alkyl, benzyl and aryl;
$R^{11}$ is independently selected from $C_1$–$C_6$ alkyl and aryl;

A¹ and A² are independently selected from: a bond, —CH=CH—, —C≡C—, —C(O)—, —C(O)NR¹⁰-, O, —N(R¹⁰)—, or S(O)$_m$;

V is phenyl;
G is O;
W is imidazolyl;
X is —CH$_2$- or —C(=O)—;
Z is phenyl or naphthyl, unsubstituted or substituted with one or two of the following:
  1) C$_{1-4}$ alkyl, unsubstituted or substituted with:
     a) C$_{1-4}$ alkoxy,
     b) NR⁶R⁷,
     c) C$_{3-6}$ cycloalkyl,
     d) aryl,
     e) HO,
     f) —S(O)$_m$R⁶, or
     g) —C(O)NR⁶R⁷,
  2) aryl,
  3) halogen,
  4) OR⁶,
  5) NR⁶R⁷,
  6) CN,
  7) NO$_2$,
  8) CF$_3$;
  9) —S(O)$_m$R⁶,
  10) —C(O)NR⁶R⁷, or
  11) C$_3$–C$_6$ cycloalkyl;

aryl is independently selected from phenyl, naphthyl, tetrahydronaphthyl, indanyl and biphenyl;

m is 0, 1 or 2;
n is 0, 1, 2, 3 or 4;
p is 0, 1, 2, 3 or 4;
r is 0 to 5;
s is 0;
t is 1; and
u is 4 or 5;

or pharmaceutically acceptable salt thereof.

12. A pharmaceutical composition comprising a pharmaceutical carrier, and dispersed therein, a therapeutically effective amount of a compound of claim 10.

13. A compound which inhibits farnesyl-protein transferase which is:

TABLE 3

| Y |
|---|
| 3-SO$_2$Me |
| 3-OCF$_3$ |

TABLE 4

| X | Y |
|---|---|
| CH$_2$OCH$_2$Ph | CF$_3$ |
| CH$_2$SO$_2$Et | CF$_3$ |
| CH$_2$SO$_2$Ph | CF$_3$ |
| CH$_2$SO$_2$Me | Cl |
| CH$_2$SO$_2$Et | Cl |
| CONHMe | CF$_3$ |
| CONHEt | CF$_3$ |
| CH$_2$SO$_2$Ph | Cl |
| CONHMe | Cl |
| CONHEt | Cl |
| CONHc-Pr | Cl |
| CONHc-Pr | CF$_3$ |
| NHCOMe | Cl |
| CONHMe$_2$ | CF$_3$ |
| SO$_2$Et | Cl |
| CH$_2$SMe | Cl |
| (±) C≡CMe | Cl |

TABLE 5

| X | Y |
|---|---|
| CH$_2$CH$_2$ | H |
| CH$_2$CO | H |
| CH$_2$ | H |
| CH$_2$ | 3-Cl |
| CH$_2$CH$_2$CO | 3-Cl |
| CH$_2$ | 2,3-Cl$_2$ |
| CH$_2$ | 2-Br |
| CH$_2$ | 3-CF$_3$ |
| CH$_2$ | 4-Cl |
| CH$_2$CO | 3-Cl |
| CH$_2$ | 3-F |
| CH$_2$ | 3-Br |

TABLE 6

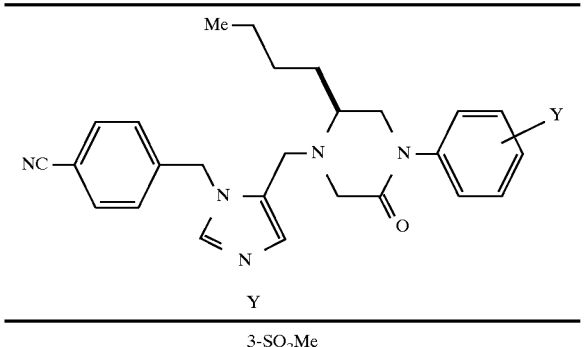

| X | Y | Z |
|---|---|---|
| 4-CN | CH$_2$ | 5-CH$_2$CH$_2$CO |
| 3-CN | CH$_2$ | 5-CH$_2$ |
| 2-CN | CH$_2$ | 5-CH$_2$ |

TABLE 6-continued

| X | Y | Z |
|---|---|---|
| 4-CN | CH₂ | 4-CH₂CH₂CO |
| 4-CN | (CH₂)₂ | 4-CH₂CH₂CO |

TABLE 7

| X | Y |
|---|---|
| 4-Me | CH₂CH₂SO₂Me |
| 4-Me | H |
| 2-Me | H |

TABLE 8

Y

3-CF₃
3-CH₃
2,3-(CH₂)₄
3-OCH₃
3-Cl
2-CH₃, 3-Cl
H
3-F

TABLE 9

R

CH₂CH₂OCH₂CF₃

(cyclopropyl)-OCH₂CH₂

CH₂CH₂N₃
CH₂CH₂NHCOCH₃
CH₂CH₂NHCOC₂H₅
CH₂CH₂SO₂CH(CH₃)₂
CH₂CH₂SCH(CH₃)₂
CH₂CH₂S(O)CH(CH₃)₂

TABLE 10

R

TABLE 10-continued

[Structure: piperazinone with n-C4H9 and 2,3-dimethylphenyl substituents, R-N group]

| R |
|---|
| [Structure: 4-cyanobenzyl-N connected to imidazole with CH2 and Br substituents] |

TABLE 11

[Structure: piperazinone with H3C—SO2 containing ethyl chain and 3-Y-phenyl substituent, R-N group]

| R | Y |
|---|---|
| [Structure: phenylpropargyl-N-imidazole with CH2] | Cl |
| [Structure: 4-cyanobenzyl-N-imidazole with CH2] | F |
| [Structure: 1-(4-cyanophenyl)ethyl-N-imidazole with CH2] | Cl |

TABLE 12

[Structure: piperazinone with H3C—SO2 ethyl chain and 3-chlorophenyl substituent, R-N group]

| R |
|---|
| [Structure: 1-(4-carbamoylphenyl)ethyl-N-imidazole with CH2] |

TABLE 13

[Structure: piperazinone with H3C—SO2 ethyl chain and 3-chlorophenyl substituent, R-N group]

| R |
|---|
| [Structure: 4-phenylbenzyl-N-imidazole with CH2] |
| [Structure: 3-(4-cyanophenyl)propyl-N-imidazole with CH2] |
| [Structure: 4-cyanobenzyl-N-imidazole with CH2] |

TABLE 14
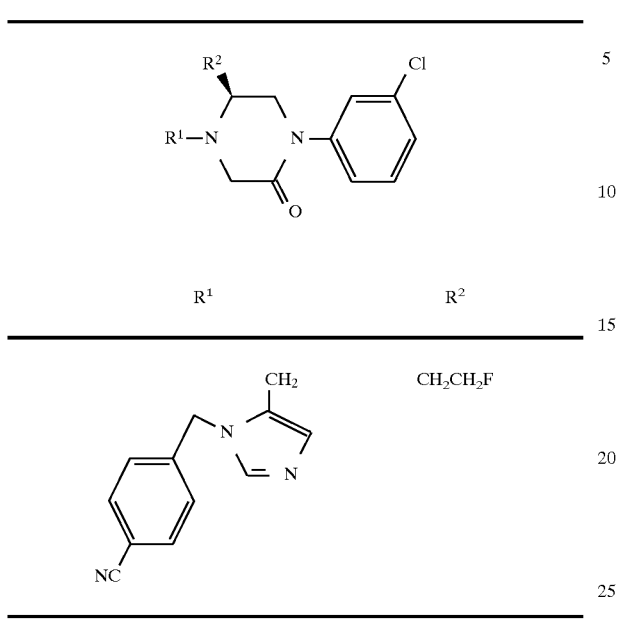
| R[1] | R[2] |
|---|---|
| (4-cyanobenzyl-imidazolyl-CH2) | CH2CH2F |
TABLE 15
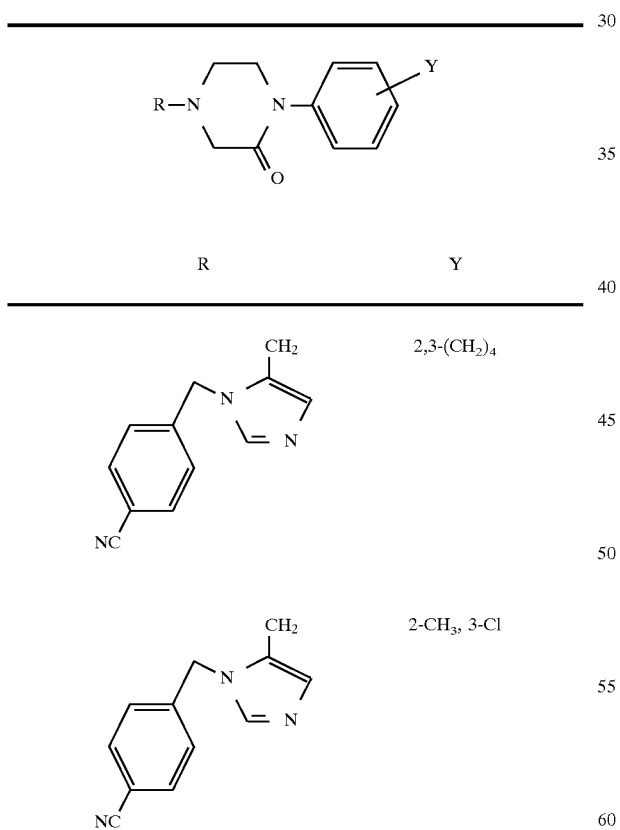
| R | Y |
|---|---|
| (4-cyanobenzyl-imidazolyl-CH2) | 2,3-(CH2)4 |
| (4-cyanobenzyl-imidazolyl-CH2) | 2-CH3, 3-Cl |
TABLE 15-continued
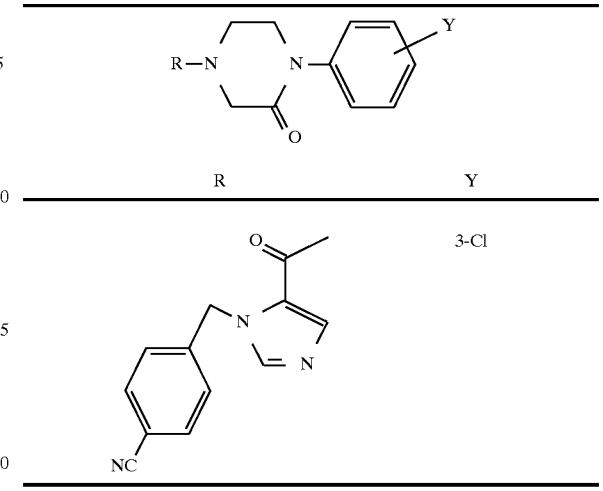
| R | Y |
|---|---|
| (4-cyanobenzyl-acetyl-imidazolyl) | 3-Cl |
TABLE 17
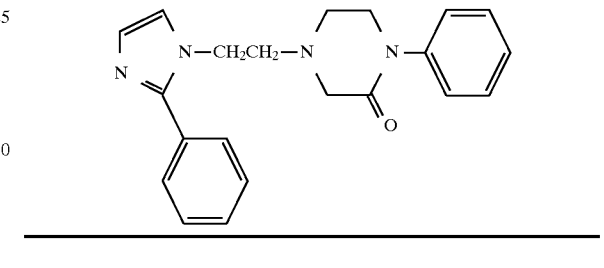
TABLE 18
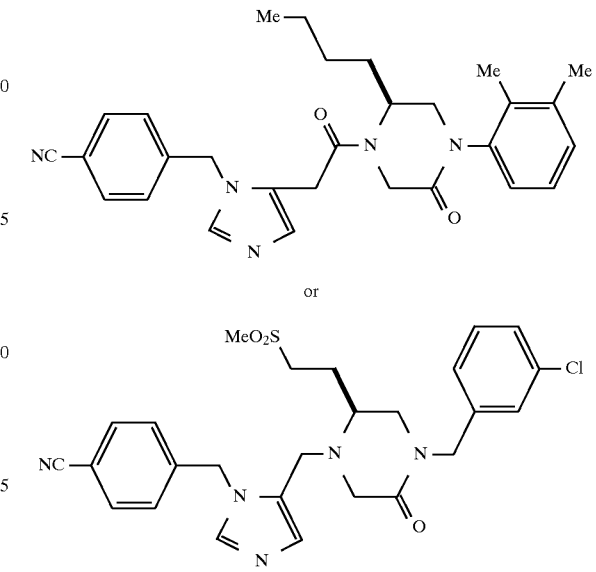
or a pharmaceutically acceptable salt or optical isomer thereof.
* * * * *

UNITED STATES PATENT AND TRADEMARK OFFICE
CERTIFICATE OF CORRECTION

PATENT NO. : 5,856,326
DATED : January 5, 1999
INVENTOR(S) : Neville Anthony et al.

It is certified that error appears in the above-identified patent and that said Letters Patent is hereby corrected as shown below:

(1) In Column 123, at lines 20-30, the structure should read:

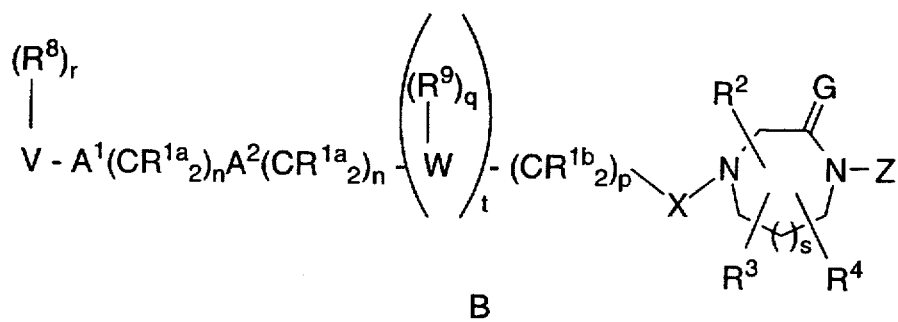

(2) At Column 124, at line 65, the line should read:

f) $SO_2R^{11}$, or

UNITED STATES PATENT AND TRADEMARK OFFICE
CERTIFICATE OF CORRECTION

PATENT NO. : 5,856,326
DATED : January 5, 1999
INVENTOR(S) : Neville Anthony et al.

It is certified that error appears in the above-identified patent and that said Letters Patent is hereby corrected as shown below:

(3) In Column 126, at lines 1-10, the structure should read:

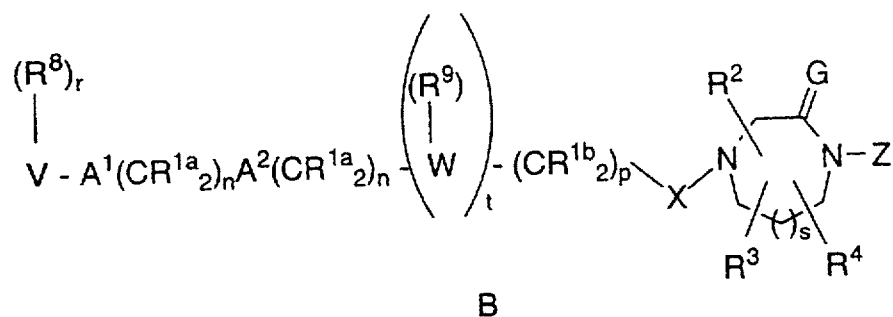

Signed and Sealed this

Eighteenth Day of May, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,856,326
DATED : January 5, 1999
INVENTOR(S) : Neville Anthony et al.

It is certified that error appears in the above-identified patent and that said Letters Patent is hereby corrected as shown below:

Column 1,
Lines 8-9, should read, -- in-part application of copending application Ser. No 08/412,829, filed Mar. 29, 1995, now abandoned. --
Line 38, should read -- on the specific sequence, this motif serves as a signal --

Column 4,
Line 59, should read, -- 1) aryl or heterocycle, unsubstituted or substituted with: --

Column 6,
Line 25, should read, -- -N($R^{10}$)$_2$, or $R^{10}$OC(O)NH-; --

Column 9,
Line 47, should read, -- -N($R^{10}$)$_2$, or $R^{10}$OC(O)NH-; --

Column 10,
Line 15, should read, -- replaced with a a heteroatom selected from O, S, and N, --

Column 17,
Line 31, should read, -- b) heterocycle selected from pyrrolidinyl, imidazolyl, --

Column 19,
Line 15, should read, -- trifluoromethylbenzyl)imidazol-5-ylmethyl]-piperazine --

Column 22,
Line 53, shoud read, -- (S)-1-(3-Chlorophenyl)-4-[1-(4-cyanobenzyl) --

Column 23,
Line 68 should read, -- tetrahydronaphthyl, indanyl, or biphenyl. --

Column 26,
Line 51, should read, -- and unsubstituted or substituted thienyl. More preferably, Z --

Column 27,
Line 44, should read -- Synopsis of Schemes 1-22: --

Column 28,
Line 27, should read -- (Scheme 4). The trityl protecting group can be removed --

UNITED STATES PATENT AND TRADEMARK OFFICE
CERTIFICATE OF CORRECTION

PATENT NO. : 5,856,326
DATED : January 5, 1999
INVENTOR(S) : Neville Anthony et al.

It is certified that error appears in the above-identified patent and that said Letters Patent is hereby corrected as shown below:

Column 31,
Scheme 1 continued, lines 5-15, should read,

--
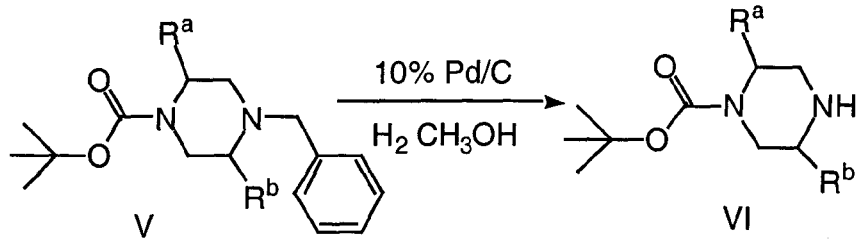
--

Column 33-34,
Scheme 3 continued, should read,

--
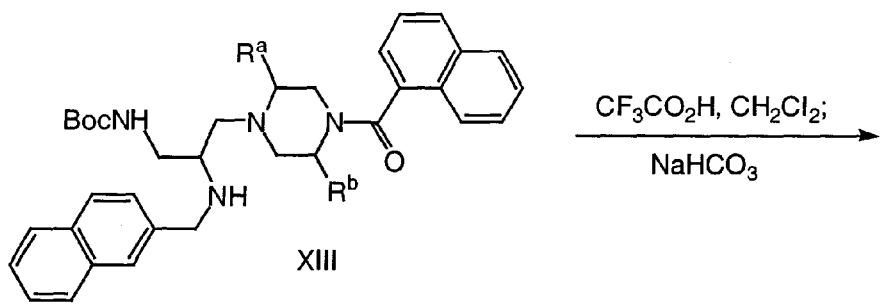
--

Column 36,
Scheme 4 continued, lines 40, should read,

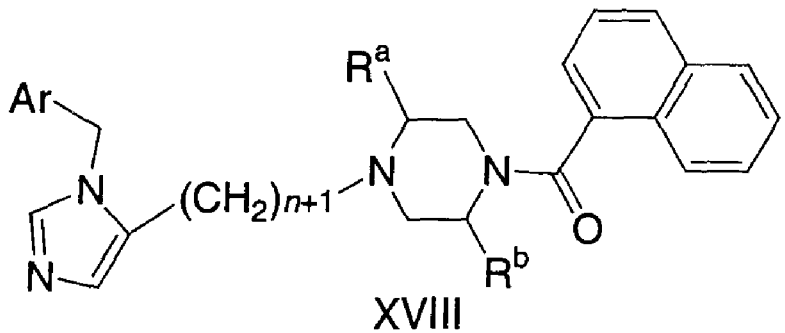

UNITED STATES PATENT AND TRADEMARK OFFICE
CERTIFICATE OF CORRECTION

PATENT NO.   : 5,856,326
DATED        : January 5, 1999
INVENTOR(S)  : Neville Anthony et al.

Page 3 of 9

It is certified that error appears in the above-identified patent and that said Letters Patent is hereby corrected as shown below:

Column 36,
Scheme 5 continued, lines 60-65, should read:

--

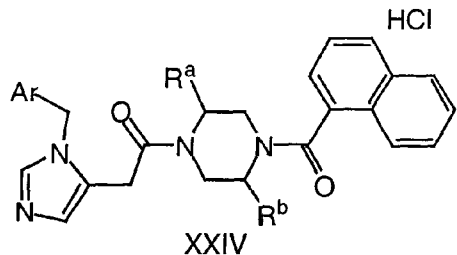

--

Column 43,
Scheme 12, lines 52-58, should read,

--

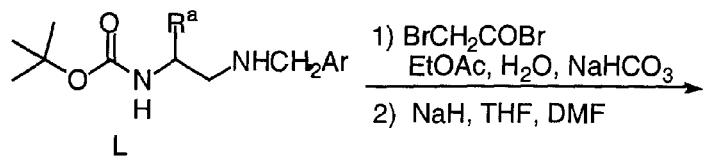

--

Column 46,
Scheme 15 continued, lines 5-15, should read,

--

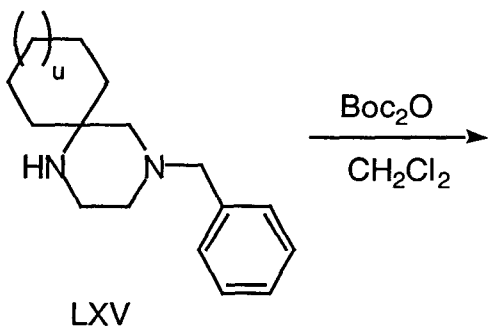

--

UNITED STATES PATENT AND TRADEMARK OFFICE
CERTIFICATE OF CORRECTION

PATENT NO. : 5,856,326
DATED : January 5, 1999
INVENTOR(S) : Neville Anthony et al.

It is certified that error appears in the above-identified patent and that said Letters Patent is hereby corrected as shown below:

Column 49,
Scheme 17 continued, lines 25-40, should read,
--

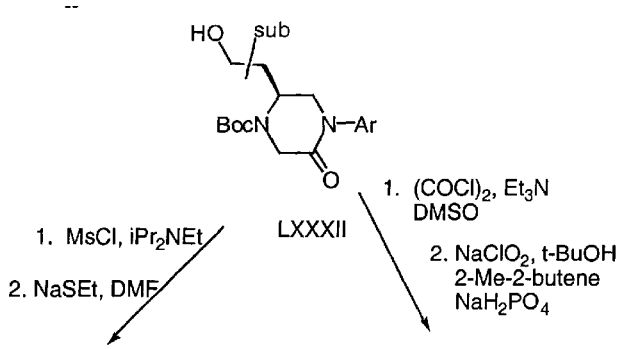

--

Column 56,
Example 1, Step A, line 12, should read, -- by tlc. The solvent was removed in vacuo, and the residue --
Example 1, Step C, lines 52 and 53, should read, -- psi hydrogen for 24 h. The catalyst was removed by filtration through Celite, and the filtrate evaporated in vacuo to give the --
Example 1, Step D, line 67, should read, -- ylformamide (DMF) was distilled in vacuo, and the residue --

Column 62,
Example 11, Step A, line 12, should read, -- drying with magnesium sulfate, the title compound was --
Example 12, Step A, line 50, should read, -- N-benzylglycinate (9.32 g, 48.2 mmol) and dicyclohexyl --

Column 63,
Example 12, Step F, line 33, should read, -- piperazine ditrifluoroacetate --

Column 64,
Example 14, line 17, should read, -- (S)-butyl-4-(1-naphthoyl)piperazine ditrifluoroacetate --
Example 14, line 22, should read, -- lamine (0.200 mL) for 2 h. The crude product was chromato --
Example 15, Step B, line 57, should read, -- Step B: 2-(1-triphenylmethyl-lH-imidazol-4-yl) --

UNITED STATES PATENT AND TRADEMARK OFFICE
CERTIFICATE OF CORRECTION

PATENT NO.    : 5,856,326
DATED         : January 5, 1999
INVENTOR(S)   : Neville Anthony et al.

It is certified that error appears in the above-identified patent and that said Letters Patent is hereby corrected as shown below:

Column 65,
Example 16, line 41, should read, -- mmol) and 3(S)-butyl-l-naphthoylpiperazine hydrochloride --
Example 16, line 63, should read, -- 8.53 (1H, s), 7.94 (2H, m), 7.79 (1H, m), 7.53 (3H, m), 7.41 --

Column 66,
Example 17, Step A, line 19, should read, -- To a suspension of the product from Step A (7.48 g, 42.4 --
Example 17, Step C, line 53, should read,-- 7.70 (1H, s), 7.49 (3H, m), 7.20 (1H, d, J=8.4 Hz), 7.06 (1H, --
Example 17, Step D, line 63, should read, -- 7.88 (2H, m), 7.83 (1H, s), 7.54 (3H, m), 7.43 (1H, d, J=14 --

Column 67,
Example 18, line 23, should read, -- yl)ethyl]-4-(1-naphthoyl)piperazine ditrifluoroacetate --
Example 18, Step A, lines 28-29, should read, -- dimethylformamide (15 ml) was added sequentially N, O-dimethylhydroxylamine hydrochloride (293 mg, 3.0 mmol), --
Example 18, Step C, line 65, should read, -- Step C: Preparation of 2 (S)-Butyl-l-[(1-naphth-2- --

Column 68,
Example 19, Step C, lines 61-62, should read, -- column chromatography (silica gel; hexane/EtOAc 1:1) to give the title compound as a foam. Rf (silica; hexane/EtoAc --

Column 69,
Example 20, line 26, should read, -- chloride salt. FAB Mass spectrum, m/z=384 (M+1). --
Example 21, Step B, line 44, should read, -- through celite rinsing with THF and the solvent was removed --

Column 70,
Example 22, Step A, line 35, should read, -- an oil which showed 2 well resolved spots on silica tlc. --

UNITED STATES PATENT AND TRADEMARK OFFICE
CERTIFICATE OF CORRECTION

PATENT NO.    : 5,856,326                                Page 6 of 9
DATED         : January 5, 1999
INVENTOR(S)   : Neville Anthony et al.

It is certified that error appears in the above-identified patent and that said Letters Patent is hereby corrected as shown below:

Column 71,
Example 24, line 42, should read, -- naphthylmethyl)imidazol-5-ylmethyl]-piperazine --
Example 25, line 62, should read, -- [5-(3-triphenylmethylimidazolyl) methyl]-4-(1-naphthoyl) --

Column 72,
Example 26, line 8, should read, -- 2(S)-n-Butyl-l-[1-(4-cyanobenzyl)imidazol-5 --
Example 26, line 21, should read, -- Found: C, 57.93; H, 4.91; N, 9.55. --
Example 27, lines 25 and 26, should read, -- 2(S)-n-Butyl-l-[1-(4-methoxybenzyl) imidazol-5-
ylmethyl]-4-(1-naphthoyl)piperazine ditrifluoroacetic --
Example 27, line 29, should read, -- [5-(3-triphenylmethylimidazolyl) methyl]-4-(1-naphthoyl) --

Column 73,
Example 29, line 5, should read, -- lyophilization. FAB ms (m+l) 485. Anal. Calc. for --
Example 31, line 28, should read, -- 1-[1-(4-Bromobenzyl)imidazol-5-ylmethyl]-2 (S)-n- --

Column 74,
Example 35, line 41, should read, -- 50 min.) and lyophilization. FAB ms (m+l) 543. Anal. Calc. --

Column 75,
Example 38, Step B, line 29, should read, -- triethylamine (57.2 ml, 0.412 mol) and triphenylmethyl - --

Column 77,
Example 39, Step E, line 30, should read, -- triphenylmethylimidazolyl)methyl] piperazin-2-one --
Example 39, Step E, line 36, should read, -- dichloroethane (20 mL). Sodium triacetoxy-borohydride -

Column 78,
Example 41, Step A, line 22, should read, -- 4-Benzyloxy-2 (S)-(tert-buyoxycarbonylamino)butanoic --
Example 41, Step C, line 35, should read, -- (S)-(tert-butoxycarbonylamino) butanamine --
Example 41, Step F, line 63, should read, -- The product from Step E (0.241 g, 0.688 mmol) was --

UNITED STATES PATENT AND TRADEMARK OFFICE
CERTIFICATE OF CORRECTION

PATENT NO. : 5,856,326
DATED : January 5, 1999
INVENTOR(S) : Neville Anthony et al.

It is certified that error appears in the above-identified patent and that said Letters Patent is hereby corrected as shown below:

Column 81,
Example 42, Step H, line 4, should read, -- to -45°C. Analysis by tlc revealed incomplete reaction. The --
Example 42, Step I, line 27, should read, -- A solution of the product from Step H (22.0 g, 63.8 mmol) --

Column 82,
Example 43, Step A, line 38, should read, -- butylpyrocarbonate (1.75 g, 8.0 mmol) and diisopropylethy- --

Column 84,
Example 43, Step J, line 12, should read, -- ethyl]-2-piperazinone dihydrochloride --
Example 44, Step A, line 43, should read, -- dropwise addition of N-methylmorpholine to achieve a pH --

Column 85,
Example 44, Step G, line 66, should read, -- brine, dried ($Na_2SO_4$), filtered, and concentrated in vacuo --

Column 88,
Example 46, Step G, line 16, should read, -- (3-chlorophenyl)-4-butynamine --
Example 46, Step H, line 31, should read, -- and triethylamine (1.20 mL, 8.61 mmol) in 15 mL of $CH_2CL_2$ --
Example 46, Step H, line 40, should read, -- brown oil. This material was purified by silica gel chroma- --

Column 89,
Example 47, Step B, line 27, should read, -- chlorophenyl)ethylenediamine -

Column 90,
Example 47, Step E, line 9, should read, -- until tlc analysis indicated complete extraction. The com- --

Column 91,
Example 49, Step C, line 58, should read, -- A solution of 5-tert-butyldimethylsilyloxy-methyl-l-(4- --

Column 92,
Example 49, Step E, line 27, should read, -- A solution of
1-[2-(4-cyanophenyl)-2-propyl)]-5- --

UNITED STATES PATENT AND TRADEMARK OFFICE
CERTIFICATE OF CORRECTION

PATENT NO.    : 5,856,326
DATED         : January 5, 1999
INVENTOR(S)   : Neville Anthony et al.

It is certified that error appears in the above-identified patent and that said Letters Patent is hereby corrected as shown below:

Column 92,
Example 50, Step A, line 64, should read, -- hane (10 mL). The crude product was purified by column --

Column 95,
Example 53, Step E, line 46, should read, -- vacuo. The residue was purified by preparative tlc eluting --
Example 53, Step E, line 51, should read, -- 3.27 (2H, s), 2.68 (2H, t, J=5.4 Hz) and 2.57 (2H, t, J=6.5 Hz) --

Column 97,
Example 56, line 11, should read, -- (0.6%). Both layers contain 0.1% methanol or an appropri- --

Column 99-100,
Table 2, compound 6, should read,
-- B    n-Bu    2-O(CH$_2$)$_9$CH$_3$    586.5    C$_{38}$H$_{55}$N$_3$O$_2$•3HCl•0.15hexane
C, 65.97; H, 8.55; N, 5.93.
C, 66.04; H, 8.41; N, 5.57. --

Table 2, compound 9, should read,
-- A    n-Bu    2-O(CH$_2$)$_3$Ph    564    C$_{37}$H$_{45}$N$_3$O$_2$•2HCl•1.05H$_2$O
C, 67.78; H, 7.55; N, 6.41.
C, 67.78; H, 7.52; N, 6.26. --

Table 2, compound 10, should read,
-- B    n-Bu    2-O(CH$_2$)$_3$Ph    564    C$_{37}$H$_{45}$N$_3$O$_2$•2HC1•1.05H$_2$0
C, 67.78; H, 7.55; N, 6.41.
C, 67.78; H, 7.44; N, 6.33. --

Table 2, compound 18, should read,
-- R/S    H    2-O(CH$_2$)$_{13}$CH$_3$    586    C$_{38}$H$_{55}$N$_3$O$_2$•1.5HCl•0.3H$_2$O
C, 66.88; H, 8.58; N, 6.16.
C, 66.82; H, 8.64; N, 6.15. --

Column 103,
Table 6, the structure should read,
--

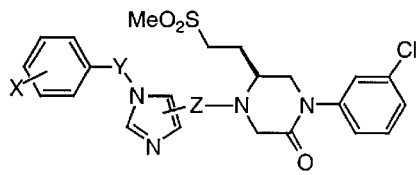

--

UNITED STATES PATENT AND TRADEMARK OFFICE
CERTIFICATE OF CORRECTION

PATENT NO. : 5,856,326
DATED : January 5, 1999
INVENTOR(S) : Neville Anthony et al.

It is certified that error appears in the above-identified patent and that said Letters Patent is hereby corrected as shown below:

Table 6, compound 5, should read
-- 4-CN      $(CH_2)_2$     4-$CH_2CH_2CO$      $C_{28}H_{30}N_5O_4ClS$
                                               •1.0HCl•0.40$CHCl_3$•0.95$H_2O$
                                               C, 50.96; H, 5.01; N, 10.46.
                                               C, 50.91; H, 5.02; N, 10.13. --

Column 105,
Table 8, coompound 3, lines 24-26, should read,
-- 2,3-$(CH_2)_4$    482                       $C_{30}H_{35}N_5O$•5.2HCl•0.1$H_2O$
                                               C, 53.66; H, 6.06; N, 0.43.
                                               C, 53.62; H, 5.30; N, 9.35. --

Table 8, compound 6, lines 35-37, should read,
-- 2-$CH_3$ 3-Cl   477        $C_{27}H_{30}ClN_5O_2$ · 2 HCl · 3.1 $H_2O$
                              C, 53.62; H, 6.37; N, 11.58
                              C, 53.44; H, 5.37; N, 10.76 --

Column 106,
Table 10, compound 1, should read,

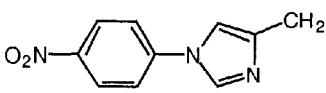

462   $C_{26}H_{31}N_5O_3$ · 2 $CF_2CO_2H$ · 2.8 $H_2O$

C, 48.69; H, 5.26; N, 9.46
C, 48.70; H, 4.42; N, 9.12

--

Signed and Sealed this

Fourth Day of June, 2002

Attest:

JAMES E. ROGAN
Attesting Officer    Director of the United States Patent and Trademark Office